United States Patent [19]

Müller et al.

[11] Patent Number: 5,399,704
[45] Date of Patent: Mar. 21, 1995

[54] HERBICIDAL SUBSTITUTED 4,5-DIAMINO-1,2,4-TRIAZOL-3-(THI)ONES

[75] Inventors: Klaus-Helmut Müller, Düsseldorf; Kurt Findeisen, Leverkusen; Michael Haug, Bergisch-Gladbach; Ulrich Heinemann, Leichlingen; Joachim Kluth, Langenfeld; Klaus König, Odenthal; Hans-Joachim Santel, Leverkusen; Klaus Lürssen; Robert R. Schmidt, both of Bergisch Gladbach, all of Germany

[73] Assignee: Bayer Aktiengesellschaft, Leverkusen, Germany

[21] Appl. No.: 979,984

[22] Filed: Nov. 23, 1992

Related U.S. Application Data

[60] Division of Ser. No. 764,437, Sep. 23, 1991, Pat. No. 5,220,032, which is a division of Ser. No. 565,293, Aug. 9, 1990, Pat. No. 5,082,490, and a continuation-in-part of Ser. No. 583,883, Sep. 17, 1990, Pat. No. 5,089,627, which is a division of Ser. No. 382,163, Jul. 19, 1989, Pat. No. 4,988,381.

[30] Foreign Application Priority Data

Aug. 30, 1989 [DE] Germany .................. 39 28 662.2

[51] Int. Cl.⁶ .............................. C07D 249/12
[52] U.S. Cl. ................................ 548/263.8
[58] Field of Search ........................ 548/263.8

[56] References Cited

U.S. PATENT DOCUMENTS 5,089,627  2/1992  Muller et al. ............. 548/263.6

OTHER PUBLICATIONS

Lieber et al, "Thiatriazoles–azido and, etc" CA 58:4543g (1963).
Kurzer et al, "Heterocyclic Compounds from Urea, etc" J. Chem. Soc. (C) 1968, pp. 2099–2107.
Emilsson et al, "Synthesis and antihypertensive, etc" Eur. J. Med Chem–Chim Ther, 1986, 21 (3) pp. 235–244.

Gehlen et al, "Über die Bildung, etc" Liebigs Ann. Chem. 702, 101–111 (1967).

*Primary Examiner*—Patricia L. Morris
*Attorney, Agent, or Firm*—Sprung Horn Kramer & Woods

[57] ABSTRACT

Herbicidal substituted 4,5-diamino-1,2,4-triazol-3-(thi)ones of the formula

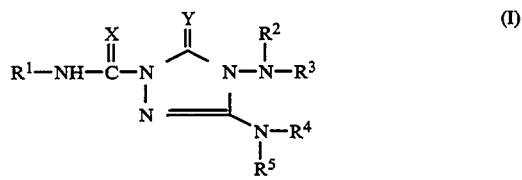

(I)

in which
 $R^1$, $R^2$, $R^3$, $R^4$ and $R^5$ each independently is hydrogen or an organic radical,
 X is O or S, and
 Y is O or S.

There are also provided novel intermediates of the formulae

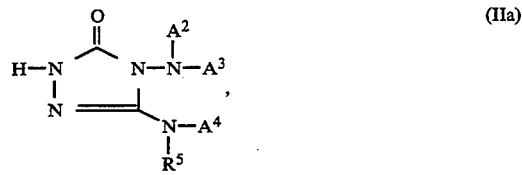

(IIa)

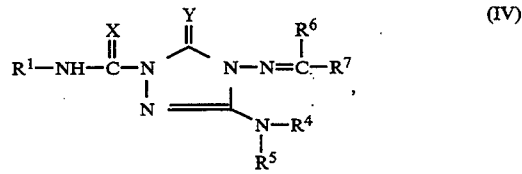

(IV)

(Abstract continued on next page.)

-continued
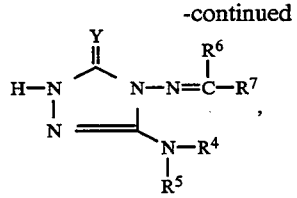 (XXI)
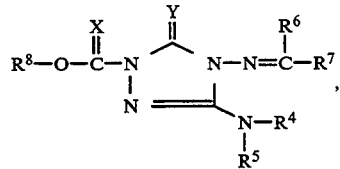 (XXIII)
-continued
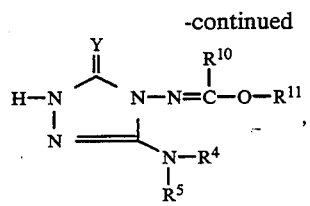 (XXV)
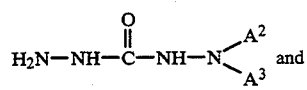 (XIIIa)
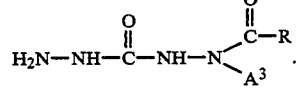 (XIIIb)
2 Claims, No Drawings

HERBICIDAL SUBSTITUTED 4,5-DIAMINO-1,2,4-TRIAZOL-3-(THI)ONES

This application is a divisional of U.S. patent application Ser. No. 07/764,437, filed Sep. 23, 1991, which issued Jun. 15, 1993, as U.S. Pat. No. 5,220,032 which is a divisional of 07/565,293, filed Aug. 9, 1990, issued Jan. 21, 1992, as U.S. Pat. No. 5,082,490 and is a continuation-in-part therethrough of U.S. patent application Ser. No. 07/583,883, filed Sep. 17, 1990, which issued Feb. 18, 1992, as U.S. Pat. No. 5,089,627, which is a division of U.S. patent application Ser. No. 07/382,163, filed on Jul. 19, 1989, which issued as U.S. Pat. No. 4,988,381.

The invention relates to new substituted 4,5-diamino-1,2,4-triazol(e)-3-(thi)ones, to several processes and new intermediates for their preparation, and to their use as herbicides.

It is known that certain substituted triazolones, such as, for example, 4-amino-5-methyl-2-phenylaminocarbonyl-2,4-dihydro-3H-1,2,4-triazol-3-one, have herbicidal properties (cf. EP-A 294,666). However, the herbicidal action of this known compound is not satisfactory in all respects.

New substituted 4,5-diamino-1,2,4-triazol-3-(thi)ones of the general formula (I)

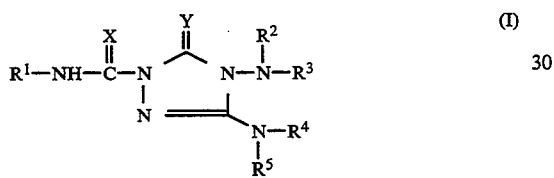

in which

R$^1$ represents hydrogen, alkyl, alkenyl, alkinyl, halogenoalkyl, halogenoalkenyl, halogenoalkinyl, cyanoalkyl, hydroxyalkyl, alkoxyalkyl, aryloxyalkyl, alkoxycarbonylalkyl, alkoxycarbonylalkenyl, alkylaminoalkyl or dialkylaminoalkyl, or represents in each case optionally substituted cycloalkyl, cycloalkylalkyl, cycloalkenyl or cycloalkenylalkyl, or represents optionally substituted heterocyclylalkyl, or represents in each case optionally substituted aralkyl, aroyl, aryl, aralkyloxy or aryloxy, or represents alkoxy, alkenyloxy or alkinyloxy, R$^2$, R$^3$, R$^4$ and R$^5$ are identical or different and independently of one another represent hydrogen, alkyl, alkenyl, alkinyl, halogenoalkyl, halogenoalkenyl, halogenoalkinyl, cyanoalkyl, alkoxyalkyl or alkylthioalkyl, or represent in each case optionally substituted cycloalkyl, cycloalkylalkyl, aryl or aralkyl, or two of these radicals (R$^2$ and R$^3$ or R$^4$ and R$^5$) together represent alkanediyl or oxaalkanediyl, and R$^5$ can also represent alkoxy, X represents oxygen or sulphur, and Y represents oxygen or sulphur, have now been found.

Where appropriate, the compounds of the formula (I) can be present as geometric and/or optical isomers, or mixtures of isomers, of various compositions, depending on the nature of the substituents R$^1$, R$^2$, R$^3$, R$^4$ and R$^5$. The invention claims the pure isomers as well as the mixtures of isomers.

Furthermore, it has been found that the new substituted 4,5-diamino-1,2,4-triazol-3-(thi)ones of the general formula (I)

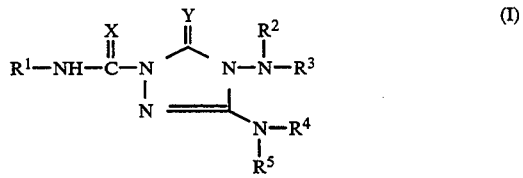

in which

R$^1$ represents hydrogen, alkyl, alkenyl, alkinyl, halogenoalkyl, halogenoalkenyl, halogenoalkinyl, cyanoalkyl, hydroxyalkyl, alkoxyalkyl, aryloxyalkyl, alkoxycarbonylalkyl, alkoxycarbonylalkenyl, alkylaminoalkyl or dialkylaminoalkyl, or represents in each case optionally substituted cycloalkyl, cycloalkylalkyl, cycloalkenyl or cycloalkenylalkyl, or represents optionally substituted heterocyclylalkyl, or represents in each case optionally substituted aralkyl, aroyl, aryl, aralkyloxy or aryloxy, or represents alkoxy, alkenyloxy or alkinyloxy, R$^2$, R$^3$, R$^4$ and R$^5$ are identical or different and independently of one another represent hydrogen, alkyl, alkenyl, alkinyl, halogenoalkyl, halogenoalkenyl, halogenoalkinyl, cyanoalkyl, alkoxyalkyl or alkylthioalkyl, or represent in each case optionally substituted cycloalkyl, cycloalkylalkyl, aryl or aralkyl, or two of these radicals (R$^2$ and R$^3$ or R$^4$ and R$^5$) together represent alkanediyl or oxaalkanediyl, and R$^5$ can also represent alkoxy, X represents oxygen or sulphur, and Y represents oxygen or sulphur, are obtained when (a) 4,5-diamino-1,2,4-triazol-3-(thi)ones of the general formula (II)

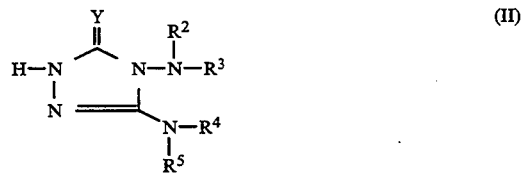

in which

R$^2$, R$^3$, R$^4$, R$^5$ and Y have the abovementioned meanings, are reacted with iso(thio)cyanates of the general formula (III)

in which

R$^1$ and X have the abovementioned meanings, if appropriate in the presence of a diluent and if appropriate in the presence of a reaction auxiliary, or when (b) 4-alkylideneamino-5-amino-1,2,4-triazol-3-(thi)ones of the general formula (IV)

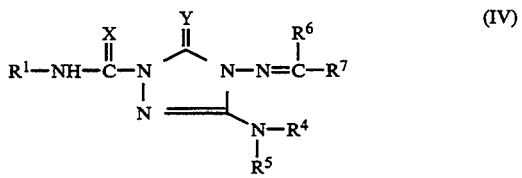

in which

R$^1$, R$^4$, R$^5$, X and Y have the abovementioned meanings and R$^6$ and R$^7$ are identical or different and independently of one another represent hydrogen, alkyl, aralkyl or aryl, are reacted with aqueous acids, if appropriate in the presence of organic solvents,
or when (c) substituted 1,2,4-triazol-3-(thi)ones of the general formula (V)

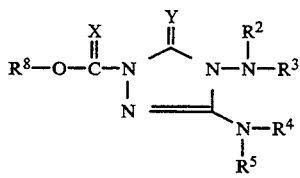

(V)

in which $R^2$, $R^3$, $R^4$, $R^5$, X and Y have the abovementioned meanings and $R^8$ represents alkyl, aralkyl or aryl, are reacted with amino compounds of the general formula (VI)

(VI)

in which $R^1$ has the abovementioned meaning, if appropriate in the presence of a diluent and if appropriate in the presence of a reaction auxiliary, or when (d) 4,5-diamino-1,2,4-triazol-3-(thi)ones of the general formula (II)

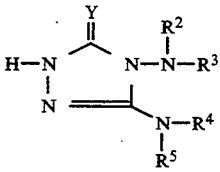

(II)

in which $R^1$, $R^3$, $R^4$, $R^5$ and Y have the abovementioned meanings, are reacted with (thio)urethanes of the general formula (VII)

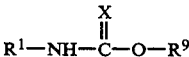

(VII)

in which $R^1$ and X have the abovementioned meanings and $R^9$ represents alkyl, aralkyl or aryl, if appropriate in the presence of a diluent and if appropriate in the presence of a reaction auxiliary, or when (e) 4-oxyalkylideneamino-5-amino-1,2,4-triazol-3-(thi)ones of the general formula (VIII)

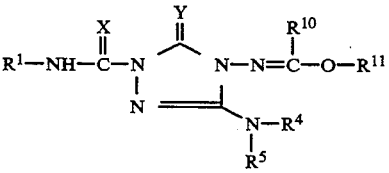

(VIII)

in which $R^1$, $R^4$, $R^5$, X and Y have the abovementioned meanings and $R^{10}$ and $R^{11}$ are identical or different and independently of one another represent alkyl, alkenyl, alkinyl, cycloalkyl, aralkyl or aryl, and $R^{10}$ may also represent hydrogen, are reacted with hydride complexes of the general formula (IX)

(IX)

in which $M^1$ represents lithium, sodium or potassium and $M^2$ represents boron or aluminium, if appropriate in the presence of a diluent, or when (f) 4-alkylideneamino-5-amino-1,2,4-triazol-3-(thi)ones of the general formula (IV)

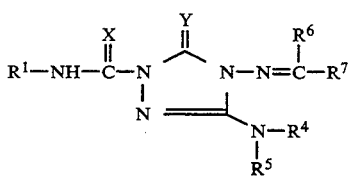

(IV)

in which $R^1$, $R^4$, $R^5$, X and Y have the abovementioned meanings and $R^6$ and $R^7$ are identical or different and independently of one another represent hydrogen, alkyl, aralkyl or aryl, are reacted with reducing agents, if appropriate in the presence of catalysts and if appropriate in the presence of diluents.

Finally, it has been found that the new substituted 4,5-diamino-1,2,4-triazol-3-ones of the general formula (I) have interesting herbicidal properties.

Surprisingly, the substituted 4,5-diamino-1,2,4-triazol-3-ones of the general formula (I) according to the invention show a considerably more powerful herbicidal action against problem weeds than the compound 4-amino-5-methyl-2-phenylaminocarbonyl-2,4-dihydro-3H-1,2,4-triazol-3-one, which has a similar structure and profile of action.

The aromatic radicals in the definitions, such as, for example, aryl, aryloxy or aralkyl, preferably represent phenyl or naphthyl, in particular phenyl. Unless expressly stated otherwise, the aliphatic carbon chains are in each case straight-chain or branched.

The substituent heterocyclylalkyl in $R^1$ preferably denotes heterocyclylalkyl having 1 to 6 carbon atoms in the straight-chain or branched alkyl moiety and 2 to 9 carbon atoms as well as 1 to 3 hetero atoms—in particular nitrogen, oxygen and/or sulphur—in the heterocyclyl moiety, it being possible for the heterocyclyl moiety to be monosubstituted or polysubstituted, in particular monosubstituted, bisubstituted or trisubstituted, by identical or different substituents from amongst halogen, cyano and nitro as well as $C_1$-$C_5$-alkyl, $C_1$-$C_5$-alkoxy, $C_1$-$C_5$-alkylthio, halogeno-$C_1$-$C_5$-alkyl, halgeno-$C_1$-$C_5$-alkoxy, halogeno-$C_1$-$C_5$-alkylthio or $C_1$-$C_5$-alkoxycarbonyl. In particular, the heterocyclyl moiety can be substituted by fluorine, chlorine, cyano, nitro, methyl, ethyl, n- or i-propyl, n-, i-, s- or t-butyl, methoxy, ethoxy, methylthio, trifluoromethyl, trifluoromethoxy or trifluoromethylthio. The substituent heterocyclylalkyl in $R^1$ particularly preferably represents heterocycylmethyl, heterocyclylpropyl or heterocyclylethyl, each of which is optionally monosubstituted to trisubstituted in the heterocyclyl moiety by identical or different substituents, suitable heterocycles in each case being:

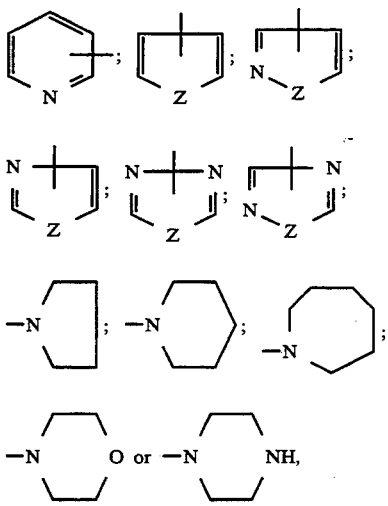

Z in each case representing oxygen or sulphur and suitable substituents in each case being: fluorine, chlorine, bromine, cyano, nitro, methyl, ethyl, n- or i-propyl, n-, i-, s- or t-butyl, methoxy, ethoxy, methylthio, trifluoromethyl, trifluoromethoxy or trifluoromethylthio.

Formula (I) provides a general definition of the substituted 4,5-diamino-1,2,4-triazol-3-(thi)ones according to the invention. Preferred compounds of the formula (I) are those in which $R^1$ represents hydrogen, or represents in each case straight-chain or branched alkyl having 1 to 18 carbon atoms, alkenyl having 2 to 8 carbon atoms, alkinyl having 2 to 8 carbon atoms, halogenoalkyl having 1 to 8 carbon atoms and 1 to 17 identical or different halogen atoms, halogenoalkenyl or halogenoalkinyl, in each case having 2 to 8 carbon atoms and 1 to 15, or 13, identical or different halogen atoms, cyanoalkyl having 1 to 8 carbon atoms or hydroxyalkyl having 1 to 8 carbon atoms and 1 to 6 hydroxyl groups, or represents phenoxyalkyl having 1 to 4 carbon atoms in the alkyl moiety, alkoxyalkyl, alkoxycarbonylalkyl or alkoxycarbonylalkenyl, in each case having up to 6 carbon atoms in the individual alkyl or alkenyl moieties, or alkylaminoalkyl or dialkylaminoallkyl, in each case having 1 to 6 carbon atoms in the individual alkyl moieties, or represents cycloalkyl, cycloalkylalkyl, cycloalkyl or cycloalkenylalkyl, each of which has 3 to 8 carbon atoms in the cycloalkyl or cycloalkenyl moiety and where appropriate 1 to 6 carbon atoms in the alkyl moiety and each of which is optionally monosubstituted to trisubstituted by identical or different substituents, suitable substituents in each case being: halogen, cyano as well as in each case straight-chain or branched alkyl or halogenoalkyl, in each case having 1 to 4 carbon atoms and where appropriate 1 to 9 identical or different halogen atoms, and straight-chain or branched halogenoalkenyl having up to 4 carbon atoms and 1 to 5 identical or different halogen atoms, or in each case double-linked alkanediyl or alkenediyl, in each case having up to 4 carbon atoms; $R^1$ furthermore represents heterocyclylalkyl which has 1 to 6 carbon atoms in the straight-chain or branched alkyl moiety and 2 to 9 carbon atoms as well as 1 to 3 hetero atoms—in particular nitrogen, oxygen and/or sulphur—in the heterocyclyl moiety and which is optionally monosubstituted to the substituted in the heterocyclyl moiety by identical or different substituents, suitable substituents being: halogen, cyano, nitro, as well as in each case straight-chain or branched alkyl, alkoxy, alkylthio, halogenoalkyl, halogenoalkoxy, halogenoalkylthio or alkoxycarbonyl, in each case having 1 to 5 carbon atoms and where appropriate 1 to 9 identical or different halogen atoms; $R^1$ furthermore represents in each case straight-chain or branched alkoxy having 1 to 8 carbon atoms, alkenyloxy having 2 to 8 carbon atoms or alkinyloxy having 2 to 8 carbon, atoms, or represents aralkyl, aroyl, aryl, aralkyloxy or aryloxy, each of which has 6 to 10 carbon atoms in the aryl moiety and where appropriate 1 to 8 carbon atoms in the straight-chain or branched alkyl moiety and each of which is optionally monosubstituted to trisubstituted by identical or different substituents, suitable alkyl substituents, where appropriate, being halogen and cyano and suitable aryl substituents in each case being: halogen, cyano, nitro, hydroxyl, in each case straight-chain or branched alkyl, alkoxy, alkylthio, halogenoalkyl, halogenoalkoxy, halogenoalkylthio, alkylsulphinyl, alkylsulphonyl, halogenoalkylsulphinyl, halogenoalkylsulphonyl, alkanoyl or alkoxycarbonyl, in each case having 1 to 6 carbon atoms in the alkyl moiety and, where appropriate, 1 to 9 identical or different halogen atoms, or cycloalkyl having 3 to 6 carbon atoms, and phenoxy; or $R^1$ represents benzyl with an —O—CH$_2$—O— group fused to the phenyl moiety, $R^2$, $R^3$, and $R^5$ are identical or different and independently of one another represent hydrogen, or represent in each case straight-chain or branched alkyl having 1 to 8 carbon atoms, alkenyl having 2 to 8 carbon atoms, alkinyl having 2 to 8 carbon atoms, halogenoalkyl having 1 to 8 carbon atoms and 1 to 17 identical or different halogen atoms, halogenoalkenyl or halogenoalkinyl, in each -case having 2 to 8 carbon atoms and 1 to 15, or 13, identical or different halogen atoms, cyanoalkyl having 1 to 8 carbon atoms, or alkoxyalkyl or alkylthioalkyl, in each case having up to 4 carbon atoms in the individual alkyl moieties, or represent cycloalkyl or cycloalkylalkyl, each of which has 3 to 8 carbon atoms in the cycloalkyl moiety and, where appropriate, 1 to 6 carbon atoms in the alkyl moiety and each of which is optionally monosubstituted to trisubstituted by identical or different substituents, suitable substituents in each case being: halogen, cyano as well as in each case straight-chain or branched alkyl or halogenoalkyl, in each case having 1 to 4 carbon atoms and, where appropriate, 1 to 9 identical or different halogen atoms, the radicals $R^2$ to $R^5$ furthermore represent aryl or aralkyl, each of which has 6 or 10 carbon atoms in the aryl moiety and, where appropriate, 1 to 4 carbon atoms in the straight-chain or branched alkyl moiety and each of which is optionally monosubstituted to trisubstituted by identical or different substituents, suitable substituents in each case being: halogen, cyano, nitro, hydroxyl, in each case straight-chain or branched alkyl, alkoxy, alkylthio, halogenoalkyl, halogenoalkoxy, halogenoalkylthio, alkylsulphinyl, alkylsulphonyl, halogenoalkylsulphinyl, halogenoalkylsulphonyl, alkanoyl or alkoxycarbonyl, in each case having 1 to 6 carbon atoms in the alkyl moiety and, where appropriate, 1 to 9 halogen atoms, it is furthermore also possible for two of these radicals together—$R^2$ and $R^3$ or $R^4$ and $R^5$—to represent straight-chain or branched alkanedlyl or oxaalkanediyl having 2 to 6 carbon atoms, and $R^5$ can also represent straight-chain or branched alkoxy having 1 to 8 carbon atoms, X represents oxygen or sulphur and
Y represents oxygen or sulphur.

Particularly preferred compounds of the formula (I) are those in which $R^1$ represents hydrogen, methyl, ethyl, n- or i-propyl, n-, i-, s- or t-butyl, in each case straight-chain or branched pentyl, hexyl, heptyl, octyl, nonyl, decyl, or dodecyl, or represents allyl, in each case straight-chain or branched butenyl, pentenyl or hexenyl, propargyl, in each case straight-chain or branched butinyl, pentinyl or hexinyl, or represents straight-chain or branched halogenoalkyl having 1 to 8 carbon atoms and 1 to 9 identical or different halogen atoms, in particular fluorine, chlorine or bromine, or represents in each case straight-chain or branched halogenoalkenyl or halogenoalkinyl, in each case having 3 to 8 carbon atoms and 1 to 3 halogen atoms, in particular fluorine or chlorine, or represents in each case straight-chain or branched cyanoalkyl having 1 to 6 carbon atoms in the alkyl moiety, hydroxyalkyl having 1 to 6 carbon atoms and 1 to 3 hydroxyl groups, alkoxyalkyl, alkoxycarbonylalkyl or alkoxycarbonylalkenyl, alkylaminoalkyl or dialkylaminoalkyl, in each case having up to 4 carbon atoms in the individual alkyl or alkenyl moieties, or represents cyclopropyl, cyclopropylmethyl, cyclopropylethyl, cyclopentyl, cyclohexyl, cycloheptyl, cyclooctyl, cyclohexylmethyl, cyclohexylethyl, cyclohexenyl or cyclohexenylmethyl, each of which is optionally monosubstituted to trisubstituted by identical or different substituents, suitable substituents in each case being: fluorine, chlorine, bromine, methyl, ethyl, n- or i-propyl, n-, i-, s- or t-butyl, cyano, methanediyl, ethanediyl, butanediyl or butadienediyl or dichloroallyl;

$R^1$ furthermore represents heterocyclylmethyl, heterocyclylpropyl or heterocyclylethyl, each of which is optionally monosubstituted to trisubstituted in the heterocyclyl moiety by identical or different substituents, suitable heterocycles in each case being:

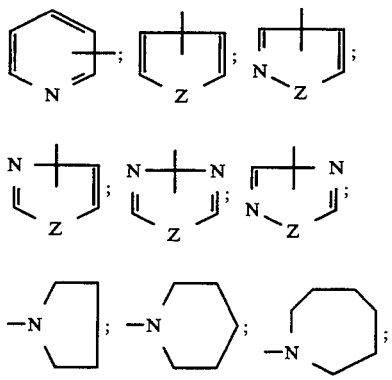

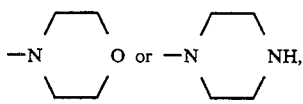

Z in each case representing oxygen or sulphur and suitable substituents in each case being: fluorine, chlorine, bromine, cyano, nitro, methyl, ethyl, n- or i-propyl, n-, i-, s- or t-butyl, methoxy, ethoxy, methylthio, trifluoromethyl, trifluoromethoxy or trifluoromethylthio;

$R^1$ furthermore represents in each case straight-chain or branched alkoxy having 1 to 6 carbon atoms, alkenyloxy having 3 to 6 carbon atoms or alkinyloxy having 3 to 6 carbon atoms, or represents benzyl, phenylethyl, phenylpropyl, phenylbutyl, phenylpentyl, phenylhexyl, phenylheptyl, phenylcyanomethyl, phenylcyanoethyl, phenylcyanopropyl, benzyloxy, phenylethyloxy, phenoxy, benzoyl, phenyl or naphthyl, where appropriate straight-chain or branched, each of which is optionally monosubstituted to trisubstituted by identical or different substituents, suitable phenyl substituents in each case being: fluorine, chlorine, bromine, hydroxyl, cyano, nitro, methyl, ethyl, n- or i-propyl, n-, i-, s- or t-butyl, methoxy, ethoxy, methylthio, trifluoromethyl, trifluoromethoxy, trifluoromethylthio, trifluoromethylsulphinyl, trifluoromethylsulphonyl, methylsulphinyl, methylsulphonyl, acetyl, propionyl, methoxycarbonyl, ethoxycarbonyl, cyclohexyl or phenoxy, $R^2$ represents hydrogen, methyl, ethyl, propyl, isopropyl, butyl, isobutyl, sec-butyl, allyl, propargyl, cyanoethyl, methoxyethyl, cyclopropyl, cyclopentyl, cyclohexyl, phenyl or benzyl, $R^3$ represents hydrogen, methyl, ethyl, propyl, butyl, allyl, propargyl, cyanoethyl, methoxyethyl or optionally chlorine-substituted benzyl, or together with $R^2$ represents butane-1,4-diyl or pentane, 1,5-diyl, $R^4$ represents hydrogen, methyl, ethyl, propyl, isopropyl, butyl, isobutyl, sec-butyl, allyl, propargyl, cyanoethyl, methoxyethyl, cyclopropyl, cyclopentyl, cyclohexyl, phenyl or benzyl, $R^5$ represents hydrogen, methyl, ethyl, propyl, butyl, allyl, propargyl, cyanoethyl, methoxyethyl, methoxy or benzyl, or together with $R^4$ represents butane-1,4-diyl, pentane-1,5-diyl or 3-oxa-pentane-1,5-diyl, X represents oxygen or sulphur and
Y represents oxygen or sulphur.

In all definitions, particular mention should be made of the meanings below, where $R^2$ represents hydrogen,
$R^3$ represents hydrogen or methyl,
$R^4$ represents hydrogen, methyl or ethyl,
$R^5$ represents hydrogen, methyl, ethyl, n- or isopropyl, or $R^4$ and $R^5$ together represent butane-1,4-diyl, X represents oxygen or sulphur, and
Y represents oxygen.

Examples of the compounds of the formula (I) are listed in Table 1 below.

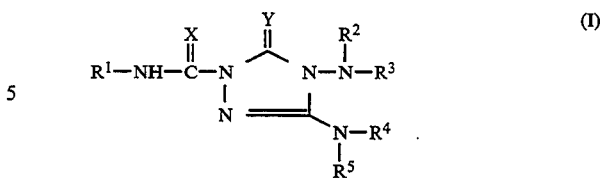

(I)

TABLE 1

| Examples of the compounds of the formula (I) | | | | | | |
|---|---|---|---|---|---|---|
| R¹ | R² | R³ | R⁴ | R⁵ | X | Y |
| $(CH_3)_3C-$ | H | H | H | $CH_3$ | O | O |
| $ClCH_2-C(CH_3)_2-$ | H | H | H | $CH_3$ | O | O |
| $FCH_2-C(CH_3)_2-$ | H | H | H | $CH_3$ | O | O |
| $(CH_3)_2CH-$ | H | H | H | $CH_3$ | O | O |
| $Cl-CH_2-CH(CH_3)-$ | H | H | H | $CH_3$ | O | O |
| $C_2H_5CH(CH_3)-$ | H | H | H | $CH_3$ | O | O |
| ⌬–O–CH₂–CH(CH₃)– | H | H | H | $CH_3$ | O | O |
| cyclohexyl- | H | H | H | $CH_3$ | O | O |
| cyclopentyl- | H | H | H | $CH_3$ | O | O |
| cyclopropyl- | H | H | H | $CH_3$ | O | O |
| $(CH_3)_2CH-CH(CH_3)-$ | H | H | H | $CH_3$ | O | O |
| $(CH_3)_2CH-CH_2-CH(CH_3)-$ | H | H | H | $CH_3$ | | |
| ⌬–CH(CH₃)– | H | H | H | $CH_3$ | O | O |
| ⌬–C(CH₃)₂– | H | H | H | $CH_3$ | O | O |
| $C_4H_9$ | H | H | H | $CH_3$ | O | O |
| $C_2H_5-C(CH_3)_2-$ | H | H | H | $CH_3$ | O | O |
| $C_3H_7-C(CH_3)_2-$ | H | H | H | $CH_3$ | O | O |
| $(CH_3)_2CH-C(CH_3)_2-$ | H | H | H | $CH_3$ | O | O |
| $HC\equiv C-C(CH_3)_2-$ | H | H | H | $CH_3$ | O | O |
| $(CH_3)_3C$–⌬– | H | H | H | $CH_3$ | O | O |
| $C(CH_3)_3-$ | H | H | H | $CH_3$ | O | O |
| $C(CH_3)_3-$ | H | H | H | $CH_3$ | S | O |
| $C(CH_3)_3-$ | H | H | H | $CH_3$ | S | S |
| $ClCH_2-C(CH_3)_2-$ | H | H | H | $CH_3$ | S | O |
| $(CH_3)_3C-$ | H | H | H | $C_2H_5$ | O | O |
| $ClCH_2-C(CH_3)_2-$ | H | H | H | $C_2H_5$ | O | O |
| $FCH_2-C(CH_3)_2-$ | H | H | H | $C_2H_5$ | O | O |
| $(CH_3)_2CH-$ | H | H | H | $C_2H_5$ | O | O |
| $Cl-CH_2-CH(CH_3)-$ | H | H | H | $C_2H_5$ | O | O |

TABLE 1-continued

Examples of the compounds of the formula (I)

| R¹ | R² | R³ | R⁴ | R⁵ | X | Y |
|---|---|---|---|---|---|---|
| $C_2H_5CH(CH_3)-$ | H | H | H | $C_2H_5$ | O | O |
| 4-phenoxy-$CH_2-CH(CH_3)-$ (PhO-CH₂-CH(CH₃)-) | H | H | H | $C_2H_5$ | O | O |
| cyclohexyl-(H)- | H | H | H | $C_2H_5$ | O | O |
| cyclopentyl- | H | H | H | $C_2H_5$ | O | O |
| cyclopropyl- | H | H | H | $C_2H_5$ | O | O |
| $(CH_3)_2CH-CH(CH_3)-$ | H | H | H | $C_2H_5$ | O | O |
| $(CH_3)_2CH-CH_2-CH(CH_3)-$ | H | H | H | $C_2H_5$ | O | O |
| Ph-$CH(CH_3)-$ | H | H | H | $C_2H_5$ | O | O |
| Ph-$C(CH_3)_2-$ | H | H | H | $C_2H_5$ | O | O |
| $C_4H_9$ | H | H | H | $C_2H_5$ | O | O |
| $C_2H_5-C(CH_3)_2-$ | H | H | H | $C_2H_5$ | O | O |
| $C_3H_7-C(CH_3)_2-$ | H | H | H | $C_2H_5$ | O | O |
| $(CH_3)_2CH-C(CH_3)_2-$ | H | H | H | $C_2H_5$ | O | O |
| $HC\equiv C-C(CH_3)_2-$ | H | H | H | $C_2H_5$ | O | O |
| 4-$(CH_3)_3C$-C₆H₄- | H | H | H | $C_2H_5$ | O | O |
| $C(CH_3)_3-$ | H | H | H | $C_2H_5$ | O | S |
| $C(CH_3)_3-$ | H | H | H | $C_2H_5$ | S | O |
| $C(CH_3)_3-$ | H | H | H | $C_2H_5$ | S | S |
| $ClCH_2-C(CH_3)_2-$ | H | H | H | $C_2H_5$ | S | O |
| $(CH_3)_3C-$ | H | H | H | $C_3H_7$ | O | O |
| $ClCH_2-C(CH_3)_2-$ | H | H | H | $C_3H_7$ | O | O |
| $FCH_2-C(CH_3)_2-$ | H | H | H | $C_3H_7$ | O | O |
| $(CH_3)_2CH-$ | H | H | H | $C_3H_7$ | O | O |
| $Cl-CH_2-CH(CH_3)-$ | H | H | H | $C_3H_7$ | O | O |
| $C_2H_5CH(CH_3)-$ | H | H | H | $C_3H_7$ | O | O |
| 4-phenoxy-$CH_2-CH(CH_3)-$ (PhO-CH₂-CH(CH₃)-) | H | H | H | $C_3H_7$ | O | O |
| cyclohexyl-(H)- | H | H | H | $C_3H_7$ | O | O |
| cyclopentyl- | H | H | H | $C_3H_7$ | O | O |
| cyclopropyl- | H | H | H | $C_3H_7$ | O | O |

TABLE 1-continued

Examples of the compounds of the formula (I)

| $R^1$ | $R^2$ | $R^3$ | $R^4$ | $R^5$ | X | Y |
|---|---|---|---|---|---|---|
| $(CH_3)_2CH-CH(CH_3)-$ | H | H | H | $C_3H_7$ | O | O |
| $(CH_3)_2CH-CH_2-CH(CH_3)-$ | H | H | H | $C_3H_7$ | O | O |
| 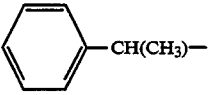 | H | H | H | $C_3H_7$ | O | O |
| 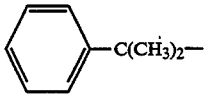 | H | H | H | $C_3H_7$ | O | O |
| $C_4H_9$ | H | H | H | $C_3H_7$ | O | O |
| $C_2H_5-C(CH_3)_2-$ | H | H | H | $C_3H_7$ | O | O |
| $C_3H_7-C(CH_3)_2-$ | H | H | H | $C_3H_7$ | O | O |
| $(CH_3)_2CH-C(CH_3)_2-$ | H | H | H | $C_3H_7$ | O | O |
| $HC{\equiv}C-C(CH_3)_2-$ | | | | | | |
| 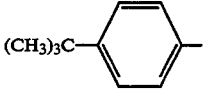 | H | H | H | $C_3H_7$ | O | O |
| $C(CH_3)_3-$ | H | H | H | $C_3H_7$ | O | S |
| $C(CH_3)_3-$ | H | H | H | $C_3H_7$ | S | O |
| $C(CH_3)_3-$ | H | H | H | $C_3H_7$ | S | S |
| $ClCH_2-C(CH_3)_2-$ | H | H | H | $C_3H_7$ | S | O |
| $(CH_3)_3C-$ | H | H | H | $(CH_3)_2CH$ | O | O |
| $ClCH_2-C(CH_3)_2-$ | H | H | H | $(CH_3)_2CH$ | O | O |
| $FCH_2-C(CH_3)_2-$ | H | H | H | $(CH_3)_2CH$ | O | O |
| $(CH_3)_2CH-$ | H | H | H | $(CH_3)_2CH$ | O | O |
| $Cl-CH_2-CH(CH_3)-$ | H | H | H | $(CH_3)_2CH$ | O | O |
| $C_2H_5CH(CH_3)-$ | H | H | H | $(CH_3)_2CH$ | O | O |
| 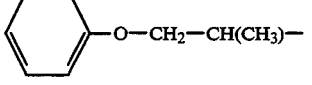 | H | H | H | $(CH_3)_2CH$ | O | O |
| 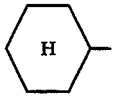 | H | H | H | $(CH_3)_2CH$ | O | O |
| 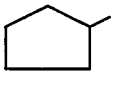 | H | H | H | $(CH_3)_2CH$ | O | O |
|  | H | H | H | $(CH_3)_2CH$ | O | O |
| $(CH_3)_2CH-CH(CH_3)-$ | H | H | H | $(CH_3)_2CH$ | O | O |
| $(CH_3)_2CH-CH_2-CH(CH_3)-$ | H | H | m | $(CH_3)_2CH$ | O | O |
| 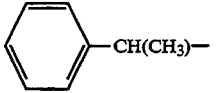 | H | H | H | $(CH_3)_2CH$ | O | O |
| 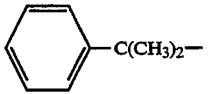 | H | H | H | $(CH_3)_2CH$ | O | O |
| $C_4H_9$ | H | H | H | $(CH_3)_2CH$ | O | O |
| $C_2H_5-C(CH_3)_2-$ | H | H | H | $(CH_3)_2CH$ | O | O |
| $C_3H_7-C(CH_3)_2-$ | H | H | H | $(CH_3)_2CH$ | O | O |
| $(CH_3)_2CH-C(CH_3)_2-$ | H | H | H | $(CH_3)_2CH$ | O | O |
| $HC{\equiv}C-C(CH_3)_2-$ | H | H | H | $(CH_3)_2CH$ | O | O |

TABLE 1-continued

Examples of the compounds of the formula (I)

| R¹ | R² | R³ | R⁴ | R⁵ | X | Y |
|---|---|---|---|---|---|---|
| (CH₃)₃C—⟨phenyl⟩— | H | H | H | (CH₃)₂CH | O | O |
| C(CH₃)₃— | H | H | H | (CH₃)₂CH | O | S |
| C(CH₃)₃— | H | H | H | (CH₃)₂CH | S | O |
| C(CH₃)₃— | H | H | H | (CH₃)₂CH | S | S |
| ClCH₂—C(CH₃)₂— | H | H | H | (CH₃)₂CH | S | O |
| (CH₃)₃C— | H | H | CH₃ | CH₃ | O | O |
| ClCH₂—C(CH₃)₂— | H | H | CH₃ | CH₃ | O | O |
| FCH₂—C(CH₃)₂— | H | H | CH₃ | CH₃ | O | O |
| (CH₃)₂CH— | H | H | CH₃ | CH₃ | O | O |
| Cl—CH₂—CH(CH₃)— | H | H | CH₃ | CH₃ | O | O |
| C₂H₅CH(CH₃)— | H | H | CH₃ | CH₃ | O | O |
| ⟨phenyl⟩—O—CH₂—CH(CH₃)— | H | H | CH₃ | CH₃ | O | O |
| ⟨cyclohexyl⟩H— | H | H | CH₃ | CH₃ | O | O |
| ⟨cyclopentyl⟩— | H | H | CH₃ | CH₃ | O | O |
| ⟨cyclopropyl⟩— | H | H | CH₃ | CH₃ | O | O |
| (CH₃)₂CH—CH(CH₃)— | H | H | CH₃ | CH₃ | O | O |
| (CH₃)₂CH—CH₂—CH(CH₃)— | H | H | CH₃ | CH₃ | O | O |
| ⟨phenyl⟩—CH(CH₃)— | H | H | CH₃ | CH₃ | O | O |
| ⟨phenyl⟩—C(CH₃)₂— | H | H | CH₃ | CH₃ | O | O |
| C₄H₉ | H | H | CH₃ | CH₃ | O | O |
| C₂H₅—C(CH₃)₂— | H | H | CH₃ | CH₃ | O | O |
| C₃H₇—C(CH₃)₂— | H | H | CH₃ | CH₃ | O | O |
| (CH₃)₂CH—C(CH₃)₂— | H | H | CH₃ | CH₃ | O | O |
| HC≡C—C(CH₃)₂— | H | H | CH₃ | CH₃ | O | O |
| (CH₃)₃C—⟨phenyl⟩— | H | H | CH₃ | CH₃ | O | O |
| C(CH₃)₃— | H | H | CH₃ | CH₃ | O | S |
| C(CH₃)₃— | H | H | CH₃ | CH₃ | S | O |
| C(CH₃)₃— | H | H | CH₃ | CH₃ | S | S |
| ClCH₂—C(CH₃)₂— | H | H | CH₃ | CH₃ | S | O |
| (CH₃)₃C— | H | H | CH₃ | C₂H₅ | O | O |
| ClCH₂—C(CH₃)₂— | H | H | CH₃ | C₂H₅ | O | O |
| FCH₂—C(CH₃)₂— | H | H | CH₃ | C₂H₅ | O | O |
| (CH₃)₂CH— | H | H | CH₃ | C₂H₅ | O | O |
| Cl—CH₂—CH(CH₃)— | H | H | CH₃ | C₂H₅ | O | O |
| C₂H₅CH(CH₃)— | H | M. | CH₃ | C₂H₅ | O | O |
| ⟨phenyl⟩—O—CH₂—CH(CH₃)— | H | H | CH₃ | C₂H₅ | O | O |

TABLE 1-continued

Examples of the compounds of the formula (I)

| R¹ | R² | R³ | R⁴ | R⁵ | X | Y |
|---|---|---|---|---|---|---|
| cyclohexyl-H | H | H | CH₃ | C₂H₅ | O | O |
| cyclopentyl- | H | H | CH₃ | C₂H₅ | O | O |
| cyclopropyl- | H | H | CH₃ | C₂H₅ | O | O |
| (CH₃)₂CH—CH(CH₃)— | H | H | CH₃ | C₂H₅ | O | O |
| (CH₃)₂CH—CH₂—CH(CH₃)— | H | H | CH₃ | C₂H₅ | O | O |
| phenyl-CH(CH₃)— | H | H | CH₃ | C₂H₅ | O | O |
| phenyl-C(CH₃)₂— | H | H | CH₃ | C₂H₅ | O | O |
| C₄H₉ | H | H | CH₃ | C₂H₅ | O | O |
| C₂H₅—C(CH₃)₂— | H | H | CH₃ | C₂H₅ | O | O |
| C₃H₇—C(CH₃)₂— | H | H | CH₃ | C₂H₅ | O | O |
| (CH₃)₂CH—C(CH₃)₂— | H | H | CH₃ | C₂H₅ | O | O |
| HC≡C—C(CH₃)₂— | H | H | CH₃ | C₃H₇ | O | O |
| (CH₃)₃C-p-phenyl- | H | H | CH₃ | C₂H₅ | O | O |
| (CH₃)₃— | H | H | CH₃ | C₂H₅ | O | S |
| C(CH₃)₃— | H | H | CH₃ | C₂H₅ | S | O |
| C(CH₃)₃— | H | H | CH₃ | C₂H₅ | S | S |
| ClCH₂—C(CH₃)₂— | H | H | CH₃ | C₂H₅ | S | O |
| (CH₃)₃C— | H | H | CH₃ | C₃H₇ | O | O |
| ClCH₂—C(CH₃)₂— | H | H | CH₃ | C₃H₇ | O | O |
| FCH₂—C(CH₃)₂— | H | H | CH₃ | C₃H₇ | O | O |
| (CH₃)₂CH— | H | H.. | CH₃ | C₃H₇ | O | O |
| Cl—CH₂—CH(CH₃)— | H | H | CH₃ | C₃H₇ | O | O |
| C₂H₅CH(CH₃)— | H | H | CH₃ | C₃H₇ | O | O |
| phenyl-O—CH₂—CH(CH₃)— | H | H | CH₃ | C₃H₇ | O | O |
| cyclohexyl-H | H | H | CH₃ | C₃H₇ | O | O |
| cyclopentyl- | H | H | CH₃ | C₃H₇ | O | O |
| cyclopropyl- | H | H | CH₃ | C₃H₇ | O | O |
| (CH₃)₂CH—CH(CH₃)— | H | H | CH₃ | C₃H₇ | O | O |
| (CH₃)₂CH—CH₂—CH(CH₃)— | H | H | CH₃ | C₃H₇ | O | O |
| phenyl-CH(CH₃)— | H | H | CH₃ | C₃H₇ | O | O |

TABLE 1-continued

Examples of the compounds of the formula (I)

| R¹ | R² | R³ | R⁴ | R⁵ | X | Y |
|---|---|---|---|---|---|---|
| 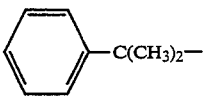 C₆H₅-C(CH₃)₂- | H | H | CH₃ | C₃H₇ | O | O |
| C₄H₉ | H | H | CH₃ | C₃H₇ | O | O |
| C₂H₅—C(CH₃)₂— | H | H | CH₃ | C₃H₇ | O | O |
| C₃H₇—C(CH₃)₂— | H | H | CH₃ | C₃H₇ | O | O |
| (CH₃)₂CH—C(CH₃)₂— | H | CH | C₃H₇ | O | O | |
| HC≡C—C(CH₃)₂— | H | H | CH₃ | C₃H₇ | O | O |
| 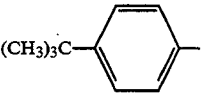 (CH₃)₃C—C₆H₄— | H | H | CH₃ | C₃H₇ | O | O |
| C(CH₃)₃— | H | H | CH₃ | C₃H₇ | O | S |
| C(CH₃)₃— | H | H | CH₃ | C₃H₇ | S | O |
| C(CH₃)₃— | H | H | CH₃ | C₃H₇ | S | S |
| ClCH₂—C(CH₃)₂— | H | H | CH₃ | C₃H₇ | S | O |
| (CH₃)₃C— | H | H | CH₃ | (CH₃)₂CH | O | O |
| ClCH₂—C(CH₃)₂— | H | H | CH₃ | (CH₃)₂CH | O | O |
| FCH₂—C(CH₃)₂— | H | H | CH₃ | (CH₃)₂CH | O | O |
| (CH₃)₂CH— | H | H | CH₃ | (CH₃)₂CH | O | O |
| Cl—CH₂—CH(CH₃)— | H | H | CH₃ | (CH₃)₂CH | O | O |
| C₂H₅CH(CH₃)— | H | H | CH₃ | (CH₃)₂CH | O | O |
| 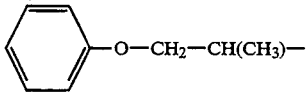 C₆H₅—O—CH₂—CH(CH₃)— | H | H | CH₃ | (CH₃)₂CH | O | O |
| 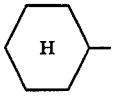 cyclohexyl- | H | H | CH₃ | (CH₃)₂CH | O | O |
| 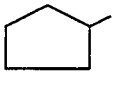 cyclopentyl- | H | H | CH₃ | (CH₃)₂CH | O | O |
|  cyclopropyl- | H | H | CH₃ | (CH₃)₂CH | O | O |
| (CH₃)₂CH—CH(CH₃)— | H | H | CH₃ | (CH₃)₂CH | O | O |
| (CH₃)₂CH—CH₂—CH(CH₃)— | H | H | CH₃ | (CH₃)₂CH | O | O |
| 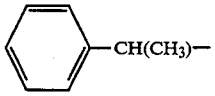 C₆H₅—CH(CH₃)— | H | H | CH₃ | (CH₃)₂CH | O | O |
| 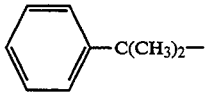 C₆H₅—C(CH₃)₂— | H | H | CH₃ | (CH₃)₂CH | O | O |
| C₄H₉ | H | H | CH₃ | (CH₃)₂CH | O | O |
| C₂H₅—C(CH₃)₂— | H | H | CH₃ | (CH₃)₂CH | O | O |
| C₃H₇—C(CH₃)₂— | H | H | CH₃ | (CH₃)₂CH | O | O |
| (CH₃)₂CH—C(CH₃)₂— | H | H | CH₃ | (CH₃)₂CH | O | O |
| HC≡C—C(CH₃)₂— | H | H | CH₃ | (CH₃)₂CH | O | O |
| 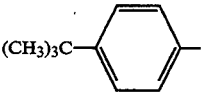 (CH₃)₃C—C₆H₄— | H | H | CH₃ | (CH₃)₂CH | O | O |
| C(CH₃)₃— | H | H | CH₃ | (CH₃)₂CH | O | S |
| C(CH₃)₃— | H | H | CH₃ | (CH₃)₂CH | S | O |
| C(CH₃)₃— | H | H | CH₃ | (CH₃)₂CH | S | S |

TABLE 1-continued

Examples of the compounds of the formula (I)

| R¹ | R² | R³ | R⁴ | R⁵ | X | Y |
|---|---|---|---|---|---|---|
| ClCH$_2$—C(CH$_3$)$_2$— | H | H | CH$_3$ | (CH$_3$)$_2$CH | S | O |
| (CH$_3$)$_3$C— | H | H | C$_2$H$_5$ | C$_2$H$_5$ | O | O |
| ClCH$_2$—C(CH$_3$)$_2$— | H | H | C$_2$H$_5$ | C$_2$H$_5$ | O | O |
| FCH$_2$—C(CH$_3$)$_2$— | H | H | C$_2$H$_5$ | C$_2$H$_5$ | O | O |
| (CH$_3$)$_2$CH— | H | H | C$_2$H$_5$ | C$_2$H$_5$ | O | O |
| Cl—CH$_2$—CH(CH$_3$)— | H | H | C$_2$H$_5$ | C$_2$H$_5$ | O | O |
| C$_2$H$_5$CH(CH$_3$)— | H | H | C$_2$H$_5$ | C$_2$H$_5$ | O | O |
| 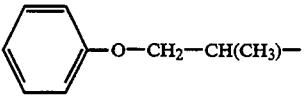 | H | H | C$_2$H$_5$ | C$_2$H$_5$ | O | O |
| 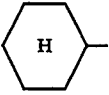 | H | H | C$_2$H$_5$ | C$_2$H$_5$ | O | O |
| 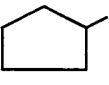 | H | H | C$_2$H$_5$ | C$_2$H$_5$ | O | O |
|  | H | H | C$_2$H$_5$ | C$_2$H$_5$ | O | O |
| (CH$_3$)$_2$CH—CH(CH$_3$)— | H | H | C$_2$H$_5$ | C$_2$H$_5$ | O | O |
| (CH$_3$)$_2$CH—CH$_2$—CH(CH$_3$)— | H | H | C$_2$H$_5$ | C$_2$H$_5$ | O | O |
| 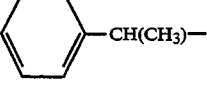 | H | H | C$_2$H$_5$ | C$_2$H$_5$ | O | O |
| 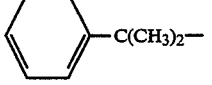 | H | H | C$_2$H$_5$ | C$_2$H$_5$ | O | O |
| C$_4$H$_9$ | H | H | C$_2$H$_5$ | C$_2$H$_5$ | O | O |
| C$_2$H$_5$—C(CH$_3$)$_2$— | H | H | C$_2$H$_5$ | C$_2$H$_5$ | O | O |
| C$_3$H$_7$—C(CH$_3$)$_2$— | H | H | C$_2$H$_5$ | C$_2$H$_5$ | O | O |
| (CH$_3$)$_2$CH—C(CH$_3$)$_2$— | H | H | C$_2$H$_5$ | C$_2$H$_5$ | O | O |
| HC≡C—C(CH$_3$)$_2$— | H | H | C$_2$H$_5$ | C$_2$H$_5$ | O | O |
| 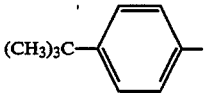 | H | H | C$_2$H$_5$ | C$_2$H$_5$ | O | O |
| C(CH$_3$)$_3$— | H | H | C$_2$H$_5$ | C$_2$H$_5$ | O | S |
| C(CH$_3$)$_3$— | H | H | C$_2$H$_5$ | C$_2$H$_5$ | S | O |
| C(CH$_3$)$_3$— | H | H | C$_2$H$_5$ | C$_2$H$_5$ | S | S |
| ClCH$_2$CH$_2$—C(CH$_3$)$_2$— | H | H | C$_2$H$_5$ | C$_2$H$_5$ | S | O |
| (CH$_3$)$_3$C— | H | H | C$_2$H$_5$ | C$_3$H$_7$ | O | O |
| ClCH$_2$—C(CH$_3$)$_2$— | H | H | C$_2$H$_5$ | C$_3$H$_7$ | O | O |
| FCH$_2$—C(CH$_3$)$_2$— | H | H | C$_2$H$_5$ | C$_3$H$_7$ | O | O |
| (CH$_3$)$_2$CH— | H | H | C$_2$H$_5$ | C$_3$H$_7$ | O | O |
| Cl—CH$_2$—CH(CH$_3$)— | H | H | C$_2$H$_5$ | C$_3$H$_7$ | O | O |
| C$_2$H$_5$CH(CH$_3$)— | H | H | C$_2$H$_5$ | C$_3$H$_7$ | O | O |
| 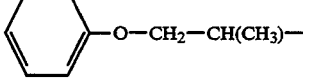 | H | H | C$_2$H$_5$ | C$_3$H$_7$ | O | O |
| 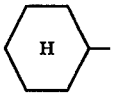 | H | H | C$_2$H$_5$ | C$_3$H$_7$ | O | O |

TABLE 1-continued

Examples of the compounds of the formula (I)

| R¹ | R² | R³ | R⁴ | R⁵ | X | Y |
|---|---|---|---|---|---|---|
|  | H | H | C₂H₅ | C₃H₇ | O | O |
|  | H | H | C₂H₅ | C₃H₇ | O | O |
| (CH₃)₂CH—CH(CH₃)— | H | H | C₂H₅ | C₃H₇ | O | O |
| (CH₃)₂CH—CH₂—CH(CH₃)— | H | H | C₂H₅ | C₃H₇ | O | O |
| 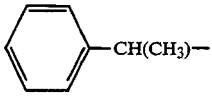 | H | H | C₂H₅ | C₃H₇ | O | O |
| 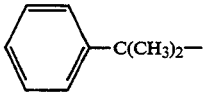 | H | H | C₂H₅ | C₃H₇ | O | O |
| C₄H₉ | H | H | C₂H₅ | C₃H₇ | O | O |
| C₂H₅—C(CH₃)₂— | H | H | C₂H₅ | C₃H₇ | O | O |
| C₃H₇—C(CH₃)₂— | H | H | C₂H₅ | C₃H₇ | O | O |
| (CH₃)₂CH—C(CH₃)₂— | H | H | C₂H₅ | C₃H₇ | O | O |
| HC≡C—C(CH₃)₂— | H | H | C₂H₅ | C₃H₇ | O | O |
| 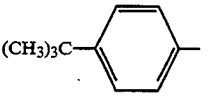 | H | H | C₂H₅ | C₃H₇ | O | O |
| C(CH₃)₃— | H | H | C₂H₅ | C₃H₇ | O | S |
| C(CH₃)₃— | H | H | C₂H₅ | C₃H₇ | S | O |
| C(CH₃)₃— | H | H | C₂H₅ | C₃H₇ | S | S |
| ClCH₂—C(CH₃2— | H | H | C₂H₅ | C₃H₇ | S | O |
| (CH₃)₃C— | H | CH₃ | H | CH₃ | O | O |
| ClCH₂—C(CH₃)₂— | H | CH₃ | H | CH₃ | O | O |
| FCH₂—C(CH₃)₂— | H | CH₃ | H | CH₃ | O | O |
| (CH₃)₂CH— | H | CH₃ | H | CH₃ | O | O |
| Cl—CH₂—CH(CH₃)— | H | CH₃ | H | CH₃ | O | O |
| C₂H₅CH(CH₃)— | H | CH₃ | H | CH₃ | O | O |
| 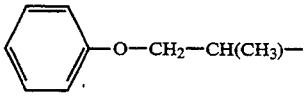 | H | CH₃ | H | CH₃ | O | O |
| 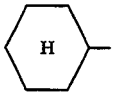 | H | CH₃ | H | CH₃ | O | O |
| 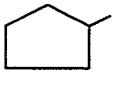 | H | CH₃ | H | CH₃ | O | O |
| 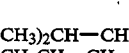 | H | CH₃ | H | CH₃ | O | O |
| (CH₃)₂CH—CH(CH₃)— | H | CH₃ | H | CH₃ | O | O |
| (CH₃CH—CH₂—CH(CH₃)— | H | CH₃ | H | CH₃ | O | O |
| 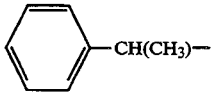 | H | CH₃ | H | CH₃ | O | O |
| 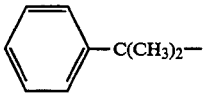 | H | CH₃ | H | CH₃ | O | O |

TABLE 1-continued

Examples of the compounds of the formula (I)

| R¹ | R² | R³ | R⁴ | R⁵ | X | Y |
|---|---|---|---|---|---|---|
| $C_4H_9$ | H | $CH_3$ | H | $CH_3$ | O | O |
| $C_2H_5-C(CH_3)_2-$ | H | $CH_3$ | H | $CH_3$ | O | O |
| $C_3H_7-C(CH_3)_2-$ | H | $CH_3$ | H | $CH_3$ | O | O |
| $(CH_3)_2CH-C(CH_3)_2-$ | H | $CH_3$ | H | $CH_3$ | O | O |
| $HC\equiv C-C(CH_3)_2-$ | H | $CH_3$ | H | $CH_3$ | O | O |
| $(CH_3)_3C$-C₆H₄- | H | $CH_3$ | H | $CH_3$ | O | O |
| $C(CH_3)_3-$ | H | $CH_3$ | H | $CH_3$ | O | S |
| $C(CH_3)_3-$ | H | $CH_3$ | H | $CH_3$ | S | O |
| $C(CH_3)_3-$ | H | $CH_3$ | H | $CH_3$ | S | S |
| $ClCH_2-C(CH_3)_2-$ | H | $CH_3$ | H | $CH_3$ | S | O |
| $(CH_3)_3C-$ | H | $CH_3$ | H | $C_2H_5$ | O | O |
| $ClCH_2-C(CH_3)_2-$ | H | $CH_3$ | H | $C_2H_5$ | O | O |
| $FCH_2-C(CH_3)_2-$ | H | $CH_3$ | H | $C_2H_5$ | O | O |
| $(CH_3)_2CH-$ | H | $CH_3$ | H | $C_2H_5$ | O | O |
| $Cl-CH_2-CH(CH_3)-$ | H | $CH_3$ | H | $C_2H_5$ | O | O |
| $C_2H_5CH(CH_3)-$ | H | $CH_3$ | H | $C_2H_5$ | O | O |
| C₆H₅-O-CH₂-CH(CH₃)- | H | $CH_3$ | H | $C_2H_5$ | O | O |
| cyclohexyl- | H | $CH_3$ | H | $C_2H_5$ | O | O |
| cyclopentyl- | H | $CH_3$ | H | $C_2H_5$ | O | O |
| cyclopropyl- | H | $CH_3$ | H | $C_2H_5$ | O | O |
| $(CH_3)_2CH-CH(CH_3)-$ | H | $CH_3$ | H | $C_2H_5$ | O | O |
| $(CH_3)_2CH-CH_2-CH(CH_3)-$ | H | $CH_3$ | H | $C_2H_5$ | O | O |
| C₆H₅-CH(CH₃)- | H | $CH_3$ | H | $C_2H_5$ | O | O |
| C₆H₅-C(CH₃)₂- | H | $CH_3$ | H | $C_2H_5$ | O | O |
| $C_4H_9$ | H | $CH_3$ | H | $C_2H_5$ | O | O |
| $C_2H_5-C(CH_3)_2-$ | H | $CH_3$ | H | $C_2H_5$ | O | O |
| $C_3H_7-C(CH_3)_2-$ | H | $CH_3$ | H | $C_2H_5$ | O | O |
| $(CH_3)_2CH-C(CH_3)_2-$ | H | $CH_3$ | H | $C_2H_5$ | O | O |
| $HC\equiv C-C(CH_3)_2-$ | H | $CH_3$ | H | $C_2H_5$ | O | O |
| $(CH_3)_3C$-C₆H₄- | H | $CH_3$ | H | $C_2H_5$ | O | O |
| $C(CH_3)_3-$ | H | $CH_3$ | H | $C_2H_5$ | O | S |
| $C(CH_3)_3-$ | H | $CH_3$ | H | $C_2H_5$ | S | O |
| $C(CH_3)_3-$ | H | $CH_3$ | H | $C_2H_5$ | S | S |
| $ClCH_2-C(CH_3)_2-$ | H | $CH_3$ | H | $C_2H_5$ | S | O |
| $(CH_3)_3C-$ | H | $CH_3$ | H | $C_3H_7$ | O | O |
| $ClCH_2-C(CH_3)_2-$ | H | $CH_3$ | H | $C_3H_7$ | O | O |
| $FCH_2-C(CH_3)_2-$ | H | $CH_3$ | H | $C_3H_7$ | O | O |
| $(CH_3)_2CH-$ | H | $CH_3$ | H | $C_3H_7$ | O | O |
| $Cl-CH_2-CH(CH_3)-$ | H | $CH_3$ | H | $C_3H_7$ | O | O |

TABLE 1-continued

Examples of the compounds of the formula (I)

| R¹ | R² | R³ | R⁴ | R⁵ | X | Y |
|---|---|---|---|---|---|---|
| $C_2H_5CH(CH_3)-$ | H | $CH_3$ | H | $C_3H_7$ | O | O |
| 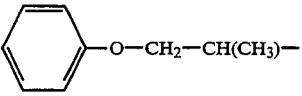 —O—CH₂—CH(CH₃)— | H | $CH_3$ | H | $C_3H_7$ | O | O |
| 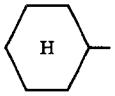 | H | $CH_3$ | H | $C_3H_7$ | O | O |
| 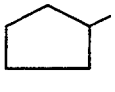 | H | $CH_3$ | H | $C_3H_7$ | O | O |
| 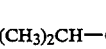 | H | $CH_3$ | H | $C_3H_7$ | O | O |
| $(CH_3)_2CH-CH(CH_3)-$ | H | $CH_3$ | H | $C_3H_7$ | O | O |
| $(CH_3)_2CH-CH_2-CH(CH_3)-$ | H | $CH_3$ | H | $C_3H_7$ | O | O |
| 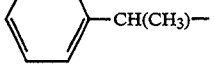—CH(CH₃)— | H | $CH_3$ | H | $C_3H_7$ | O | O |
| 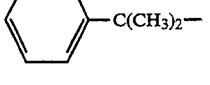—C(CH₃)₂— | H | $CH_3$ | H | $C_3H_7$ | O | O |
| $C_4H_9$ | H | $CH_3$ | H | $C_3H_7$ | O | O |
| $C_2H_5-C(CH_3)_2-$ | H | $CH_3$ | H | $C_3H_7$ | O | O |
| $C_3H_7-C(CH_3)_2-$ | H | $CH_3$ | H | $C_3H_7$ | O | O |
| $(CH_3)_2CH-C(CH_3)_2-$ | H | $CH_3$ | H | $C_3H_7$ | O | O |
| $HC\equiv C-C(CH_3)_2-$ | H | $CH_3$ | H | $C_3H_7$ | O | O |
| $(CH_3)_3C-$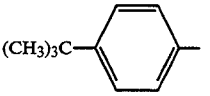— | H | $CH_3$ | H | $C_3H_7$ | O | O |
| $C(CH_3)_3-$ | H | $CH_3$ | H | $C_3H_7$ | O | S |
| $C(CH_3)_3-$ | H | $CH_3$ | H | $C_3H_7$ | S | O |
| $C(CH_3)_3-$ | H | $CH_3$ | H | $C_3H_7$ | S | S |
| $ClCH_2-C(CH_3)_2-$ | H | $CH_3$ | H | $C_3H_7$ | S | O |
| $(CH_3)_3C$ | H | $CH_3$ | $CH_3$ | $CH_3$ | O | O |
| $ClCH_2-C(CH_3)_2-$ | H | $CH_3$ | $CH_3$ | $CH_3$ | O | O |
| $FCH_2-C(CH_3)_2-$ | H | $CH_3$ | $CH_3$ | $CH_3$ | O | O |
| $(CH_3)_2CH-$ | H | $CH_3$ | $CH_3$ | $CH_3$ | O | O |
| $Cl-CH_2-CH(CH_3)-$ | H | $CH_3$ | $CH_3$ | $CH_3$ | O | O |
| $C_2H_5CH(CH_3)-$ | H | $CH_3$ | $CH_3$ | $CH_3$ | O | O |
| 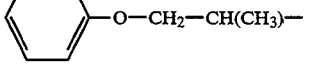—O—CH₂—CH(CH₃)— | H | $CH_3$ | $CH_3$ | $CH_3$ | O | O |
| 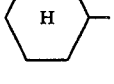 | H | $CH_3$ | $CH_3$ | $CH_3$ | O | O |
|  | H | $CH_3$ | $CH_3$ | $CH_3$ | O | O |
|  | H | $CH_3$ | $CH_3$ | $CH_3$ | O | O |

TABLE 1-continued

Examples of the compounds of the formula (I)

| R¹ | R² | R³ | R⁴ | R⁵ | X | Y |
|---|---|---|---|---|---|---|
| (CH₃)₂CH—CH(CH₃)— | H | CH₃ | CH₃ | CH₃ | O | O |
| (CH₃)₂CH—CH₂—CH(CH₃)— | H | CH₃ | CH₃ | CH₃ | O | O |
| 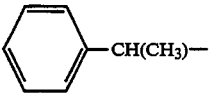—CH(CH₃)— | H | CH₃ | CH₃ | CH₃ | O | O |
| 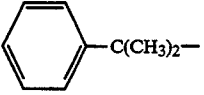—C(CH₃)₂— | H | CH₃ | CH₃ | CH₃ | O | O |
| C₄H₉ | H | CH₃ | CH₃ | CH₃ | O | O |
| C₂H₅—C(CH₃)₂— | H | CH₃ | CH₃ | CH₃ | O | O |
| C₃H₇—C(CH₃)₂— | H | CH₃ | CH₃ | CH₃ | O | O |
| (CH₃)₂CH—C(CH₃)₂— | H | CH₃ | CH₃ | CH₃ | O | O |
| HC≡C—C(CH₃)₂— | H | CH₃ | CH₃ | CH₃ | O | O |
| (CH₃)₃C—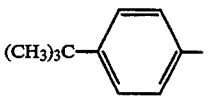— | H | CH₃ | CH₃ | CH₃ | O | O |
| C(CH₃)₃— | H | CH₃ | CH₃ | CH₃ | O | S |
| C(CH₃)₃— | H | CH₃ | CH₃ | CH₃ | S | O |
| C(CH₃)₃— | H | CH₃ | CH₃ | CH₃ | S | S |
| ClCH₂—C(CH₃)₂— | H | CH₃ | CH₃ | CH₃ | S | O |
| (CH₃)₃C— | H | CH₃ | CH₃ | C₂H₅ | O | O |
| ClCH₂—C(CH₃)₂— | H | CH₃ | CH₃ | C₂H₅ | O | O |
| FCH₂—C(CH₃)₂— | H | CH₃ | CH₃ | C₂H₅ | O | O |
| (CH₃)₂CH— | H | CH₃ | CH₃ | C₂H₅ | O | O |
| Cl—CH₂—CH(CH₃)— | H | CH₃ | CH₃ | C₂H₅ | O | O |
| C₂H₅CH(CH₃)— | H | CH₃ | CH₃ | C₂H₅ | O | O |
| 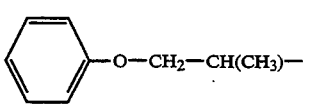—O—CH₂—CH(CH₃)— | H | CH₃ | CH₃ | C₂H₅ | O | O |
| 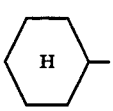— | H | CH₃ | CH₃ | C₂H₅ | O | O |
| 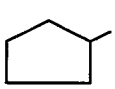— | H | CH₃ | CH₃ | C₂H₅ | O | O |
| — | H | CH₃ | CH₃ | C₂H₅ | O | O |
| (CH₃)₂CH—CH(CH₃)— | H | CH₃ | CH₃ | C₂H₅ | O | O |
| (CH₃)₂CH—CH₂—CH(CH₃)— | H | CH₃ | CH₃ | C₂H₅ | O | O |
| 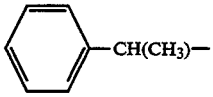—CH(CH₃)— | H | CH₃ | CH₃ | C₂H₅ | O | O |
| 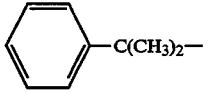—C(CH₃)₂— | H | CH₃ | CH₃ | C₂H₅ | O | O |
| C₄H₉ | H | CH₃ | CH₃ | C₂H₅ | O | O |
| C₂H₅—C(CH₃)₂— | H | CH₃ | CH₃ | C₂H₅ | O | O |
| C₃H₇—C(CH₃)₂— | H | CH₃ | CH₃ | C₂H₅ | O | O |
| (CH₃)₂CH—C(CH₃)₂— | H | CH₃ | CH₃ | C₂H₅ | O | O |
| HC≡C—C(CH₃)₂— | H | CH₃ | CH₃ | C₂H₅ | O | O |

TABLE 1-continued

Examples of the compounds of the formula (I)

| R¹ | R² | R³ | R⁴ | R⁵ | X | Y |
|---|---|---|---|---|---|---|
| (CH₃)₃C—⟨C₆H₄⟩— | H | CH₃ | CH₃ | C₂H₅ | O | O |
| C(CH₃)₃— | H | CH₃ | CH₃ | C₂H₅ | O | S |
| C(CH₃)₃— | H | CH₃ | CH₃ | C₂H₅ | S | O |
| C(CH₃)₃— | H | CH₃ | CH₃ | C₂H₅ | S | S |
| ClCH₂—C(CH₃)₂— | H | CH₃ | CH₃ | C₂H₅ | S | O |
| (CH₃)₃C— | H | CH₃ | CH₃ | C₃H₇ | O | O |
| ClCH₂—C(CH₃)₂— | H | CH₃ | CH₃ | C₃H₇ | O | O |
| FCH₂—C(CH₃)₂— | H | CH₃ | CH₃ | C₃H₇ | O | O |
| (CH₃)₂CH— | H | CH₃ | CH₃ | C₃H₇ | O | O |
| Cl—CH₂—CH(CH₃)— | H | CH₃ | CH₃ | C₃H₇ | O | O |
| C₂H₅CH(CH₃)— | H | CH₃ | CH₃ | C₃H₇ | O | O |
| ⟨C₆H₅⟩—O—CH₂—CH(CH₃)— | H | CH₃ | CH₃ | C₃H₇ | O | O |
| ⟨cyclohexyl-H⟩— | H | CH₃ | CH₃ | C₃H₇ | O | O |
| ⟨cyclopentyl⟩— | H | CH₃ | CH₃ | C₃H₇ | O | O |
| ⟨cyclopropyl⟩— | H | CH₃ | CH₃ | C₃H₇ | O | O |
| (CH₃)₂CH—CH(CH₃)— | H | CH₃ | CH₃ | C₃H₇ | O | O |
| (CH₃)₂CH—CH₂—CH(CH₃)— | H | CH₃ | CH₃ | C₃H₇ | O | O |
| ⟨C₆H₅⟩—CH(CH₃)— | H | CH₃ | CH₃ | C₃H₇ | O | O |
| ⟨C₆H₅⟩—C(CH₃)₂— | H | CH₃ | CH₃ | C₃H₇ | O | O |
| C₄H₉ | H | CH₃ | CH₃ | C₃H₇ | O | O |
| C₂H₅—C(CH₃)₂— | H | CH₃ | CH₃ | C₃H₇ | O | O |
| C₃H₇—C(CH₃)₂— | H | CH₃ | CH₃ | C₃H₇ | O | O |
| (CH₃)₂CH—C(CH₃)₂— | H | CH₃ | CH₃ | C₃H₇ | O | O |
| HC≡C—C(CH₃)₂— | H | CH₃ | CH₃ | C₃H₇ | O | O |
| (CH₃)₃C—⟨C₆H₄⟩— | H | CH₃ | CH₃ | C₃H₇ | O | O |
| C(CH₃)₃— | H | CH₃ | CH₃ | C₃H₇ | O | S |
| C(CH₃)₃— | H | CH₃ | CH₃ | C₃H₇ | S | O |
| C(CH₃)₃— | H | CH₃ | CH₃ | C₃H₇ | S | S |
| ClCH₂—C(CH₃)₂— | H | CH₃ | CH₃ | C₃H₇ | S | O |
| (CH₃)₃C— | H | CH₃ | C₂H₅ | C₂H₅ | O | O |
| ClCH₂—C(CH₃)₂— | H | CH | C₂H₅ | C₂H₅ | O | O |
| FCH₂—C(CH₃)₂— | H | CH₃ | C₂H₅ | C₂H₅ | O | O |
| (CH₃)₂CH— | H | CH₃ | C₂H₅ | C₂H₅ | O | O |
| Cl—CH₂—CH(CH₃)— | H | CH₃ | C₂H₅ | C₂H₅ | O | O |
| C₂H₅CH(CH₃)— | H | CH₃ | C₂H₅ | C₂H₅ | O | O |
| ⟨C₆H₅⟩—O—CH₂—CH(CH₃)— | H | CH₃ | C₂H₅ | C₂H₅ | O | O |

TABLE 1-continued

Examples of the compounds of the formula (I)

| R¹ | R² | R³ | R⁴ | R⁵ | X | Y |
|---|---|---|---|---|---|---|
| 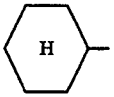 | H | CH₃ | C₂H₅ | C₂H₅ | O | O |
|  | H | CH₃ | C₂H₅ | C₂H₅ | O | O |
|  | H | CH₃ | C₂H₅ | C₂H₅ | O | O |
| (CH₃)₂CH—CH(CH₃)— | H | CH₃ | C₂H₅ | C₂H₅ | O | O |
| (CH₃)₂CH—CH₂—CH(CH₃)— | H | CH₃ | C₂H₅ | C₂H₅ | O | O |
| 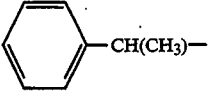 | H | CH₃ | C₂H₅ | C₂H₅ | O | O |
| 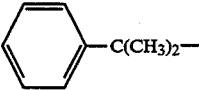 | H | CH₃ | C₂H₅ | C₂H₅ | O | O |
| C₄H₉ | H | CH₃ | C₂H₅ | C₂H₅ | O | O |
| C₂H₅—C(CH₃)₂— | H | CH₃ | C₂H₅ | C₂H₅ | O | O |
| C₃H₇—C(CH₃)₂— | H | CH₃ | C₂H₅ | C₂H₅ | O | O |
| (CH₃)₂CH—C(CH₃)₂— | H | CH₃ | C₂H₅ | C₂H₅ | O | O |
| HC≡C—C(CH₃)₂— | H | CH₃ | C₂H₅ | C₂H₅ | O | O |
| 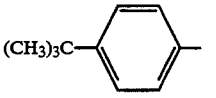 | H | CH₃ | C₂H₅ | C₂H₅ | O | O |
| C(CH₃)₃— | H | CH₃ | C₂H₅ | C₂H₅ | O | S |
| C(CH₃)₃— | H | CH₃ | C₂H₅ | C₂H₅ | S | O |
| C(CH₃)₃— | H | CH₃ | C₂H₅ | C₂H₅ | S | S |
| ClCH₂—C(CH₃)₂— | H | CH₃ | C₂H₅ | C₂H₅ | S | O |
| (CH₃)₃C— | H | CH₃ | C₃H₇ | C₃H₇ | O | O |
| ClCH₂—C(CH₃)₂— | H | CH₃ | C₃H₇ | C₃H₇ | O | O |
| FCH₂—C(CH₃)₂— | H | CH₃ | C₃H₇ | C₃H₇ | O | O |
| (CH₃)₂CH— | H | CH | C₃H₇ | C₃H₇ | O | O |
| Cl—CH₂—CH(CH₃)— | H | CH₃ | C₃H₇ | C₃H₇ | O | O |
| C₂H₅CH(CH₃)— | H | CH₃ | C₃H₇ | C₃H₇ | O | O |
| 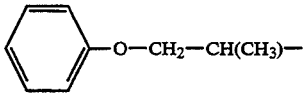 | H | CH₃ | C₃H₇ | C₃H₇ | O | O |
| 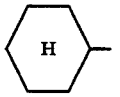 | H | CH₃ | C₃H₇ | C₃H₇ | O | O |
| 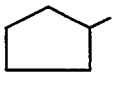 | H | CH₃ | C₃H₇ | C₃H₇ | O | O |
|  | H | CH₃ | C₃H₇ | C₃H₇ | O | O |
| (CH₃)₂CH—CH(CH₃)— | H | CH₃ | C₃H₇ | C₃H₇ | O | O |
| (CH₃)₂CH—CH₂—CH(CH₃)— | H | CH₃ | C₃H₇ | C₃H₇ | O | O |
| 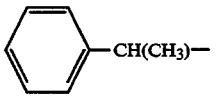 | H | CH₃ | C₃H₇ | C₃H₇ | O | O |

TABLE 1-continued

Examples of the compounds of the formula (I)

| R¹ | R² | R³ | R⁴ | R⁵ | X | Y |
|---|---|---|---|---|---|---|
| 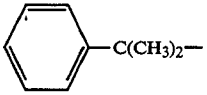—C(CH$_3$)$_2$— | H | CH$_3$ | C$_3$H$_7$ | C$_3$H$_7$ | O | O |
| C$_4$H$_9$ | H | CH$_3$ | C$_3$H$_7$ | C$_3$H$_7$ | O | O |
| C$_2$H$_5$—C(CH$_3$)$_2$— | H | CH$_3$ | C$_3$H$_7$ | C$_3$H$_7$ | O | O |
| C$_3$H$_7$—C(CH$_3$)$_2$— | H | CH$_3$ | C$_3$H$_7$ | C$_3$H$_7$ | O | O |
| (CH$_3$)$_2$CH—C(CH$_3$)$_2$— | H | CH$_3$ | C$_3$H$_7$ | C$_3$H$_7$ | O | O |
| HC≡C—C(CH$_3$)$_2$— | H | CH$_3$ | C$_3$H$_7$ | C$_3$H$_7$ | O | O |
| (CH$_3$)$_3$C—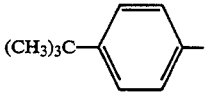— | H | CH$_3$ | C$_3$H$_7$ | C$_3$H$_7$ | O | O |
| C(CH$_3$)$_3$— | H | CH$_3$ | C$_3$H$_7$ | C$_3$H$_7$ | O | S |
| C(CH$_3$)$_3$— | H | CH$_3$ | C$_3$H$_7$ | C$_3$H$_7$ | S | O |
| C(CH$_3$)$_3$— | H | CH$_3$ | C$_3$H$_7$ | C$_3$H$_7$ | S | S |
| ClCH$_2$—C(CH$_3$)$_2$— | H | CH$_3$ | C$_3$H$_7$ | C$_3$H$_7$ | S | O |
| (CH$_3$)$_3$C— | H | C$_2$H$_5$ | H | CH$_3$ | O | O |
| ClCH$_2$—C(CH$_3$)$_2$— | H | C$_2$H$_5$ | H | CH$_3$ | O | O |
| FCH$_2$—C(CH$_3$)$_2$— | H | C$_2$H$_5$ | H | CH$_3$ | O | O |
| (CH$_3$)$_2$CH— | H | C$_2$H$_5$ | H | CH$_3$ | O | O |
| Cl—CH$_2$—CH(CH$_3$)— | H | C$_2$H$_5$ | H | CH$_3$ | O | O |
| C$_2$H$_5$CH(CH$_3$)— | H | C$_2$H$_5$ | H | CH$_3$ | O | O |
| 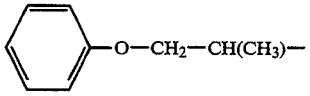—O—CH$_2$—CH(CH$_3$)— | H | C$_2$H$_5$ | H | CH$_3$ | O | O |
| 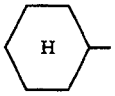— | H | C$_2$H$_5$ | H | CH$_3$ | O | O |
| 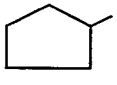— | H | C$_2$H$_5$ | H | CH$_3$ | O | O |
| — | H | C$_2$H$_5$ | H | CH$_3$ | O | O |
| (CH$_3$)$_2$CH—CH(CH$_3$)— | H | C$_2$H$_5$ | H | CH$_3$ | O | O |
| (CH$_3$)$_2$CH—CH$_2$—CH(CH$_3$)— | H | C$_2$H$_5$ | H | CH$_3$ | O | O |
| 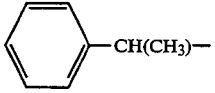—CH(CH$_3$)— | H | C$_2$H$_5$ | H | CH$_3$ | O | O |
| 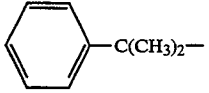—C(CH$_3$)$_2$— | H | C$_2$H$_5$ | H | CH$_3$ | O | O |
| C$_4$H$_9$ | H | C$_2$H$_5$ | H | CH$_3$ | O | O |
| C$_2$H$_5$—C(CH$_3$)$_2$— | H | C$_2$H$_5$ | H | CH$_3$ | O | O |
| C$_3$H$_7$—C(CH$_3$)$_2$— | H | C$_2$H$_5$ | H | CH$_3$ | O | O |
| (CH$_3$)$_2$CH—C(CH$_3$)$_2$— | H | C$_2$H$_5$ | H | CH$_3$ | O | O |
| HC≡C—C(CH$_3$)$_2$— | H | C$_2$H$_5$ | H | CH$_3$ | O | O |
| (CH$_3$)$_3$C—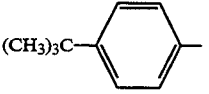— | H | C$_2$H$_5$ | H | CH$_3$ | O | O |
| C(CH$_3$)$_3$— | H | C$_2$H$_5$ | H | CH$_3$ | O | S |
| C(CH$_3$)$_3$— | H | C$_2$H$_5$ | H | CH$_3$ | S | O |
| C(CH$_3$)$_3$— | H | C$_2$H$_5$ | H | CH$_3$ | S | S |

TABLE 1-continued

Examples of the compounds of the formula (I)

| R¹ | R² | R³ | R⁴ | R⁵ | X | Y |
|---|---|---|---|---|---|---|
| ClCH$_2$—C(CH$_3$)$_2$— | H | C$_2$H$_5$ | H | CH$_3$ | S | O |
| (CH$_3$)$_3$C— | H | C$_2$H$_5$ | H | C$_2$H$_5$ | O | O |
| ClCH$_2$—C(CH$_3$)$_2$— | H | C$_2$H$_5$ | H | C$_2$H$_5$ | O | O |
| FCH$_2$—C(CH$_3$)$_2$— | H | C$_2$H$_5$ | H | C$_2$H$_5$ | O | O |
| (CH$_3$)$_2$CH— | H | C$_2$H$_5$ | H | C$_2$H$_5$ | O | O |
| ClCH$_2$—CH(CH$_3$)— | H | C$_2$H$_5$ | H | C$_2$H$_5$ | O | O |
| C$_2$H$_5$CH(CH$_3$)— | H | C$_2$H$_5$ | H | C$_2$H$_5$ | O | O |
| 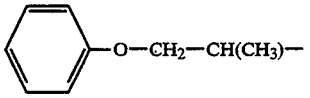 | H | C$_2$H$_5$ | H | C$_2$H$_5$ | O | O |
| 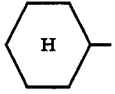 | H | C$_2$H$_5$ | H | C$_2$H$_5$ | O | O |
| 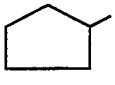 | H | C$_2$H$_5$ | H | C$_2$H$_5$ | O | O |
| 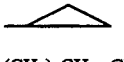 | H | C$_2$H$_5$ | H | C$_2$H$_5$ | O | O |
| (CH$_3$)$_2$CH—CH(CH$_3$)— | H | C$_2$H$_5$ | H | C$_2$H$_5$ | O | O |
| (CH$_3$)$_2$CH—CH$_2$—CH(CH$_3$)— | H | C$_2$H$_5$ | H | C$_2$H$_5$ | O | O |
| 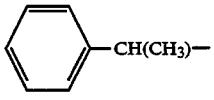 | H | C$_2$H$_5$ | H | C$_2$H$_5$ | O | O |
| 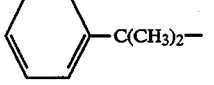 | H | C$_2$H$_5$ | H | C$_2$H$_5$ | O | O |
| C$_4$H$_9$ | H | C$_2$H$_5$ | H | C$_2$H$_5$ | O | O |
| C$_2$H$_5$—C(CH$_3$)$_2$— | H | C$_2$H$_5$ | H | C$_2$H$_5$ | O | O |
| C$_3$H$_7$—C(CH$_3$)$_2$— | H | C$_2$H$_5$ | H | C$_2$H$_5$ | O | O |
| (CH$_3$)$_2$CH—C(CH$_3$)$_2$— | H | C$_2$H$_5$ | H | C$_2$H$_5$ | O | O |
| HC≡C—C(CH$_3$)$_2$— | H | C$_2$H$_5$ | H | C$_2$H$_5$ | O | O |
| 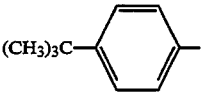 | H | C$_2$H$_5$ | H | C$_2$H$_5$ | O | O |
| C(CH$_3$)$_3$— | H | C$_2$H$_5$ | H | C$_2$H$_5$ | O | S |
| C(CH$_3$)$_3$— | H | C$_2$H$_5$ | H | C$_2$H$_5$ | S | O |
| C(CH$_3$)$_3$— | H | C$_2$H$_5$ | H | C$_2$H$_5$ | S | S |
| ClCH$_2$—C(CH$_3$)$_2$— | H | C$_2$H$_5$ | H | C$_2$H$_5$ | S | O |
| (CH$_3$)$_3$C— | H | C$_2$H$_5$ | CH$_3$ | CH$_3$ | O | O |
| ClCH$_2$—C(CH$_3$)$_2$— | H | C$_2$H$_5$ | CH$_3$ | CH$_3$ | O | O |
| FCH$_2$—C(CH$_3$)$_2$— | H | C$_2$H$_5$ | CH$_3$ | CH$_3$ | O | O |
| (CH$_3$)$_2$CH— | H | C$_2$H$_5$ | CH$_3$ | CH$_3$ | O | O |
| ClCH$_2$—CH(CH$_3$)— | H | C$_2$H$_5$ | CH$_3$ | CH$_3$ | O | O |
| C$_2$H$_5$CH(CH$_3$)— | H | C$_2$H$_5$ | CH$_3$ | CH$_3$ | O | O |
| 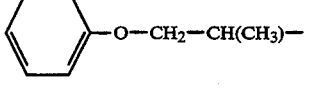 | H | C$_2$H$_5$ | CH$_3$ | CH$_3$ | O | O |
| 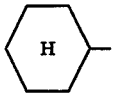 | H | C$_2$H$_5$ | CH$_3$ | CH$_3$ | O | O |

TABLE 1-continued

Examples of the compounds of the formula (I)

| R¹ | R² | R³ | R⁴ | R⁵ | X | Y |
|---|---|---|---|---|---|---|
|  | H | C₂H₅ | CH₃ | CH₃ | O | O |
| 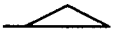 | H | C₂H₅ | CH₃ | CH₃ | O | O |
| (CH₃)₂CH—CH(CH₃)— | H | C₂H₅ | CH₃ | CH₃ | O | O |
| (CH₃)₂CH—CH₂—CH(CH₃)— | H | C₂H₅ | CH₃ | CH₃ | O | O |
| 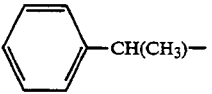 | H | C₂H₅ | CH₃ | CH₃ | O | O |
| 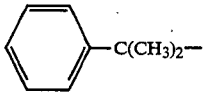 | H | C₂H₅ | CH₃ | CH₃ | O | O |
| C₄H₉ | H | C₂H₅ | CH₃ | CH₃ | O | O |
| C₂H₅—C(CH₃)₂— | H | C₂H₅ | CH₃ | CH₃ | O | O |
| C₃H₇—C(C(CH₃)₂— | H | C₂H₅ | CH₃ | CH₃ | O | O |
| (CH₃)₂CH—C(CH₃)₂— | H | C₂H₅ | CH₃ | CH₃ | O | O |
| HC≡C—C(CH₃)₂— | H | C₂H₅ | CH₃ | CH₃ | O | O |
| 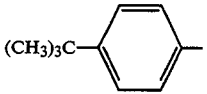 | H | C₂H₅ | CH₃ | CH₃ | O | O |
| C(CH₃)₃— | H | C₂H₅ | CH₃ | CH₃ | O | S |
| C(CH₃)₃— | H | C₂H₅ | CH₃ | CH₃ | S | O |
| C(CH₃)₃ | H | C₂H₅ | CH₃ | CH₃ | S | S |
| ClCH₂—C(CH₃)₂— | H | C₂H₅ | CH₃ | CH₃ | S | O |
| (CH₃)₃C— | CH₃ | CH₃ | CH₃ | CH₃ | O | O |
| ClCH₂—C(CH₃)₂— | CH₃ | CH₃ | CH₃ | CH₃ | O | O |
| FCH₂—C(CH₃)₂— | CH₃ | CH₃ | CH₃ | CH₃ | O | O |
| (CH₃)₂CH— | CH₃ | CH₃ | CH₃ | CH₃ | O | O |
| ClCH₂—CH(CH₃)— | CH₃ | CH₃ | CH₃ | CH₃ | O | O |
| C₂H₅CH(CH₃)— | CH₃ | CH₃ | CH₃ | CH₃ | O | O |
| 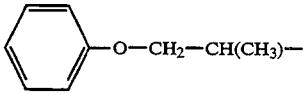 | CH₃ | CH₃ | CH₃ | CH₃ | O | O |
| 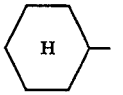 | CH₃ | CH₃ | CH₃ | CH₃ | O | O |
| 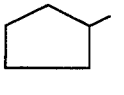 | CH₃ | CH₃ | CH₃ | CH₃ | O | O |
|  | CH₃ | CH₃ | CH₃ | CH₃ | O | O |
| (CH₃)₂CH—CH(CH₃)— | CH₃ | CH₃ | CH₃ | CH₃ | O | O |
| (CH₃)₂CH—CH₂—CH(CH₃)— | CH₃ | CH₃ | CH₃ | CH₃ | O | O |
| 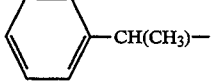 | CH₃ | CH₃ | CH₃ | CH₃ | O | O |
| 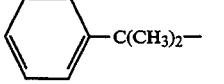 | CH₃ | CH₃ | CH₃ | CH₃ | O | O |

TABLE 1-continued

Examples of the compounds of the formula (I)

| R¹ | R² | R³ | R⁴ | R⁵ | X | Y |
|---|---|---|---|---|---|---|
| C₄H₉ | CH₃ | CH₃ | CH₃ | CH₃ | O | O |
| C₂H₅—C(CH₃)₂— | CH₃ | CH₃ | CH₃ | CH₃ | O | O |
| C₃H₇—C(CH₃)₂— | CH₃ | CH₃ | CH₃ | CH₃ | O | O |
| (CH₃)₂CH—C(CH₃)₂— | CH₃ | CH₃ | CH₃ | CH₃ | O | O |
| HC≡C—C(CH₃)₂— | CH₃ | CH₃ | CH₃ | CH₃ | O | O |
| (CH₃)₃C—⟨C₆H₄⟩— | CH₃ | CH₃ | CH₃ | CH₃ | O | O |
| C(CH₃)₃— | CH₃ | CH₃ | CH₃ | CH₃ | O | S |
| C(CH₃)₃— | CH₃ | CH₃ | CH₃ | CH₃ | S | O |
| C(CH₃)₃— | CH₃ | CH₃ | CH₃ | CH₃ | S | S |
| ClCH₂—C(CH₃)₂— | CH₃ | CH₃ | CH₃ | CH₃ | S | O |
| (CH₃)₃C— | CH₃ | CH₃ | C₂H₅ | CH₃ | O | O |
| ClCH₂—C(CH₃)₂— | CH₃ | CH₃ | C₂H₅ | CH₃ | O | O |
| FCH₂—C(CH₃)₂— | CH₃ | CH₃ | C₂H₅ | CH₃ | O | O |
| (CH₃)₂CH— | CH₃ | CH₃ | C₂H₅ | CH₃ | O | O |
| ClCH₂—CH(CH₃)— | CH₃ | CH₃ | C₂H₅ | CH₃ | O | O |
| C₂H₅CH(CH₃)— | CH₃ | CH₃ | C₂H₅ | CH₃ | O | O |
| ⟨C₆H₅⟩—O—CH₂—CH(CH₃)— | CH₃ | CH₃ | C₂H₅ | CH₃ | O | O |
| ⟨cyclohexyl-H⟩— | CH₃ | CH₃ | C₂H₅ | CH₃ | O | O |
| ⟨cyclopentyl⟩— | CH₃ | CH₃ | C₂H₅ | CH₃ | O | O |
| ⟨cyclopropyl⟩— | CH₃ | CH₃ | C₂H₅ | CH₃ | O | O |
| (CH₃)₂CH—CH(CH₃)— | CH₃ | CH₃ | C₂H₅ | CH₃ | O | O |
| (CH₃)₂CH—CH₂—CH(CH₃)— | CH₃ | CH₃ | C₂H₅ | CH₃ | O | O |
| ⟨C₆H₅⟩—CH(CH₃)— | CH₃ | CH₃ | C₂H₅ | CH₃ | O | O |
| ⟨C₆H₅⟩—C(CH₃)₂— | CH₃ | CH₃ | C₂H₅ | CH₃ | O | O |
| C₄H₉ | CH₃ | CH₃ | C₂H₅ | CH₃ | O | O |
| C₂H₅—C(CH₃)₂— | CH₃ | CH₃ | C₂H₅ | CH₃ | O | O |
| C₃H₇—C(CH₃)₂— | CH₃ | CH₃ | C₂H₅ | CH₃ | O | O |
| (CH₃)₂CH—C(CH₃)₂— | CH₃ | CH₃ | C₂H₅ | CH₃ | O | O |
| HC≡C—C(CH₃)₂— | CH₃ | CH₃ | C₂H₅ | CH₃ | O | O |
| (CH₃)₃C—⟨C₆H₄⟩— | CH₃ | CH₃ | C₂H₅ | CH₃ | O | O |
| C(CH₃)₃— | CH₃ | CH₃ | C₂H₅ | CH₃ | O | S |
| C(CH₃)₃— | CH₃ | CH₃ | C₂H₅ | CH₃ | S | O |
| C(CH₃)₃— | CH₃ | CH₃ | C₂H₅ | CH₃ | S | S |
| ClCH₂—C(CH₃)₂— | CH₃ | CH₃ | C₂H₅ | CH₃ | S | O |
| (CH₃)₃C— | H | H | H | ⟨cyclopropyl⟩ | O | O |

TABLE 1-continued
| Examples of the compounds of the formula (I) | | | | | | |
|---|---|---|---|---|---|---|
| R¹ | R² | R³ | R⁴ | R⁵ | X | Y |
| ClCH₂—C(CH₃)₂— | H | H | H | 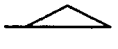 | O | O |
| FCH₂—C(CH₃)₂— | H | H | H |  | O | O |
| (CH₃)₂CH— | H | H | H |  | O | O |
| ClCH₂—CH(CH₃)— | H | H | H | 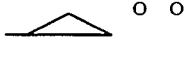 | O | O |
| C₂H₅CH(CH₃)— | H | H | H |  | O | O |
| 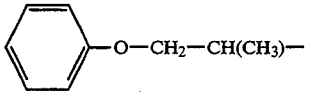 | H | H | H |  | O | O |
| 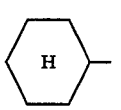 | H | H | H |  | O | O |
| 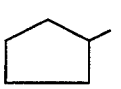 | H | H | H | 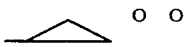 | O | O |
| 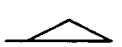 | H | H | H |  | O | O |
| (CH₃)₂CH—CH(CH₃)— | H | H | H |  | O | O |
| (CH₃)₂CH—CH₂—CH(CH₃)— | H | H | H |  | O | O |
| 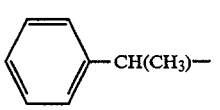 | H | H | H |  | O | O |
| 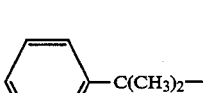 | H | H | H |  | O | O |
| C₄H₉ | H | H | H |  | O | O |
| C₂H₅—C(CH₃)₂— | H | H | H |  | O | O |
| C₃H₇—C(CH₃)₂— | H | H | H |  | O | O |
| (CH₃)₂CH—C(CH₃)₂— | H | H | H |  | O | O |
| HC≡C—C(CH₃)₂— | H | H | H |  | O | O |
| 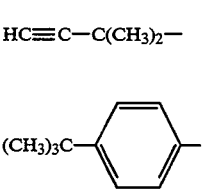 | H | H | H |  | O | O |
| C(CH₃)₃— | H | H | H |  | O | S |
| C(CH₃)₃— | H | H | H |  | S | O |

TABLE 1-continued

Examples of the compounds of the formula (I)

| R¹ | R² | R³ | R⁴ | R⁵ | X | Y |
|---|---|---|---|---|---|---|
| C(CH₃)₃— | H | H | H |  | S | S |
| ClCH₂—C(CH₃)₂— | H | H | H |  | S | O |
| (CH₃)₃C— | H | CH₃ | H |  | O | O |
| ClCH₂—C(CH₃)₂— | H | CH₃ | H |  | O | O |
| FCH₂—C(CH₃)₂— | H | CH₃ | H |  | O | O |
| (CH₃)₂CH— | H | CH₃ | H |  | O | O |
| Cl—CH₂—CH(CH₃)— | H | CH₃ | H |  | O | O |
| C₂H₅CH(CH₃)— | H | CH₃ | H |  | O | O |
|  | H | CH₃ | H |  | O | O |
| 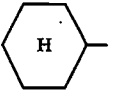 | H | CH₃ | H |  | O | O |
| 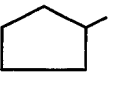 | H | CH₃ | H |  | O | O |
|  | H | CH₃ | H |  | O | O |
| (CH₃)₂CH—CH(CH₃)— | H | CH₃ | H |  | O | O |
| (CH₃)₂CH—CH₂—CH(CH₃)— | H | CH₃ | H |  | O | O |
|  | H | CH₃ | H |  | O | O |
|  | H | CH₃ | H |  | O | O |
| C₄H₉ | H | CH₃ | H |  | O | O |
| C₂H₅—C(CH₃)₂— | H | CH₃ | H |  | O | O |
| C₃H₇—C(CH₃)₂— | H | CH₃ | H |  | O | O |
| (CH₃)₂CH—C(CH₃)₂— | H | CH₃ | H |  | O | O |
| HC≡C—C(CH₃)₂— | H | CH₃ | H |  | O | O |

TABLE 1-continued

| | Examples of the compounds of the formula (I) | | | | | | |
|---|---|---|---|---|---|---|---|
| $R^1$ | $R^2$ | $R^3$ | $R^4$ | $R^5$ | | X | Y |
| (CH₃)₃C—⟨phenyl⟩— | H | CH₃ | H | △ | | O | O |
| C(CH₃)₃— | H | CH₃ | H | △ | | O | S |
| C(CH₃)₃— | H | CH₃ | H | △ | | S | O |
| C(CH₃)₃— | H | CH₃ | H | △ | | S | S |
| ClCH₂—C(CH₃)₂— | H | CH₃ | H | △ | | S | O |

If, for example, 4-methylamino-5-dimethylamino-2,4-dihydro-3H-1,2,4-triazol-3-one and sec-butyl isocyanate are used as the starting substances, the course of the reaction in process (a) according to the invention may be represented by the following equation:

If, for example, 2-cyclohexylaminocarbonyl-4-isopropylideneamino-5-dipropylamino-2,4-dihydro-3H-1,2,4-triazol-3-one is used as the starting substance, the course of the reaction in process (b) according to the invention may be represented by the following equation:

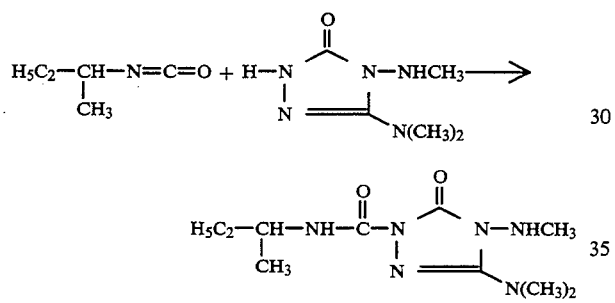

If, for example, 2-phenoxycarbonyl-4-methylamino-5-(N-methylpropylamino)-2,4-dihydro-3H-1,2,4-triazol-3-one and pentylamine are used as the starting substances, the course of the reaction in process (c) according to the invention may be represented by the following equation:

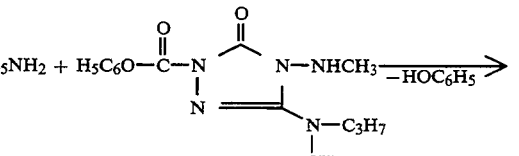

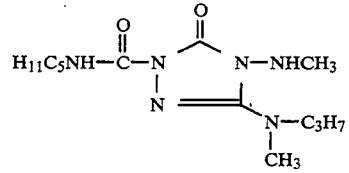

If, for example, 4-dimethylamino-5-diethylamino-2,4-dihydro-3H-1,2,4-triazol-3-one and N-benzyl-O-phenylurethane are used as the starting substances, the course of the reaction in process (d) according to the invention may be represented by the following equation:

$$H_5C_6-CH_2-NH-\overset{\overset{O}{\|}}{C}-O-C_6H_5 \; +$$

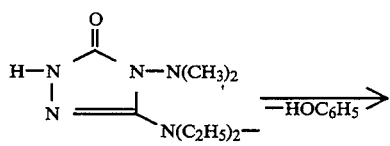

-continued

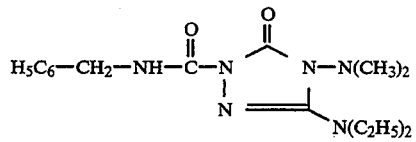

If, for example, 2-(1-methyl-1-phenyl-ethylamino-carbonyl)-4-ethoxymethyleneamino-5-(pyrrolidin-1-yl)-2,4-dihydro-3H-1,2,4-triazol-3-one and sodium boranate are used as the starting substances, the course of the reaction in process (e) according to the invention may be represented by the following equation:

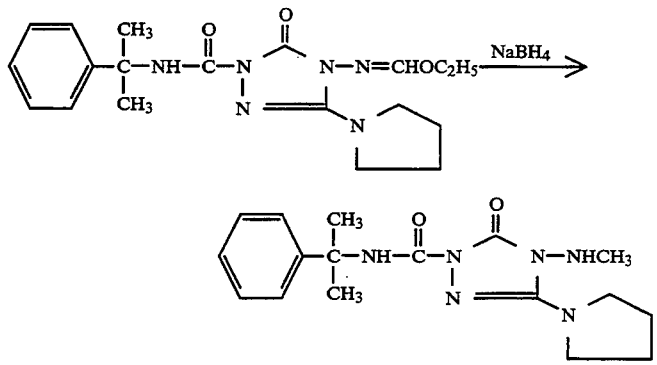

If, for example, 2-(1-methyl-1-trifluoromethyl-ethyl-amino-carbonyl)-4-isobutylideneamino-5-(N-methyl-propylamino)-2,4-dihydro-3H-1,2,4-triazol-3-one and sodium cyanoborohydride are used as the starting substances, the course of the reaction in process (f) according to the invention may be represented by the following equation:

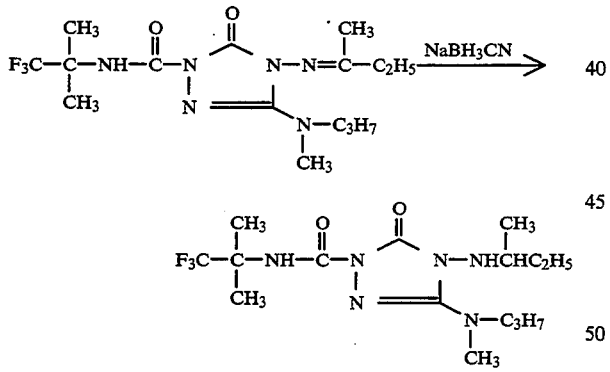

Formula (II) provides a general definition of the 4,5-diamino-1,2,4-triazol-3-ones to be used as the starting substances in processes (a) and (d) according to the invention for the preparation of compounds of the formula (I).

In formula (II), $R^2$, $R^3$, $R^4$, $R^5$ and Y preferably, or in particular, have those meanings which have already been mentioned above in connection with the description of the compounds of the formula (I) according to the invention as being preferred, or particularly preferred, for $R^2$, $R^3$, $R^4$, $R^5$ and Y.

The 4,5-diamino-1,2,4-triazol-3-(thi)ones of the formula (II) are known and/or can be prepared by processes known per se (cf. Advan. Heterocycl. Chem. 5 (1965), 119–204; Chem. Ber. 99 (1966), 81–84; J. Chem. Soc. 1952, 4817; J. Heterocycl. Chem. 2 (1965), 302–304; Eur. J. Med. Chem.—Chim. Ther. 21 (1986), 235–244; J. Chem. Soc. C 1968, 2099–2107; J. Chem. Soc. C 1970, 26–34 Liebigs Ann. Chem. 702 (1967), 101–111; Liebigs Ann. Chem. 703 (1967), 116–130).

The 4,5-diamino-1,2,4-triazol-3-ones of the general formula (IIa)

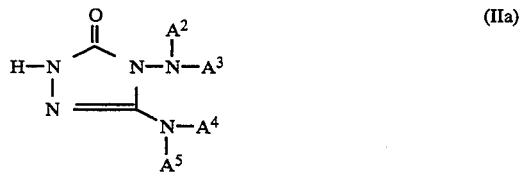

in which
$A^2$, $A^3$, $A^4$, and $A^5$ are identical or different and represent hydrogen, alkyl, alkenyl, alkinyl, halogenoalkyl, halogenoalkenyl, halogenoalkinyl, cyanoalkyl, alkoxyalkyl or alkylthioalkyl, or represent in each case optionally substituted cycloalkyl or cycloalkylalkyl, or two of these radicals together ($A^2$ and $A^3$ or $A^4$ and $A^5$) represent alkanediyl or oxaalkanediyl, and $A^5$ can also represent alkoxy, with the proviso that at least one of the radicals $A^2$, $A^3$, $A^4$ or $A^5$ is other than hydrogen, are new.

Preferred new compounds of the formula (IIa) are those in which $A^2$, $A^3$, $A^4$ and $A^5$ are identical or different and represent hydrogen, or represent in each case straight-chain or branched alkyl having 1 to 8 carbon atoms, alkenyl having 2 to 8 carbon atoms, alkinyl having 2 to 8 carbon atoms, halogenoalkyl having 1 to 8 carbon atoms and 1 to 17 identical or different halogen atoms, halogenoalkenyl or halogenoalkinyl, in each case having 2 to 8 carbon atoms and 1 to 15, or 13, identical or different halogen atoms, cyanoalkyl having 1 to 8 carbon atoms, alkoxyalkyl or alkylthioalkyl, in each case having up to 4 carbon atoms in the individual alkyl moieties, or represent cycloalkyl or cycloalkylalkyl, each of which has 3 to 8 carbon atoms in the cycloalkyl moiety and, where appropriate, 1 to 6 carbon atoms in the alkyl moiety and each of which is optionally monosubstituted to trisubstituted by identical or different substituents, suitable substituents in each case being: halogen, cyano, as well as in each case straight-chain or branched alkyl or halogenoalkyl, in each case having 1 to 4 carbon atoms and, where appropriate, 1 to 9 identical or different halogen atoms, in which formula furthermore in each case two of these radicals together—$A^2$ and $A^3$ or $A^4$ and $A^5$—can also represent straight-chain or branched alkanediyl or oxaalkanediyl each having 2 to 6 carbon atoms, and $A^5$ can also represent straight-chain or branched alkoxy having 1 to 8 carbon atoms, with the proviso that at least one of the radicals $A^2$, $A^3$, $A^4$ or $A^5$ is other than hydrogen.

Particularly preferred new compounds of the formula (IIa) are those in which $A^2$ represents hydrogen, methyl, ethyl, propyl, isopropyl, butyl, isobutyl, sec-butyl, allyl, propargyl, cyanoethyl, methoxyethyl, cyclopropyl, cyclopentyl or cyclohexyl, $A^3$ represents hydrogen, methyl, ethyl, propyl, butyl, allyl, propargyl, cyanoethyl or methoxyethyl, or together with $A^2$ represents butane-1,4-diyl or pentane-1,5-diyl, $A^4$ represents hydrogen, methyl, ethyl, propyl, isopropyl, butyl, isobutyl, sec-butyl, allyl, propargyl, cyanoethyl, methoxyethyl, cyclopropyl, cyclopentyl or cyclohexyl, and $A^5$ represents methyl, ethyl, propyl, butyl, allyl, propargyl, cyanoethyl, methoxyethyl or methoxy, or together with $A^4$ represents butane-1,4-diyl, pentane-1,5-diyl or 3-oxa-pentane-1,5-diyl.

The new compounds of the formula (IIa) are obtained when (α) amino or imino compounds of the general formulae (X), (XI) or (XII)

(X)

(XI)

(XII)

in which $A^4$ and $A^5$ have the abovementioned meanings,
$X^1$ represents halogen and
$Z^1$, $Z^2$, $Z^3$, $Z^4$, and $Z^5$ represent leaving groups customary in the chemistry of carbonic acids, are reacted with carbodihydrazide derivatives of the general formulae (XIIIa) or (XIIIb)

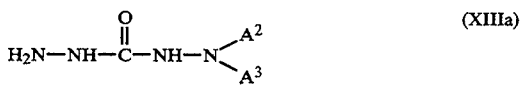

(XIIIa)

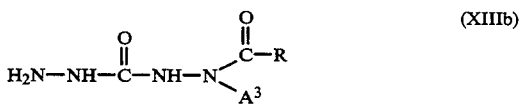

(XIIIb)

in which $A^2$ and $A^3$ have the abovementioned meanings and
R represents alkyl, alkoxy or aryl, if appropriate in the presence of a diluent, such as, for example, phenol and/or chlorobenzene, if appropriate in the presence of a catalyst, such as, for example, dibutyltin oxide, and if appropriate in the presence of an acid acceptor, such as, for example, sodium carbonate, at temperatures between 20° C. and 200° C., if appropriate the group —CO—R is subsequently split off at temperatures between 20° C. and 120° C. by reaction of the product with an aqueous hydroxide solution, such as, for example, sodium hydroxide solution, and the product is worked up by customary methods (cf. the Preparation Examples), or when (β) diaminoguanidine derivatives of the general formula (XIV)

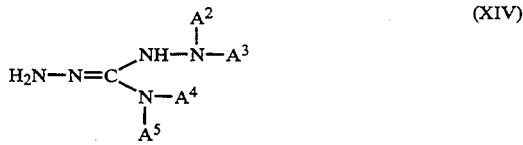

(XIV)

in which $A^2$, $A^3$, $A^4$ and $A^5$ have the abovementioned meanings, or acid adducts of compounds of the formula (XIV) or tautomers of compounds of the formula (XIV) are reacted with carbonic acid derivatives of the general formula (XV)

(XV)

in which $Z^1$ and $Z^2$ have the abovementioned meanings, if appropriate in the presence of a diluent, such as, for example, phenol, and if appropriate in the presence of an acid acceptor, such as, for example, sodium carbonate, at temperatures between 20° C. and 200° C., and the product is worked up by customary methods (cf. the Preparation Examples).

In formulae (X), (XI) and (XII), $A^4$ and $A^5$ preferably, or in particular, have those meanings which have already been mentioned above in the description of the compounds of the formula (IIa) as being preferred, or particularly preferred, for $A^4$ and $A^5$ and $Z^1$, $Z^2$, $Z^3$, $Z^4$ and $Z^5$ are identical or different and preferably represent halogen, $C_1$-$C_4$-alkoxy, $C_1$-$C_4$-alkylthio, $C_1$-$C_4$-alkylamino, di-($C_1$-$C_2$-alkyl)-amino, phenoxy or phenylthio, in particular chlorine, methoxy, ethoxy, methylthio, ethylthio, methylamino, ethylamino, dimethylamino or phenoxy.

If appropriate the leaving groups from the series $Z^1$ to $Z^5$ can also be linked. In this case, $Z^1$ and $Z^2$ or $Z^3$ and $Z^4$ together preferably represent $C_2$-$C_4$-alkanedioxy, in particular ethane-1,2-dioxy (—OCH$_2$CH$_2$O—).

The compounds of the formulae (X), (XI) and (XII) are known and/or can be prepared by processes known per se (cf. Synthesis 1977, 73–90; loc. cit. 1988, 460–466; J. Chem. Soc. 1951, 2492–2494; Chem. Ber. 120 (1987), 339–344; Tetrahedron Lett. 1982, 3539–3542; Houben-Weyl, Methoden der Organischen Chemie [Methods of Organic Chemistry], 4th Edition, Vol. E4 (1983), 522–624 and 652–722).

In formulae (XIIIa) and (XIIIb), $A^2$ and $A^3$ preferably, or in particular, have those meanings which have already been mentioned above in the description of the compounds of the formula (IIa) as being preferred, or particularly preferred, for $A^2$ and $A^3$, and R preferably represents $C_1$-$C_4$-alkyl, $C_1$-$C_4$-alkoxy or phenyl, in particular methyl, ethyl, methoxy or ethoxy.

With the exception of carbodihydrazide ($A^2=A^3=H$), the carbodihydrazide derivatives of the formula (XIIIa) were hitherto unknown from the literature.

The new compounds of the formula (XIIIa) are obtained when carbonic acid derivatives of the formula (XV)

$$Z^1-\overset{\overset{O}{\|}}{C}-Z^2 \quad \text{(XV)}$$

in which $Z^1$ and $Z^2$ have the abovementioned meanings, are reacted in succession with about one mole equivalent of a hydrazine derivative of the formula (XVI)

$$H_2N-N\overset{A^2}{\underset{A^3}{\diagdown}} \quad \text{(XVI)}$$

in which

A² and A³ have the abovementioned meanings and about one mole equivalent of hydrazine or hydrazine hydrate, at temperatures between 0° C. and 100° C. The product can then be worked up by customary methods. However, it is preferred not to isolate the compounds of the formula (XIIIa) in pure form but to react them further directly.

The carbodihydrazide derivatives of the formula (XIIIb) were hitherto unknown from the literature. The new compounds of the formula (XIIIb) are obtained when hydrazine derivatives of the formula (XVIa)

$$H_2N-N\overset{H}{\underset{A^3}{\diagdown}} \quad \text{(XVIa)}$$

in which

A³ has the abovementioned meaning, are reacted with acylating agents of the formula (XVII)

$$X^2-\overset{\overset{O}{\|}}{C}-R \quad \text{(XVII)}$$

in which

R has the abovementioned meaning and

X² represents halogen or the group —O—CO—R, if appropriate in the presence of a diluent, such as, for example, methanol, methylene chloride or toluene, and if appropriate in the presence of an acid acceptor, such as, for example, potassium carbonate or pyridine, at temperatures between −80° C. and +80° C., the resulting acylated hydrazines of the general formula (XVIII)

$$H_2N-N\overset{\overset{O}{\overset{\|}{C}-R}}{\underset{A^3}{\diagdown}} \quad \text{(XVIII)}$$

in which

A³ and R have the abovementioned meanings, are reacted with carbonic acid derivatives of the general formula (XV)

$$Z^1-\overset{\overset{O}{\|}}{C}-Z^2 \quad \text{(XV)}$$

in which $Z^1$ and $Z^2$ have the abovementioned meanings, if appropriate in the presence of a diluent, such as, for example, methylene chloride or ethylene chloride, and if appropriate in the presence of an acid acceptor, such as, for example, sodium carbonate, at temperatures between −20° C. and +80° C., and the resulting diacylated hydrazines of the formula (XIX)

$$Z^2-\overset{\overset{O}{\|}}{C}-NH-N\overset{\overset{O}{\overset{\|}{C}-R}}{\underset{A^3}{\diagdown}} \quad \text{(XIX)}$$

in which

A³, R and Z², have the abovementioned meanings, are reacted with hydrazine or hydrazine hydrate, if appropriate in the presence of a diluent, such as, for example, chlorobenzene, at temperatures between 0° C. and 120° C. (cf. the Preparation Examples).

The compounds of the formulae (XV), (XVI), (XVIa) and (XVII) which are required as precursors are known chemicals for organic synthesis.

In formula (XIV), A², A³, A⁴ and A⁵ preferably, or in particular, have those meanings which have already been mentioned above in the description of the compounds of the formula (IIa) as being preferred, or particularly preferred, for A², A³, A⁴ and A⁵.

The compounds of the formula (XIV) are known and/or can be prepared by processes known per se (cf. EP-A 150,677).

In formula (XV), $Z^1$ and $Z^2$ are identical or different and in each case preferably represent halogen, $C_1$-$C_4$-alkoxy, $C_1$-$C_4$-alkylthio, $C_1$-$C_4$-alkylamino, Di-($C_1$-$C_2$-alkyl)amino, phenoxy or phenylthio, in particular chlorine, methoxy, ethoxy, phenoxy, methylthio or dimethylamino. $Z^1$ and $Z^2$ can also be cyclically linked. In this case, $Z^1$ and $Z^2$ together preferably represent $C_2$-$C_4$-alkanedioxy, in particular ethane-1,2-dioxy(—OCH₂C-H₂O—). The compounds of the formula (XV) are known chemicals for organic synthesis.

Formula (III) provides a general definition of the iso(thio)cyanates furthermore to be used as the starting substances in process (a) according to the invention.

In formula (III), R¹ and X preferably, or in particular, have those meanings which have already been mentioned above in connection with the description of the compounds of the formula (I) according to the invention as being preferred, or particularly preferred, for R¹ and X.

The iso(thio)cyanates of the formula (III) are known chemicals for organic synthesis.

Formula (IV) provides a general definition of the 4-alkylideneamino-5-amino-1,2,4-triazol(e)-3-(thi)ones to be used as starting substances in processes (b) and (f) according to the invention for the preparation of compounds of the formula (I).

In formula (IV), R¹, R⁴, R⁵, X and Y preferably, or in particular, have those meanings which have already been mentioned above in connection with the description of the compounds of the formula (I) according to the invention as being preferred, or particularly preferred, for $R^1$, $R^4$, $R^5$, X and Y, and $R^6$ and $R^7$ in each case independently of one another preferably represent hydrogen, straight-chain or branched alkyl having 1 to 4 carbon atoms, phenyl or benzyl.

The 4-alkylideneamino-5-amino-1,2,4-triazol-3-(thi)ones of the formula (IV) were hitherto unknown from the literature.

The new compounds of the formula (IV) are obtained when the above-described 4,5-diamino-1,2,4-triazol-3-(thi)ones of the general formula (II)

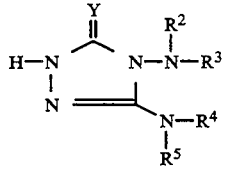
(II)

in which
$R^2$, $R^3$, $R^4$, $R^5$ and Y have the abovementioned meanings with the proviso that $R^2$ and $R^3$ represent hydrogen, are reacted with aldehydes or ketones of the formula (XX)

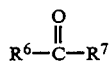
(XX)

in which
$R^6$, and $R^7$ have the abovementioned meanings, if appropriate in the presence of a diluent, such as, for example, methylene chloride or toluene, and if appropriate in the presence of a catalyst, such as, for example, p-toluenesulphonic acid, at temperatures between 20° C. and 120° C., and the resulting 4-alkylideneamino-5-amino-1,2,4-triazol-3-(thi)ones of the formula (XXI)

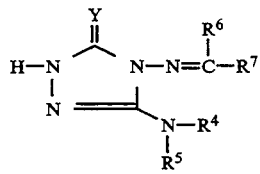
(XXI)

in which
$R^4$, $R^5$, $R^6$, $R^7$ and Y have the abovementioned meanings, are either reacted, in a subsequent second step, with iso(thio)cyanates of the formula (III)

(III)

in which
$R^1$ and X have the abovementioned meanings, if appropriate in the presence of a diluent, such as, for example, methylene chloride or dioxane, and if appropriate in the presence of a reaction auxiliary, such as, for example, triethylamine, at temperatures between 20° C. and 150° C., or when, alternatively, in a second step, the compounds of the formula (XXI) are reacted with chloro(thio)formic esters of the formula (XXII)

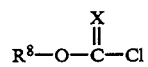
(XXII)

in which

X has the abovementioned meaning and
$R^8$ represents alkyl, aryl or aralkyl, if appropriate in the presence of a diluent, such as, for example, tetrahydrofuran, and if appropriate in the presence of a reaction auxiliary, such as, for example, sodium hydride or potassium tert-butylate, at temperatures between $-20°$ C. and $+40°$ C., and the resulting 2-oxy(thio)-carbonyl-4-alkylideneamino-5-amino-1,2,4-triazol-3-(thi)ones of the formula (XXIII)

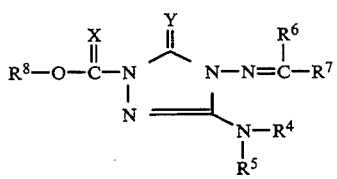
(XXIII)

in which
$R^4$, $R^5$, $R^6$, $R^7$, $R^8$, X and Y have the abovementioned meanings, are reacted, in a subsequent third step, with amines of the formula (VI)

(VI)

in which
$R^1$ has the abovementioned meaning, if appropriate in the presence of a diluent, such as, for example, tetrahydrofuran or dioxane, and if appropriate in the presence of a base, such as, for example, sodium hydroxide or potassium hydroxide, at temperatures between 20° C. and 100° C.

It is possible here, and may be advantageous, to carry out the reaction of compounds of the formula (XXI) with chloro(thio)formic esters and the subsequent reaction with amines in so-called one-pot processes.

The aldehydes or ketones of the formula (XX), the iso(thio)cyanates of the formula (III), the chloro(thio)formic esters of the formula (XXII) and the amines of the formula (VI) are known chemicals for organic synthesis.

The 4-alkylideneammino-5-amino-1,2,4-triazol-3-(thi)ones of the formula (XXI)—with the proviso that $R^4$ and/or $R^5$ are other than hydrogen—and the 2-oxy-(thio)carbonyl-4-alkylideneamino-5-amino-1,2,4-triazol-3-(thi)ones of the formula (XXIII) were hitherto unknown from the literature and are the subject matter of the present patent application.

In formulae (XXI) and (XXIII), $R^4$, $R^5$, $R^6$, $R^7$ and Y preferably, or in particular, have those meanings which have been mentioned above in the description of the compounds of the formula (IV) according to the invention as being preferred, or particularly preferred, for $R^4$, $R^5$, $R^6$, $R^7$ and Y and $R^8$ preferably represents methyl, ethyl, propyl, isopropyl, butyl, isobutyl, sec-butyl, tert-butyl, phenyl or benzyl.

Formula (V) provides a general definition of the substituted 1,2,4-triazol-3-(thi)ones to be used as starting substances in process (c) according to the invention for the preparation of compounds of the formula (I).

In formula (V), $R^2$, $R^3$, $R^4$, $R^5$, X and Y preferably, or in particular, have those meanings which have already been mentioned above in connection with the description of the compounds of the formula (I) according to the invention as being preferred, or particularly preferred, for $R^2$, $R^3$, $R^4$, $R^5$, X and Y, and
$R^8$ preferably represents methyl, ethyl, propyl, isopropyl, butyl, isobutyl, sec-butyl, tert-butyl, phenyl or benzyl.

The substituted 1,2,4-triazol-3-(thi)ones of the formula (V) were hitherto unknown from the literature. The new compounds of the formula (V) are obtained when 4,5-diamino-1,2,4-triazol(e)-3-(thi)ones of the formula (II)

$$\begin{array}{c} Y \\ \| \\ H-N \end{array} \begin{array}{c} R^2 \\ | \\ N-N-R^3 \\ | \\ N \end{array} \begin{array}{c} \\ \\ N-R^4 \\ | \\ R^5 \end{array} \quad (II)$$

in which

R², R³, R⁴, R⁵ and Y have the abovementioned meanings, are reacted with chloro(thio)formic esters of the formula (XXII)

$$\begin{array}{c} X \\ \| \\ R^8-O-C-Cl \end{array} \quad (XXII)$$

in which

R⁸ and X have the abovementioned meanings, if appropriate in the presence of a diluent, such as, for example, tetrahydrofuran, and if appropriate in the presence of an acid acceptor, such as, for example, potassium tert-butylate, at temperatures between −20° C. and +100° C.

Formula (VI) provides a general definition of the amino compounds furthermore to be used as starting substances in process (c) according to the invention.

In formula (VI), R¹ preferably, or in particular, has the meaning which has already been mentioned above in connection with the description of the compounds of the formula (I) according to the invention as being preferred, or particularly preferred, for R¹.

Formula (VII) provides a general definition of the (thio)urethanes to be used as starting substances in process (d) according to the invention for the preparation of compounds of the formula (I).

In formula (VII), R¹ and X preferably, or in particular, have those meanings which have already been mentioned above in connection with the description of the compounds of the formula (I) according to the invention as being preferred, or particularly preferred for R¹ and X, and R⁹ preferably represents methyl, ethyl, propyl, isopropyl, butyl, isobutyl, sec-butyl, tert-butyl, phenyl or benzyl.

The starting substances of the formula (VII) are known chemicals for organic synthesis.

Formula (VIII) provides a general definition of the 4-oxyalkylideneamino-5-amino-1,2,4-triazol(thi)ones to be used as starting substances in process (e) according to the invention for the preparation of compounds of the formula (I).

In formula (VIII), R¹, R⁴, R⁵, X and Y preferably, or in particular, have those meanings which have already been mentioned above in connection with the description of the compounds of the formula (I) according to the invention as being preferred, or particularly preferred, for R¹, R⁴, R⁵, X and Y, and R¹⁰ and R¹¹ preferably represent hydrogen, C₁-C₆-alkyl, C₂-C₆-alkenyl, C₂-C₆-alkinyl, C₃-C₆-cycloalkyl, phenyl or benzyl.

In particular, R¹⁰ represents hydrogen, methyl, ethyl, propyl, phenyl or benzyl and R¹¹ represents methyl, ethyl, propyl or benzyl.

The 4-oxyalkylideneamino-5-amino1,2,4-triazol(e)-3-(thi)ones of the formula (VIII) were hitherto unknown from the literature.

The new compounds of the formula (VIII) are obtained when 4,5-diamino-1,2,4-triazol-3-(thi)ones of the general formula (II)

$$\begin{array}{c} Y \\ \| \\ H-N \end{array} \begin{array}{c} R^2 \\ | \\ N-N-R^3 \\ | \\ N \end{array} \begin{array}{c} \\ \\ N-R^4 \\ | \\ R^5 \end{array} \quad (II)$$

in which

R² and R³ represent hydrogen and Y, R⁴ and R⁵ have the abovementioned meanings, are reacted with orthocarboxylic esters of the general formula (XXIV)

$$R^{10}-C(OR^{11})_3 \quad (XXIV)$$

in which

R¹⁰ and R¹¹ have the abovementioned meanings, if appropriate in the presence of a diluent, such as, for example, chloroform, toluene or chlorobenzene, and if appropriate in the presence of a catalyst, such as, for example, p-toluenesulphonic acid, at temperatures between 50° C. and 200° C., and the resulting oxyalkylidene compounds of the formula (XXV)

$$\begin{array}{c} Y \\ \| \\ H-N \end{array} \begin{array}{c} R^{10} \\ | \\ N-N=C-O-R^{11} \\ | \\ N \end{array} \begin{array}{c} \\ \\ N-R^4 \\ | \\ R^5 \end{array} \quad (XXV)$$

in which

R⁴, R⁵, R¹⁰, R¹¹ and Y have the abovementioned meanings, are reacted, in a subsequent second step, with iso(thio)-cyanates the formula (III)

$$R^1-N=C=X \quad (III)$$

in which

R¹ and X have the abovementioned meanings, if appropriate in the presence of a diluent, such as, for example, methylene chloride or dioxane, and if appropriate in the presence of a reaction auxiliary, such as, for example, triethylamine, at temperatures between 20° C. and 150° C.

Alternatively, the compounds of the formula (VIII) are also obtained when compounds of the formula (I)

$$\begin{array}{c} X \\ \| \\ R^1-NH-C-N \end{array} \begin{array}{c} Y \\ \| \\ \\ N \end{array} \begin{array}{c} R^2 \\ | \\ N-N-R^3 \\ | \\ \\ N-R^4 \\ | \\ R^5 \end{array} \quad (I)$$

in which $R^2$ and $R^3$ represent hydrogen and
$R^1$, $R^4$, $R^5$, X and Y have the abovementioned meanings, are reacted with orthocarboxylic esters of the formula (XXIV)

$$R^{10}-C(OR^{11})_3 \quad (XXIV)$$

in which $R^{10}$ and $R^{11}$ have the abovementioned meanings, if appropriate in the presence of a diluent, such as, for example, chloroform, toluene or chlorobenzene, and if appropriate in the presence of a catalyst, such as, for example, p-toluenesulphonic acid, at temperatures between 50° C. and 200° C.

The orthocarboxylic esters of the formula (XXIV) are known chemicals for organic synthesis.

The oxyalkylidene compounds of the formula (XXV) were hitherto unknown from the literature and are the subject-matter of the present patent application.

In formula (XXV), $R^4$, $R^5$ and Y preferably, or in particular, have those meanings which have been mentioned above in the description of the compounds of the formula (I) according to the invention as being preferred, or particularly preferred, for $R^4$, $R^5$ and Y, and $R^{10}$ and $R^{11}$ preferably represent $C_1$-$C_6$-alkyl, $C_2$-$C_6$-alkenyl, $C_2$-$C_6$-alkinyl, $C_3$-$C_6$-cycloalkyl, phenyl or benzyl; $R^{10}$ also represents hydrogen; in particular, $R^{10}$ represents hydrogen, methyl, ethyl, propyl, phenyl or benzyl and $R^{11}$ represents methyl, ethyl, propyl or benzyl.

The hydride complexes of the formula (IX) furthermore required as starting substances in process (e) are known chemicals for synthesis.

Process (a) according to the invention is preferably carried out in the presence of a diluent.

Suitable diluents for carrying out process (a) according to the invention are, in particular, inert organic solvents. These include, for example, aliphatic, alicyclic or aromatic, optionally halogenated hydrocarbons, such as benzine, benzene, toluene, xylene, chlorobenzene, petroleum ether, hexane, cyclohexane, dichloromethane, chloroform, carbon tetrachloride, ethers, such as diethyl ether, dioxane, tetrahydrofuran, ethylene glycol dimethyl ether or ethylene glycol diethyl ether, nitriles, such as acetonitrile or propionitrile, amides, such as dimethylformamide, dimethylacetamide, N-methylformanilide, N-methylpyrrolidone or hexamethylphosphoric triamide, or esters, such as ethyl acetate.

If appropriate, process (a) according to the invention is carried out in the presence of a suitable reaction auxiliary. Suitable reaction auxiliaries are all customary inorganic or organic bases. These include, for example, tertiary amines, such as triethylamine, N,N-dimethylaniline, N,N-diethylbenzylamine, N,N-dimethylcyclohexylamine or dibutyltin dilaureate, pyridine, N,N-dimethylaminopyridine, diazabicyclooctane (DABCO), diazabicyclononene (DBN) or diazabicycloundecene (DBU).

When carrying out process (a) according to the invention, the reaction temperatures can be varied within a substantial range. In general, the process is carried out at temperatures between 0° C. and 150° C., preferably at temperatures between 10° C. and 100° C.

For carrying out process (a) according to the invention, 1.0 to 2.0 moles, preferably 1.0 to 1.5 moles, of iso(thio)cyanate of the formula (III) and if appropriate 0.001 to 2.0 moles, preferably 0.001 to 1.0 mole, of reaction auxiliary are generally employed per mole of 4,5-diamino-1,2,4-triazol(e)-3-(thi)one of the formula (II). The reaction is carried out and the reaction products are worked up and isolated by generally customary methods.

Suitable acids for carrying out process (b) according to the invention are all inorganic and organic acids which can customarily be used for hydrazone cleavages. Inorganic mineral acids, such as hydrochloric acid, sulphuric acid or phosphoric acid, are preferably used.

Suitable diluents for carrying out process (b) according to the invention are all customary organic or inorganic solvents. Polar organic solvents which are miscible with water, in particular alcohols, such as methanol, ethanol, propanol or butanol, their mixtures with water, or pure water, are preferably used as diluents.

When carrying out process (b) according to the invention, the reaction temperatures can be varied within a substantial range. In general, the process is carried out at temperatures between 20° C. and 150° C., preferably at temperatures between 50° C. and 120° C.

Process (b) according to the invention is generally carried out under atmospheric pressure or under reduced pressure. If the process is carried out under reduced pressure, suitable pressure ranges are those between 20 and 400 mbar, preferably between 100 and 200 mbar.

For carrying out process (b) according to the invention, 0.01 to 50 moles, preferably 0.1 to 20 moles, of an acid are generally employed per mole of 4-alkylideneamino-5-amino-1,2,4-triazol-3-(thi)one of the formula (IV).

In general, the compound of the formula (IV) is dissolved in a suitable diluent, the required amount of acid is then added, and the mixture is slowly concentrated under reduced pressure in the course of several hours.

In a particular procedure variant, it is also possible to carry out the process (b) according to the invention as well as the preparation of the precursors of the formula (IV) which are required for process (b), in one reaction step in a so-called one-pot process.

Here, it is possible to select the compounds of the formula (XXIII) as starting substances and to react these in succession in a one-pot process with amines of the formula (VI) and subsequently with acid according to process (b) according to the invention, or, alternatively, to select the compounds of the formula (XXI) as starting substances and to react these in succession in a one-pot process with (thio)chloroformic esters of the formula (XXII), then with amines of the formula (VI) and subsequently with acid according to process (b) according to the invention.

Suitable diluents for carrying out the process (c) according to the invention are inert organic solvents. These include, in particular, aliphatic, alicyclic or aromatic, optionally halogenated hydrocarbons, such as, for example, benzine, benzene, toluene, xylene, chlorobenzene, petroleum ethers hexane, cyclohexane, dichloromethane, chloroform, carbon tetrachloride, ethers, such as diethyl ether, dioxane, tetrahydrofuran, ethylene glycol dimethyl ether or ethylene glycol diethyl ether, nitriles, such as acetonitrile or propionitrile, amides, such as dimethylformamide, dimethylacetamide, N-methylformanilide, N-methylpyrrolidone or hexamethylphosphoric triamide, or esters, such as ethyl acetate, or sulphoxides, such as dimethyl sulphoxide.

If appropriate, process (c) according to the invention can be carried out in the presence of a suitable reaction auxiliary. Suitable reaction auxiliaries are all customary inorganic or organic bases. These include, for example, alkali metal hydroxides, such as sodium hydroxide or potassium hydroxide, alkali metal carbonates, such as sodium carbonate, potassium carbonate or sodium hydrogen carbonate, and also tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

When carrying out process (c) according to the invention, the reaction temperatures can be varied within a substantial range. In general, the process is carried out at temperatures between 0° C. and 120° C., preferably at temperatures between 20° C. and 50° C.

For carrying out process (c) according to the invention, 1 to 5 moles, preferably 1.0 to 2.5 moles, of amino compound of the formula (VI) and if appropriate 0.1 to 2 moles, preferably 1.0 to 1.2 moles, of reaction auxiliary are generally employed per mole of substituted 1,2,4-triazol-3-(thi)one of the formula (V).

The reaction is carried out and the reaction products are worked up and isolated by generally customary methods.

In a particular procedure variant, it is also possible to carry out process (c) according to the invention and the preparation of the precursors of the formula (V) required for process (c), in one reaction step in a so-called one-pot process.

For this purpose, the starting compounds are compounds of the formula (II), which are reacted in succession in a one-pot process, first with (thio)chloroformic esters of the formula (XXII) and then with amines of the formula (VI) according to process (c) according to the invention.

Process (d) according to the invention is preferably carried out in the presence of a diluent. In this context, the same solvents can be used as have been indicated above in process (a) according to the invention.

Process (d) is preferably carried out in the presence of a reaction auxiliary. In this context, the same reaction auxiliaries can be employed as have been indicated above in process (c) according to the invention.

When carrying out process (d) according to the invention, the reaction temperatures can be varied within a substantial range. In general, the process is carried out at temperatures between 0° C. and 150° C., preferably at temperatures between 10° C. and 120° C.

For carrying out process (d) according to the invention, 1 to 2 moles, preferably 1.0 to 1.5 moles, of (thio)urethane of the formula (VII) are generally employed per mole of 4,5-diamino-1,2,4-triazol-3-(thi)one of the formula (II).

The reaction is carried out and the products of the formula (I) are worked up and isolated by generally customary methods.

Process (e) according to the invention is preferably carried out in the presence of a polar solvent. Preferred polar solvents which are possible are water, alcohols, such as methanol, ethanol, propanol, isopropanol, butanol, isobutanol, sec-butanol and tert-butanol, ether alcohols, such as methoxyethanol and ethoxyethanol, or ethers, such as diethyl ether, dipropyl ether, diisopropyl ether, tetrahydrofuran and dioxane.

In the second step of process (e), the reaction temperatures can be varied within a substantial range. In general, this step is carried out at temperatures between −20° C. and +100° C., preferably between 0° C. and +30° C.

For carrying out process (e) according to the invention, 0.5 to 5 moles, preferably 1 to 3 moles, of hydride complex of the formula (IX) are generally employed per mole of 4-oxyalkylideneamino-5-amino-1,2,4-triazol-3-(thi)one of the formula (VIII).

The reaction is carried out and the reaction products are worked up and isolated by generally customary methods.

Process (f) according to the invention is carried out using a reducing agent and if appropriate a catalyst. Suitable systems of reducing agents and catalysts are, for example, hydrogen in combination with customary hydrogenation catalysts, such as, for example, Raney-Nickel, palladium or platinum, furthermore also, if appropriate, complex metal hydrides, such as, for example, lithium alanate, sodium borahate and sodium cyanoborohydride, if appropriate in combination with acid catalysts, such as, for example, hydrochloric acid or acetic acid.

Process (f) is preferably carried out in the presence of a diluent. For this purpose, the same solvents can be used which have been indicated above in process (e) according to the invention.

When carrying out process (f) according to the invention, the reaction temperatures can be varied within a substantial range. In general, the process is carried out at temperatures between −20° C. and +100° C., preferably at temperatures between 0° C. and +30° C.

The reaction is carried out and the reaction products are worked up and isolated by customary methods.

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera

Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutlion, Emex, Datura, Viola, Galeopsis, Papaver and Centaurea.

Dicotyledon Cultures of the genera

Gossypium, Glycine, Beta, Daucus, phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera

Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera

Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total Combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The compounds of the formula (I) according to the invention are suitable for selectively combating monocotyledon and dicotyledon weeds, in particular in monocotyledon cultures, in both the pre-emergence and the post-emergence method. The compounds according to the invention are very well tolerated by corn in particular when the post-emergence method is used.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use Of water as an extender, organic solvents can, for example, also be used as auxiliary solvents. As liquid solvents, there are suitable in the main: aromatics, such as xylene, toluene, or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as album in hydrolysis products; as dispersing agents there are suitable: for example ligninsulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

For combating weeds, the active compounds according to the invention, as such or in the form of their formulations, can also be used as mixtures with known herbicides, finished formulations or tank mixes being possible.

Suitable herbicides for the mixtures are known herbicides, such as, for example, 1-amino-6-ethylthio-3(2,2-dimethylpropyl)-1,3,5-triazine-2,4(1H,3H)-dione (AMETHYDIONE) or N-(2-benzothiazolyl)-N,N'-dimethylurea (METABENZTHIAZURON) for combating weeds in cereals; 4-amino-3-methyl-6-phenyl-1,2,4-triazin-5(4H)-one (METAMITRON) for combating weeds in sugar beets, and 4-amino-6-(1,1-dimethylethyl)-3-methylthio-1,2,4-triazin-5(4H)-one (METRIBUZIN) for combating weeds in soy beans; furthermore also 2,4-dichlorophenoxyacetic acid (2,4-D); 4-(2,4-dichlorophenoxy)-butyric acid (2,4-DB); 2,4-dichlorophenoxypropionic acid (2,4-DP); N-(methoxymethyl)-2,6-diethyl-chloroacetanilide (ALACHLOR); 2-chloro-4-ethylamino-6-isopropylamino-1,3,5-triazine (ATRAZINE); 3-isopropyl-2,1,3-benzothiadiazin-4-one 2,2-dioxide (BENTAZONE); methyl 5-(2,4-dichlorophenoxy)-2-nitrobenzoate (BIFENOX); 3,5-dibromo-4-hydroxy-benzonitrile(BROMOXYNIL); 2-chloro-N{[(4-methoxy-6-methyl-1,3,5-triazin-2-yl)-amino]-carbonyl}-benzenesulphonamide (CHLORSULFURON); N,N-dimethyl-N'-(3-chloro-4-methylphenyl)-urea (CHLORTOLURON); 2-chloro-4-ethyl-amino-6-(3-cyanopropylamino)-1,3,5-triazine (CYANAZINE); 2-[4-(2,4-dichlorophenoxy)-phenoxy]-propionic acid, its methyl ester or its ethyl ester (DICLOFOP); 4-amino-6-t-butyl-3-ethylthio-1,2,4-triazin-5(4H)-one(ETHIOZIN);2-{4-[(6-chloro-2-benzoxazolyl)-oxy]-phenoxy}-propanoic acid, its methyl ester or its ethyl ester (FENOXAPROP); [(4-amino-3,5-dichloro-6-fluoro-2-pyridinyl)-oxy]-acetic acid or its 1-methylheptyl ester (FLUROXYPYR); methyl 2-[4,5-dihydro-4-methyl-4-(1-methylethyl)-5-oxo-1H-imidazol-2yl]-4(5)-methylbenzoate (IMAZAMETHABENZ); 3,5-diiodo-4-hydroxybenzonitrile (IOXYNIL); N,N-dimethyl-N'-(4-isopropylphenyl)-urea (ISOPROTURON); (2-methyl-4-chlorophenoxy)-acetic acid (MCPA); (4-chloro-2-methyl-phenoxy)-propionic acid (MCPP); N-methyl-2-(1,3-benzothiazol-2-yloxy)-acetanilide (MEFENACET); 2-ethyl-6-methyl-N-(1-methyl-2-methoxyethyl)-chloroacetanilide (METOLACHLOR); 2-{[[((4-methoxy-6-methyl-1,3,5-triazin-2-yl)-amino)-carbonyl]-amino]-sulphonyl}-benzoic acid or its methyl ester (METSULFURON); N-(1-ethylpropyl)-3,4-dimethyl-2,6-dinitroaniline(PENDIMETHALIN); 0-(6-chloro-3-phenyl-pyridazin-4-yl) S-octyl thiocarbonate (PYRIDATE); methyl 3-[[[[(4-methoxy-6-methyl-1,3,5-triazin-2-yl)-amino]-carbonyl]-amino]-sulphonyl]-thiophene-2-carboxylate (THIAMETURON); S-(2,3,3-trichloroallyl) N,N-diisopropylthiocarbamate (TRI- ALLATE). Surprisingly, some mixtures also show synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active Compound per hectare of soil surface, preferably between 0.05 and 5 kg per ha.

The preparation and use of the active compounds according to the invention can be seen from the following examples.

PREPARATION EXAMPLES

EXAMPLE 1

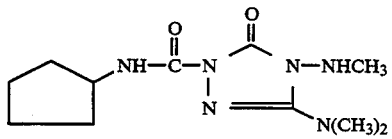

(Process (a))

2.3 g (20.7 mmol) of cyclopentyl isocyanate are added to a mixture of 3.2 g (20 mmol) of 4-methylamino5-dimethylamino-2,4-dihydro-3H-1,2,4-triazol-3-one, 80 ml of acetonitrile and 100 mg of diazabicycloundecene (DBU), and the reaction mixture is stirred for two days at 20° C. It is then concentrated, the residue is taken up in 100 ml of methylene chloride, and the mixture is washed with water, dried over sodium sulphate and filtered. The filtrate is concentrated, the residue is triturated with petroleum ether, and the product which is obtained in crystalline form is isolated by filtration with suction.

This gives 4.6 g (85% of theory) of 2-cyclopentyl aminocarbonyl-4-methylamino-5-dimethylamino-2,4-dihydro-3H-1,2,4-triazol-3-one of melting point 13;7 ° C.

EXAMPLE 2

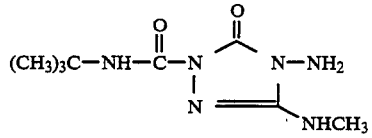

(Process (b))

4.6 g (15 mmol) of 2-tert-butylaminocarbonyl-4(4-methyl-2-pentylidene-amino)-5-methylamino-2,4-dihydro3H-1,2,4-triazol-3-one are taken up in a mixture of 50 ml of water and 50 ml of ethanol, and the mixture is treated with 2 ml of concentrated hydrochloric acid. The reaction mixture is slowly concentrated under a water pump vacuum, the residue is taken up in 50 ml of water/50 ml of ethanol, 2 ml of concentrated hydrochloric acid are added, and the mixture is again concentrated. The residue is then taken up in 150 ml of methylene chloride, and the mixture is washed with a 10% soda solution, dried over sodium sulphate and filtered. The filtrate is concentrated, the residue is triturated with petroleum ether, and the product which is obtained in crystallized form is isolated by filtration with suction.

This gives 1.0 g (29% of theory) of 2-tert-butylaminocarbonyl-4-amino-5-methylamino-2,4-dihydro-3H-1,2,4-triazol-3-one of melting point 174° C.

For example, the compounds of the formula (I)

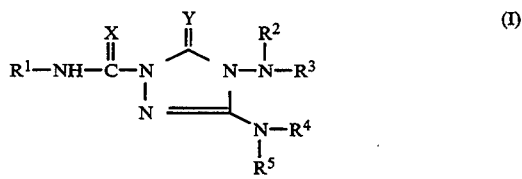

which are listed in Table 2 below can also be prepared analogously to Examples 1 and 2 and following the general description of the preparation processes according to the invention.

TABLE 2

| | Examples of the compounds of the formula (I) | | | | | | | |
|---|---|---|---|---|---|---|---|---|
| Ex. No. | R¹ | R² | R³ | R⁴ | R⁵ | X | Y | M.P. (°C.) |
| 3 | (CH₃)₃C— | H | CH₃ | CH₃ | CH₃ | O | O | 119 |
| 4 | ClCH₂C(CH₃)₂— | H | CH₃ | CH₃ | CH₃ | O | O | 142 |
| 5 | FCH₂C(CH₃)₂— | H | CH₃ | CH₃ | CH₃ | O | O | 129 |
| 6 | H₅C₂C(CH₃)₂— | H | CH₃ | CH₃ | CH₃ | O | O | 134 |
| 7 | (CH₃)₂CH— | H | CH₃ | CH₃ | CH₃ | O | O | 108 |
| 8 | H₇C₃C(CH₃)₂— | H | CH₃ | CH₃ | CH₃ | O | O | 163 |
| 9 | H₉C₄—C(CH₃)₂— | H | CH₃ | CH₃ | CH₃ | O | O | 143 |
| 10 | HC≡C—C(CH₃)₂— | H | CH₃ | CH₃ | CH₃ | O | O | 140 |
| 11 | ClCH₂CH(CH₃)— | H | CH₃ | CH₃ | CH₃ | O | O | 108 |
| 12 | cyclobutyl-CH₃ | H | CH₃ | CH₃ | CH₃ | O | O | 125 |

TABLE 2-continued

Examples of the compounds of the formula (I)

| Ex. No. | R¹ | R² | R³ | R⁴ | R⁵ | X | Y | M.P. (°C.) |
|---|---|---|---|---|---|---|---|---|
| 13 | 1-methylcyclohexyl | H | $CH_3$ | $CH_3$ | $CH_3$ | O | O | 154 |
| 14 | 1-ethylcyclohexyl | H | $CH_3$ | $CH_3$ | $CH_3$ | O | O | 126 |
| 15 | $C_6H_5$—$OCH_2CH(CH_3)$— | H | $CH_3$ | $CH_3$ | $CH_3$ | O | O | 88 |
| 16 | $ClCH_2C(CH_3)_2$— | H | H | H | $CH_3$ | O | O | 165 |
| 17 | $(CH_3)_3C$— | H | H | $CH_3$ | $CH_3$ | O | O | 142 |
| 18 | $FCH_2C(CH_3)_2$— | H | H | $CH_3$ | $CH_3$ | O | O | 122 |
| 19 | $ClCH_2C(CH_3)_2$— | H | H | $CH_3$ | $CH_3$ | O | O | 112 |
| 20 | $(CH_3)_3C$— | H | $CH_3$ | H | $CH_3$ | O | O | |
| 21 | $ClCH_2C(CH_3)_2$— | H | $CH_3$ | H | $CH_3$ | O | O | 200 |
| 22 | $HC\equiv C$—$C(CH_3)_2$— | H | H | $CH_3$ | $CH_3$ | O | O | 143 |
| 23 | cyclopentyl | H | H | $CH_3$ | $CH_3$ | O | O | 167 |
| 24 | $(CH_3)_2CH$— | H | H | $CH_3$ | $CH_3$ | O | O | $n_D^{20} = 1.5122$ |
| 25 | $ClCH_2$—$CH(CH_3)$— | H | H | $CH_3$ | $CH_3$ | O | O | $n_D^{20} = 1.5304$ |
| 26 | cyclopropyl | H | H | $CH_3$ | $CH_3$ | O | O | 139 |
| 27 | $(CH_3)_2CH$—$CH(CH_3)$— | H | H | $CH_3$ | $CH_3$ | O | O | $n_D^{20} = 1.5045$ |
| 28 | n-$C_3H_7$— | H | H | $CH_3$ | $CH_3$ | O | O | 134 |
| 29 | 1-chloro-2,2-difluoro-3-fluoro-1-methylcyclobutyl | H | H | $CH_3$ | $CH_3$ | O | O | 78 |
| 30 | n-$C_4H_9$— | H | H | $CH_3$ | $CH_3$ | S | O | 84 |
| 31 | $C_6H_5$—$CH_2$— | H | H | $CH_3$ | $CH_3$ | S | O | 120 |
| 32 | cyclohexyl | H | H | $CH_3$ | $CH_3$ | S | O | 105 |
| 33 | $FCH_2$—$C(CH_3)_2$— | H | H | H | $CH_3$ | O | O | 170 |
| 34 | $FCH_2$—$C(CH_3)_2$— | H | 3-Cl-$C_6H_4$-$CH_2$— | $CH_3$ | $CH_3$ | O | O | 158 |

TABLE 2-continued

Examples of the compounds of the formula (I)

| Ex. No. | R¹ | R² | R³ | R⁴ | R⁵ | X | Y | M.P. (°C.) |
|---|---|---|---|---|---|---|---|---|
| 35 |  | H | H | H | $CH_3$ | O | O | 123 |
| 36 | 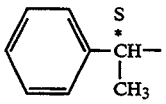 | H | H | $CH_3$ | $CH_3$ | O | O | $n_D^{20}$ = 1.5500 |
| 37 | 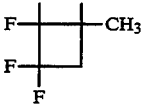 | H | $CH_3$ | $CH_3$ | $CH_3$ | O | O | 120 |
| 38 | 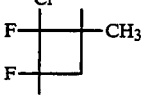 | H | H | H | $CH_3$ | O | O | 168 |
| 39 | 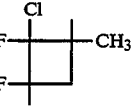 | H | H | $C_2H_5$ | $C_2H_5$ | O | O | 108 |
| 40 | $FCH_2C(CH_3)_2-$ | H | H | —($CH_2$)$_4$— | | O | O | 74 |
| 41 | $ClCH_2C(CH_3)_2-$ | H | H | —($CH_2$)$_4$— | | O | O | 165 |
| 42 | $ClCH_2C(CH_3)_2-$ | H | H | H | $CH(CH_3)_2$ | O | O | 135 |
| 43 | 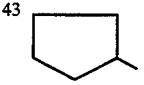 | H | H | —($CH_2$—)$_4$ | | O | O | 193 |
| 44 | $CH_3C(C_2H_5)_2-$ | H | H | —($CH_2$—)$_4$ | | O | O | 104 |
| 45 | $C_2H_5C(CH_3)_2-$ | H | H | —($CH_2$—)$_4$ | | O | O | 108 |
| 46 | 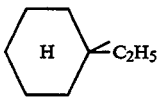 | H | H | —($CH_2$—)$_4$ | | O | O | 145 |
| 47 | $C_4H_9C(CH_3)_2$ | H | H | —($CH_2$—)$_4$ | | O | O | 87 |
| 48 | $(CH_3)_3-C-CH(CH_3)-$ | H | H | —($CH_2$—)$_4$ | | O | O | 143 |
| 49 | $C_2H_5-CH(CH_3)-$ | H | H | —($CH_2$—)$_4$ | | O | O | 123 |
| 50 | $FCH_2C(CH_3)_2-$ | H | $CH_3$ | H | $CH_3$ | O | O | 188 |
| 51 | $(CH_3)_2CH-CH(CH_3)-$ | H | $CH_3$ | H | $CH_3$ | O | O | 116 |
| 52 | $(CH_3)_3C-$ | H | H | $CH_3$ | $C_3H_7$ | O | O | 161 |
| 53 | $(CH_3)_2CH-$ | H | H | $CH_3$ | $C_3H_7$ | O | O | 154 |
| 54 | $(CH_3)_2CH-$ | H | H | $C_2H_5$ | $C_3H_7$ | O | O | ¹H-NMR/ D$_6$-DMSO, δ = 1.2 ppm/ d/6H |
| 55 | $(CH_3)_3C-$ | H | H | $CH_3$ | $C_2H_5$ | O | O | 149 |
| 56 | $ClCH_2C(CH_3)_2-$ | H | H | $CH_3$ | $C_2H_5$ | O | O | ¹H-NMR/ CDCl$_3$, δ = 3.24 ppm/q/ $CH_2$ |

TABLE 2-continued

Examples of the compounds of the formula (I)

| Ex. No. | R$^1$ | R$^2$ | R$^3$ | R$^4$ | R$^5$ | X | Y | M.P. (°C.) |
|---|---|---|---|---|---|---|---|---|
| 57 | (CH$_3$)$_2$CH— | H | H | CH$_3$ | C$_2$H$_5$ | O | O | $^1$H-NMR/ CCl$_3$, δ = 3.50 ppm/q/ CH$_2$ |
| 58 | C$_2$H$_5$CH(CH$_3$)— | H | H | —CH$_2$CH$_2$OCH$_2$CH$_2$— | | O | O | 145 |
| 59 | ClCH$_2$C(CH$_3$)$_2$— | H | H | —CH$_2$CH$_2$OCH$_2$CH$_2$— | | O | O | 195 |
| 60 | (CH$_3$)$_3$C— | H | H | H | H | O | O | 217 |
| 61 | ClCH$_2$C(CH$_3$)$_2$— | H | H | H | H | O | O | 200 |
| 62 | cyclohexyl-CH$_3$ (H) | H | H | —(CH$_2$)$_4$— | | O | O | 119 |
| 63 | C$_6$H$_5$O—CH$_2$CH(CH$_3$)— | H | H | —(CH$_2$)$_4$— | | O | O | $^1$HNMR/ CDCl$_3$, δ = 1.38 ppm/d/ CH$_3$ |
| 64 | (CH$_3$)$_2$CHC(CH$_3$)$_2$— | H | H | —(CH$_2$)$_4$— | | O | O | $^1$H-NMR/ CDCl$_3$, δ = 0.93 ppm/d/ 2CH$_3$ |
| 65 | (CH$_3$)$_3$C— | H | H | —(CH$_2$)$_4$— | | O | O | 112 |
| 66 | C$_4$H$_9$—n | H | H | —(CH$_2$)$_4$— | | O | O | 68 |
| 67 | ClCH$_2$CH(CH$_3$)— | H | CH$_3$ | H | CH$_3$ | O | O | 121 |
| 68 | C$_6$H$_5$—OCH$_2$CH(CH$_3$)— | H | CH$_3$ | H | CH$_3$ | O | O | 86 |
| 69 | cyclopentyl-CH$_3$ | H | CH$_3$ | H | CH$_3$ | O | O | 200 |
| 70 | HC≡C—C(CH$_3$)$_2$— | H | H | —(CH$_2$)$_4$— | | O | O | 151 |
| 71 | (CH$_3$)$_2$CHCH(CH$_3$)— | H | H | —(CH$_2$)$_4$— | | O | O | $^1$H-NMR/ D$_6$-DMSO, δ = 0.82 ppm/2d/ 2CH$_3$ |
| 72 | C$_2$H$_5$CH(CH$_3$)— | H | CH$_3$ | H | CH$_3$ | O | O | 121 |
| 73 | cyclopentyl- | H | CH$_3$ | H | CH$_3$ | O | O | 153 |
| 74 | C$_3$H$_7$C(CH$_3$)$_2$— | H | CH$_3$ | H | CH$_3$ | O | O | 130 |
| 75 | cyclopentyl-CH$_3$ | H | CH$_3$ | H | CH$_3$ | O | O | 159 |
| 76 | (C$_2$H$_5$)$_2$C(CH$_3$)— | H | CH$_3$ | H | CH$_3$ | O | O | 137 |
| 77 | (CH$_3$)$_2$CHC(CH$_3$)$_2$— | H | CH$_3$ | H | CH$_3$ | O | O | 169 |

TABLE 2-continued

Examples of the compounds of the formula (I)

| Ex. No. | R¹ | R² | R³ | R⁴ | R⁵ | X | Y | M.P. (°C.) |
|---|---|---|---|---|---|---|---|---|
| 78 | (CH₃)₃CCH(CH₃)— | H | CH₃ | H | CH₃ | O | O | 184 |
| 79 | C₂H₅C(CH₃)₂— | H | CH₃ | H | CH₃ | O | O | 166 |
| 80 | C₆H₅*CH(CH₃)— (S) | H | CH₃ | H | CH₃ | O | O | 114 |
| 81 | C₆H₅*CH(CH₃)— (R) | H | CH₃ | H | CH₃ | O | O | 121 |
| 82 | cyclohexyl-CH₃ | H | CH₃ | H | CH₃ | O | O | 154 |
| 83 | ClCH₂C(CH₃)₂— | H | H | H | C₃H₇ | O | O | 220 |
| 84 | C₂H₅CH(CH₃)— | H | H | H | CH(CH₃)₂ | O | O | 237 |
| 85 | C₂H₅C(CH₃)₂— | H | H | CH₃ | CH₃ | O | O | 82 |
| 86 | C₃H₇C(CH₃)₂— | H | H | CH₃ | CH₃ | O | O | 80 |
| 87 | cyclopentyl-CH₃ | H | H | CH₃ | CH₃ | O | O | 90 |
| 88 | cyclohexyl(H)-CH₃ | H | H | CH₃ | CH₃ | O | O | 117 |
| 89 | cyclohexyl-C₂H₅ | H | H | CH₃ | CH₃ | O | O | 140 |
| 90 | C₂H₅CH(CH₃)— | H | H | CH₃ | CH₃ | O | O | $n_D^{20}$ = 1.5105 |
| 91 | C₆H₅OCH₂CH(CH₃)— | H | H | CH₃ | CH₃ | O | O | ¹H-NMR/ CDCl₃, δ = 1.39 ppm/d/ CH₃ |
| 92 | C₆H₅CH₂C(CH₃)₂— | H | H | CH₃ | CH₃ | O | O | 146 |
| 93 | C₆H₅(CH₂)₂C(CH₃)₂— | H | H | CH₃ | CH₃ | O | O | 83 |

TABLE 2-continued

Examples of the compounds of the formula (I)

| Ex. No. | R¹ | R² | R³ | R⁴ | R⁵ | X | Y | M.P. (°C.) |
|---|---|---|---|---|---|---|---|---|
| 94 | cyclohexyl-CH(S)(CH₃)- | H | H | CH₃ | CH₃ | O | O | ¹H-NMR/CDCl₃, δ = 1.18 ppm/d/CH₃ |
| 95 | cyclohexyl-CH(R)(CH₃)- | H | H | CH₃ | CH₃ | O | O | ¹H-NMR/CDCl₃, δ = 1.18 ppm/d/3H |
| 96 | (CH₃)₂CH— | H | H | CH₃ | CH₃ | S | O | 121 |
| 97 | C₆H₁₃-n | H | H | CH₃ | CH₃ | S | O | 84 |
| 98 | furan-2-yl-CH₂— | H | H | CH₃ | CH₃ | S | O | 146 |
| 99 | cyclopropyl | H | H | CH₃ | CH₃ | S | O | 158 |
| 100 | (CH₃)₂CHCH₂— | H | H | CH₃ | CH₃ | S | O | 113 |
| 101 | C₆H₁₃-n | H | H | CH₃ | CH₃ | O | O | 56 |
| 102 | cyclohexyl | H | H | CH₃ | CH₃ | O | O | 134 |
| 103 | C₄H₉-n | H | H | CH₃ | CH₃ | O | O | 119 |
| 104 | C₆H₅CH₂— | H | H | CH₃ | CH₃ | O | O | 107 |
| 105 | ClCH₂C(CH₃)₂— | H | H | C₂H₅ | C₂H₅ | O | O | 112 |
| 106 | (CH₃)₃C— | H | H | C₂H₅ | C₂H₅ | O | O | ¹H-NMR/CDCl₃, δ = 1.16 ppm/t/2CH₃ |
| 107 | 1-methylcyclopentyl | H | H | C₂H₅ | C₂H₅ | O | O | 65 |
| 108 | (CH₃)₂CHCH₂— | H | H | CH₃ | CH₃ | O | O | 80 |
| 109 | ClCH₂C(CH₃)₂— | H | H | H | C₂H₅ | O | O | 131 |
| 110 | (CH₃)₂CH— | H | H | H | C₂H₅ | O | O | 117 |
| 111 | cyclohexyl-CH(S)(CH₃)- | H | H | H | C₂H₅ | O | O | 134 |
| 112 | C₆H₁₃CH(CH₃)— | H | H | CH₃ | CH₃ | O | O | (amorph) |
| 113 | (C₂H₅)₃C— | H | H | CH₃ | CH₃ | O | O | 134 |
| 114 | (CH₃)₃CCH₂CH(CH₃)— | H | H | CH₃ | CH₃ | O | O | 118 |
| 115 | (C₂H₅)₂CH— | H | H | CH₃ | CH₃ | O | O | 68 |

TABLE 2-continued

Examples of the compounds of the formula (I)

| Ex. No. | R¹ | R² | R³ | R⁴ | R⁵ | X | Y | M.P. (°C.) |
|---|---|---|---|---|---|---|---|---|
| 116 | (CH₃)₂CHC(CN)(CH₃)— | H | H | CH₃ | CH₃ | O | O | 108 |
| 117 | (C₂H₅)₂C(CH₃)— | H | H | CH₃ | CH₃ | O | O | 90 |
| 118 | (C₂H₅)CHCH₂— | H | H | CH₃ | CH₃ | O | O | n_D²⁰ = 1.5080 |
| 119 | NC—CH₂CH(C₂H₅)— | H | H | CH₃ | CH₃ | O | O | 92 |
| 120 | C₅H₁₁CH(CH₃)— | H | H | CH₃ | CH₃ | O | O | n_D²⁰ = 1.4963 |
| 121 | (CH₃)₃CCH₂C(CH₃)₂ | H | H | CH₃ | CH₃ | O | O | 177 |

The preparation of the Compound listed in Table 2 as Example No. 34 is described in detail below:

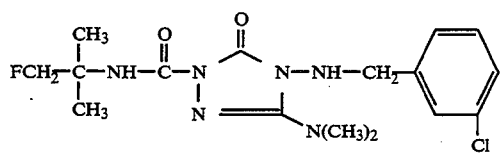

(Process (f))

2 g (32 mmol) of sodium cyanoborohydride are added at 0° C. to a mixture of 9.6 g (25 mmol) of 4-(3-chloro-benzylideneamino)-5-dimethylamino-2-(1,1-dimethyl-2-fluoro-ethylamino-carbonyl)-2,4-dihydro-3H-1,2,4-triazol-3-one and 50 ml of methanol, and the mixture is treated with saturated ethanolic hydrogen chloride solution until a methyl orange indicator changes colour. In the course of 6 hours, a further 2 g of sodium cyanoborohydride are added in portions, and the mixture is then stirred at 20° C. for 12 more hours. It is subsequently concentrated, the residue is taken up in methylene chloride, and the mixture is washed with water, dried over sodium sulphate and filtered. The filtrate is concentrated, the residue is crystallized using petroleum ether, and the product is isolated by filtration with suction.

This gives 7.9 g (82% of theory) of 4-(3-chlorobenzylamino)-5-dimethylamino-2-(1,1-dimethyl-2-fluoroethylamino-carbonyl)-2,4-dihydro-3H-1,2,4-triazol-3-one of melting point 158° C.

Starting substances of the formulae (II)/(IIa): Examples (II-1)

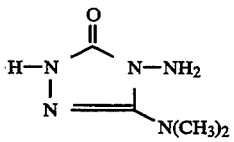

130 g (1.44 mol) of carbodihydrazide are suspended in a mixture of 470 g of phenol and 200 ml of chlorobenzene, and the suspension is treated with 153 g (1.44 mol) of sodium carbonate and 3.0 g (12 mmol) of dibutyltin oxide and warmed to 50° C. to 60° C. in a water pump vacuum. A solution of 247 g (1.44 mol) of tetramethyl-chloroformamidiniumchloride in 400 g of phenol is added dropwise in the course of 20 minutes, during which process water distils off. Chlorobenzene is then distilled off in a water pump vacuum until the boiling point of phenol is reached. The reaction mixture is subsequently heated to 160° C. to 180° C. under atmospheric pressure, during which process dimethylamine is eliminated. After 3 hours, phenol is distilled off at 190° C. for one hour. The solid residue which remains is extracted in a Soxleth extractor using 1.5 liters of isopropanol; the isopropanol solution is evaporated.

This gives 47 g (23% of theory) of 4-amino-5-dimethylamino-2,4-dihydro-3H-1,2,4-triazol-3-one as a crystalline residue of melting point 205° C.

EXAMPLE (II-2)

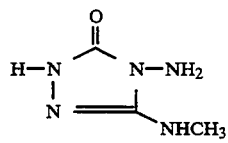

A mixture of 360 g (2.0 mol) of carbodihydrazide, 212 g (2.0 mol) of sodium carbonate and 580 g of phenol is heated to 50° C. to 60° C. A solution of 314 g (2.0 mol) of trimethyl-chloroformamidine hydrochloride in 314 g of phenol is then added dropwise in a water pump vacuum in the course of 30 minutes. The reaction mixture is then stirred for 60 minutes at 50° C. to 60° C. and subsequently heated to 190 ° C., during which process dimethylamine is eliminated. When the evolution of gas has ceased, the phenol is distilled off in a water pump vacuum and the residue is recrystallized from water.

This gives 60 g (26% of theory) of 4-amino-5-methylamino-2,4-dihydro-3H-1,2,4-triazol-3-one of melting point 220° C.

EXAMPLE (II-3)

Step 1

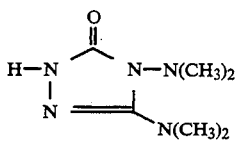

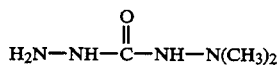

856 g (4.0 mol) of diphenyl carbonate are initially introduced into the reaction vessel with water cooling, and 245 g (4.0 mol) of N,N-dimethylhydrazine are added dropwise. The mixture is then slowly heated to 60° C. (in the course of 4 hours). The mixture is cooled to 20° C., and 200 g (4.0 mol) of hydrazine hydrate are subsequently added, and the reaction mixture is stirred for 12 hours at 20° C. After the mixture has been heated to 70° C. to 80° C. for one hour, volatile components are distilled off under a water pump vacuum until a bottom temperature of 100° C. is reached. The residue which remains essentially contains a solution of 1,1-dimethyl-carbodihydrazide in phenol, and this solution is employed directly in the next step.

Step 2

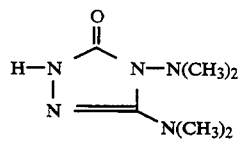 (II-3)

251 g of the above solution of 1,1-dimethylcarbodihydrazide in phenol (about 0.82 mol) are diluted with 100 g of phenol, 87 g (0.82 mol) of sodium carbonate are added, and the mixture is heated to 50° C. to 60° C. A solution of 140 g (0.82 mol) of tetramethyl-chloroformamidinium chloride in 250 g of phenol is then added dropwise in the course of 75 minutes in an oil-pump vacuum. The reaction mixture is then refluxed for 6 hours under atmospheric pressure (about 190° C. to 195° C.), during which process dimethylamine is eliminated. The mixture is then distilled under an oil-pump vacuum, and the distillate is redistilled. The distillate which has now been obtained (40 g) is taken up in xylene and the mixture is cooled to −78° C. The product which is obtained in crystalline form in this process is isolated by filtration with suction.

This gives 22.8 g (16% of theory) of 4,5-bis-dimethylamino-2,4-dihydro-3H-1,2,4-triazol-3-one of melting point 93° C.

Example (II-4)

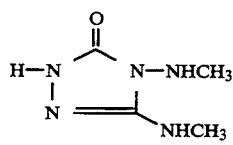

Step 1

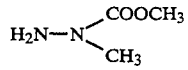 (XVIII-1)

A solution of 94 g (2.0 mol) of methylhydrazine in 100 ml of methanol is cooled to 0° C. to −20° C., and 268 g (2.0 mol) of dimethyl pyrocarbonate are continuously added dropwise in such a way that the temperature does not exceed 0° C. The reaction mixture is then stirred at 80° C. until the evolution of gas has virtually ceased, and subsequently distilled under a water pump vacuum.

This gives 181 g (87% of theory) of N-methyl-n-methoxycarbonylhydrazine of boiling point 65° C./15 torr.

Step 2

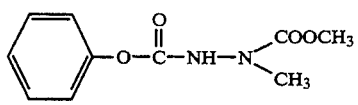 (XIX-1)

624 g (6.0 mol) of 1-methyl-1-methoxycarbonylhydrazine and 334 g (3.15 mol) of sodium carbonate are initially introduced into 2 liters of ethylene chloride, and 939 g (6.0 mol) of phenyl chloroformate are added dropwise with stirring in such a way that the temperature does not exceed 20° C. The mixture is then stirred for another 60 minutes at 60° C., and the sodium chloride which has been liberated is separated off by filtration with suction. The solvent is removed from the filtrate by distillation under a water pump vacuum at a bottom temperature of not more than 110° C.

This gives 1285 g (96% of theory) of 1-methyl-1-methoxycarbonyl-2-phenoxycarbonyl-hydrazine as an oily residue which gradually crystallizes.

Melting point: 86° C.

Step 3:

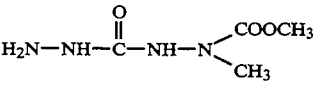 (XIIIb-1)

206 g (4.12 mol) of hydrazine hydrate are initially introduced into a reaction vessel at 20° C., and a solution of 922 g (4.12 mol) of 1-methyl-1-methoxycarbonyl-2-phenoxycarbonyl-hydrazine in 600 g of chlorobenzene, warmed to 40° C., is added all at once, which causes the temperature of the reaction mixture to rise to about 60° C. The mixture is then stirred for 4 hours at 80° C. and subsequently concentrated under water pump vacuum until a bottom temperature of about 100° C. is reached. The residue, which essentially contains 1-methyl-1-methoxy-carbonyl-carbodihydrazide, is employed directly in the next step.

Step 4

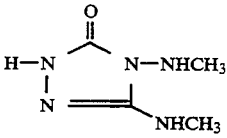 (II-4)

A mixture of 160 g (0.626 mol) of 1-methyl-1-methoxycarbonyl-carbodihydrazide and 160 g of phenol is warmed to 40° C., and 142 g (0.626 mol) of diphenyl methyliminocarbonate are added. When the exothermic reaction has subsided, the mixture is slowly heated to 150° C. under a water pump vacuum, during which process about 150 g of phenol distil off. After cooling, the residue is stirred with 100 ml of water and 120 g of 50% strength sodium hydroxide solution, and the mixture is refluxed for 60 minutes. 300 ml of 18% strength hydrochloric acid are then added and the batch is evaporated. The residue is distilled under an oil-pump vacuum and the crude distillate is redistilled.

This gives 45 g (50% of theory) of 4,5-bis-methylamino-2,4-dihydro-3H-1,2,4-triazol-3-one as an oily product which solidifies in the receiving vessel to a wax-like substance. Stirring with ethyl acetate gives 40 g (44%) of a white, crystalline product of melting point 135–137° C.

EXAMPLE (II-5)

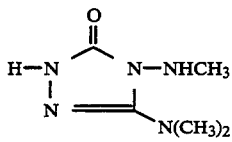

A phenolic solution of 1-methyl-1-methoxycarbonyl-carbodihydrazide is prepared as described in Example (II-4), step 3. 384 g of this solution (1.5 mol) are taken up in 200 ml of chlorobenzene, 239 g (2.25 mol) of sodium carbonate are added, and the mixture is warmed to 50° C. under a water pump vacuum. During this process, a solution of 244 g (1.5 mol) of dichloromethylenedimethylimmonium chloride in 566 g of phenol is added dropwise, during which process water is removed by azeotropic distillation. Stirring of the reaction mixture is then continued for 60 minutes at 120° C. under atmospheric pressure, and the mixture is then hot-filtered and washed with ethanol and acetone. The organic solution is concentrated, the residue is refluxed with 240 ml of 50% strength sodium hydroxide solution, allowed to cool, and rendered neutral using concentrated hydrochloric acid. After the mixture has been concentrated under a water pump vacuum, the residue is distilled under an oil-pump vacuum, and the crude distillate is redistilled.

This gives 72 g of oily product (boiling point 165° C./1 mbar) which is converted into a pure crystalline product using 300 ml of toluene.

Yield: 60.0 g (25.5% of theory) of 4-methylamino5-dimethylamino-2,4-dihydro-3H-1,2,4-triazol-3-one; Melting point: 129° C.

EXAMPLE (II-6)

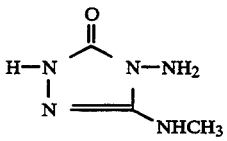

A mixture of 58 g ( 0.25 mol) of 1,3-diamino-2-methylguanidine hydroiodide, 53.5 g ( 0.25 mol ) of diphenyl carbonate and 20 g of phenol is heated to 160° C. while stirring, until the mixture is virtually homogeneous. 34.5 g (0.25 mol) of potassium carbonate are then added in portions, during which process carbon dioxide is liberated. After 60 minutes at 160° C., the mixture is slightly cooled, and the phenol is distilled off under a water pump vacuum. The residue is taken up in 200 ml of water, the mixture is rendered neutral using hydrochloric acid, and ethanol is added slowly, during which process the reaction mixture is obtained in crystalline form.

This gives 24 g (74% of theory) of 4-amino-5-methylamino-2,4-dihydro-3H-1,2,4-triazol-3-one of melting point 214° C.

The compounds of the formula (II)

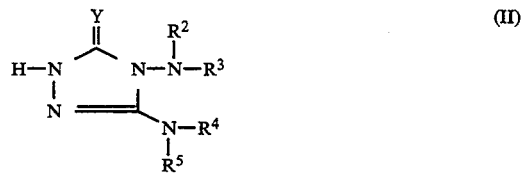

which are listed in Table 3 below can also be prepared analogously to Examples (II-1) to (II-6) and following the general description of the preparation processes according to the invention:

TABLE 3

Examples of the compounds of the formula (II)

| Ex.-No. | $R^2$ | $R^3$ | $R^4$ | $R^5$ | Y | M.P. (°C.) |
|---|---|---|---|---|---|---|
| II-7 | H | H | $C_2H_5$ | $C_2H_5$ | O | 195–196 |
| II-8 | H | H | H | $C_2H_5$ | O | 219–220 |
| II-9 | H | H | | $-(CH_2)_4-$ | O | 233 |
| II-10 | H | $CH_3$ | H | $(CH_3)_2CH$ | O | 120 |
| II-11 | H | H | H | $(CH_3)_2CH$ | O | 150–152 |
| II-12 | H | H | H | $C_3H_7$ | O | |
| II-13 | H | H | $CH_3$ | $C_2H_5$ | O | 186 |
| II-14 | H | H | $CH_3$ | $C_3H_7$ | O | 165 |
| II-15 | H | H | $CH_3$ | $(CH_3)_2CH$ | O | |
| II-16 | H | H | $C_2H_5$ | $C_3H_7$ | O | 186 |
| II-17 | H | H | $C_2H_5$ | $(CH_3)_2CH$ | O | |
| II-18 | H | H | $C_3H_7$ | $C_3H_7$ | O | |
| II-19 | H | H | $C_3H_7$ | $(CH_3)_2CH$ | O | |
| II-20 | H | $CH_3$ | $CH_3$ | $C_2H_5$ | O | |
| II-21 | H | $CH_3$ | $CH_3$ | $C_3H_7$ | O | |
| II-22 | H | $CH_3$ | $CH_3$ | $(CH_3)_2CH$ | O | |
| II-23 | H | $CH_3$ | $C_2H_5$ | $C_2H_5$ | O | |
| II-24 | H | $CH_3$ | $C_2H_5$ | $C_3H_7$ | O | |
| II-25 | H | $CH_3$ | $C_3H_7$ | $C_3H_7$ | O | |
| II-26 | H | $C_2H_5$ | $CH_3$ | $CH_3$ | O | |
| II-27 | H | $C_2H_5$ | $CH_3$ | $C_2H_5$ | O | |
| II-28 | H | $C_2H_5$ | $C_2H_5$ | $C_2H_5$ | O | |
| II-29 | H | H | | $-(CH_2)_2-$ | O | |
| II-30 | H | $CH_3$ | | $-(CH_2)_2-$ | O | |
| II-31 | H | $C_2H_5$ | | $-(CH_2)_2-$ | O | |
| II-32 | $CH_3$ | $CH_3$ | H | $CH_3$ | O | 167 |
| II-33 | $CH_3$ | $CH_3$ | $CH_3$ | $C_2H_5$ | O | |
| II-34 | H | H | H | △ | O | |
| II-35 | H | $CH_3$ | H | △ | O | |
| II-36 | $CH_3$ | $CH_3$ | H | △ | O | |
| II-37 | H | H | $CH_3$ | △ | O | |
| II-38 | H | $CH_3$ | $CH_3$ | △ | O | |
| II-39 | H | H | $-CH_2CH_2-O-CH_2CH_2-$ | | O | 267 |

The compound listed in Table 3 as Example (II-11) can be prepared for example as follows:

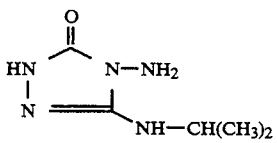

A mixture of 448 g (2 mol) of 1-ethoxycarbonyl-2-phenoxycarbonyl-hydrazine (cf. EP-A 65366), 350 g of phenol and 100 ml of 1,2-dichloroethane is initially introduced at 20° C. and 100 g (2 mol) of hydrazine hydrate are added in one portion while cooling with water. The mixture is stirred for 15 hours at 40° C. and is then heated to 100° C. over a period of 6 hours. Then water is distilled off under a water-jet vacuum (bottom temperature at most 100° C.) and the mixture is then again cooled to 20° C. Then a solution of 510 g (2 mol) of diphenyl N-isopropyl-iminodiphenylcarbonate in 500 ml of dichloromethane is added in one portion. The mixture is stirred for one hour at 20° C., for a further hour at 50° and finally for 30 minutes at 95° C.; it is then heated to 180° C. over a period of about one hour, 1,2-dichloroethane being distilled off. Then phenol (altogether 834 g) is distilled off—first under a water-jet vacuum and then under an oil pump vacuum. 150 ml of water and 640 g (4 mol NaOH) of 25% strength sodium hydroxide solution are added to the residue and the mixture is heated under reflux for 60 minutes; it is then neutralized with 811 g (4 mol HCl) of 18% strength hydrochloric acid at room temperature and concentrated by evaporation. The residue, which is now virtually free of water, is hot-extracted with 600 ml of dimethyl formamide and freed from sodium chloride by suction filtration. The filtrate is concentrated and the residue is taken up in 250 ml of water, extracted with approximately the same volume of ethyl acetate, and the organic phase is separated off, dried over magnesium sulphate and filtered. The solvent is distilled off carefully from the filtrate under a water-jet vacuum. 34 g (11% of theory) of 4-amino-5-isopropylamino-2,4-dihydro-3H-1,2,4-triazol-3-one of melting point 150° C.-152° C. are obtained.

The compound described under Example (II-4) can for example also be prepared as follows:

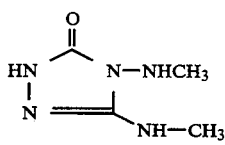

256 g of a phenolic solution of (1 mol) 1-methyl-1-methoxycarbonyl-carbodihydrazide—prepared as under Example (II-4), step 3—are initially introduced at 40° C. with an additional 150 g of phenol and 135 g (1 mol) of S,S-dimethyl-N-methyl-iminodithiocarbonate are added. Then the mixture is heated to 60° C. under a water-jet vacuum, the reaction taking place with the elimination of methyl mercaptan. The mixture is then heated to 80° C. in the course of one hour. Then phenol is distilled off by heating to a temperature of a maximum of 160° C.—in the end under an oil pump vacuum. After adding 50 ml of water and 160 g (2 mol NaOH) of 50% strength sodium hydroxide solution the mixture is heated under reflux for one hour.

406 g (2 mol HCl) of 18% strength hydrochloric acid are added to the cooled mixture and the water is then distilled off in a rotary evaporator. The product obtained by distillation of the residue under an oil pump vacuum is stirred with ethyl acetate and filtered off with suction.

60 g (42% of theory) of 4,5-bis-methylamino-2,4-dihydro-3H-1,2,4-triazol-3-one of melting point 135° C.-137° C. are obtained.

The compound described under Example (II-1) can for example also be obtained by the following process variants:

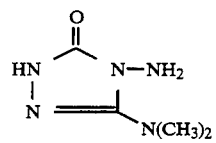

700 g (4.3 mol) of dichloromethylene-dimethylimmonium chloride are initially introduced in 3 liters of methylene chloride at about 40° C. and 808 g (8.6 mol) of phenol are added dropwise over a period of 90 minutes. Then a further 540 g of phenol are added and the methylene chloride is distilled off under a water-jet vacuum. A phenolic solution of diphenoxymethylene dimethylimmonium chloride remains which is used directly in the next stage.

A solution of 387 g (4.3 mol) of carbodihydrazide in 1300 g of phenol is initially introduced together with 274 g (2.58 mol) of sodium carbonate and the solution of diphenoxymethylene-dimethyl-immonium chloride (1193 g) in 540 g of phenol obtained as described above is added dropwise in such a manner that an internal temperature of 40° C. is not exceeded. The reaction is carried out in the course of 90 minutes, water being distilled off under an oil pump vacuum. Then the mixture is slowly heated further to 130° C. under an oil pump vacuum, the phenol being finally substantially distilled off. The residue is treated with 2.4 liters of (hot) ethoxyethanol, the undissolved sodium chloride is separated off by suction filtration under heat and the filtrate is cooled. The product obtained in crystalline form in this manner is isolated by suction filtration.

87 g (14% of theory) of 4-amino-5-dimethylamino-2,4-dihydro-3H-1,2,4-triazol-3-one of melting point 205° C are obtained.

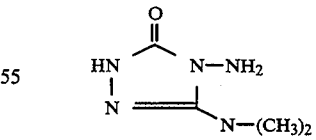

A mixture of 104 g (1 mol) of ethyl hydrazinoformate, 200 g of phenol, 50 ml of dimethyl formamide and 106 g (1 mol) of sodium carbonate is initially introduced under a water-jet vacuum and a solution of 171 g (1 mol) of tetramethylchloroformamidinium chloride in 200 g of phenol is added in such a manner that a temperature of 40° C. is not exceeded, water being gradually distilled off. Then the mixture is heated slowly, 55 g (1.1 mol) of hydrazine hydrate are added at 80° C. and the mixture is heated under atmospheric pressure in the course of 3 hours until phenol is refluxed (at about 190° C.), dimethylamine being eliminated. The phenol is then distilled off under a water-jet vacuum, the residue is treated with 750 ml of (hot) ethoxyethanol, the salt is separated off by filtration under heat and the filtrate is cooled. The crystalline product obtained in this manner is isolated by suction filtration.

49 g (34% of theory) of 4-amino-5-dimethylamino-2,4-dihydro-3H-1,2,4-triazol-3-one of melting point 205° C. are obtained.

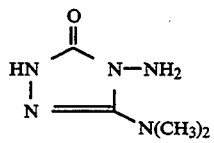

88 g (1 mol) of ethylene glycol carbonate are initially introduced into 300 ml of ethylene glycol and 50 g (1 mol) of hydrazine hydrate are added dropwise. After the exothermic reaction has subsided water is distilled off under a water-jet vacuum. Then 106 g (1 mol) of sodium carbonate are added and a solution of 171 g (1 mol) of tetramethylchloroformamidinium chloride in 300 ml of ethylene glycol is added dropwise at 20° C. to 30° C. in the course of one hour under an oil pump vacuum, during which water distils off. Then the mixture is heated to 80° C. over a period of 90 minutes and, after 55 g (1.1 mol) of hydrazine hydrate have been added, is heated to 180° C. in the course of 3 hours, dimethylamine being eliminated. Then the ethylene glycol is distilled off under a water-jet vacuum, the residue is treated with hot dimethyl formamide (300 ml), the salt is filtered off and the filtrate is concentrated by evaporation. The residue is recrystallized from 240 ml of water/isopropanol (vol: 1:2).

25 g (18% of theory) of 4-amino-5-dimethylamino-2,4-dihydro-3H-1,2,4-triazol-3-one of melting point 205° C. are obtained.

The compound described under Example (II-5) can, for example, also be obtained as follows:

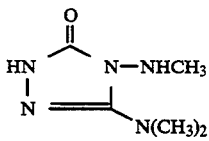

As described under Example (II-4)—step 3—a phenolic solution of 1-methyl-1-methoxycarbonyl-carbodihydrazide is prepared. 128 g (0.5 mol) of this solution are mixed with 75 g of phenol, 150 g of chlorobenzene and 52 g (0.5 mol) of sodium carbonate and 85.8 g (0.5 mol) of tetramethylchloroformamidinium chloride (dissolved in 150 g of phenol) are added dropwise at 50° C. to 60° C. under a water-jet vacuum in the course of one hour, during which water distils off.

The mixture is first heated to 80° C., still under a water-jet vacuum, and is then stirred for a further hour at 120° C. under atmospheric pressure. Then the mixture is heated to 185° C. in the course of 2 hours, dimethylamine being eliminated. Then the phenol is distilled off, first under a water-jet vacuum and then under an oil pump vacuum and the residue is heated for one hour under reflux with 200 ml of water and 96 g (1.2 mol NaOH) of 50% strength sodium hydroxide solution. After 243 g (1.2 mol HCl) of 18% strength hydrochloric acid have been added the mixture is concentrated by evaporation, the residue is treated with 400 mol of hot chlorobenzene, and the salt is separated off by filtration and the filtrate is worked up by distillation. The high-boiling fraction (165° C./1 mbar) is crystallized with 100 ml of toluene. 21 g (27% of theory) of 4-methylamino-5-dimethylamino-2,4-dihydro-3H-1,2,4-triazol-3-one of melting point 129° C. are obtained.

STARTING SUBSTANCES OF THE FORMULA (IV)

EXAMPLE (IV-1)

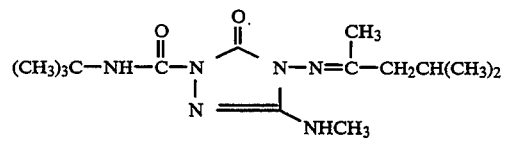

3.2 g (15 mmol) of 4-(4-methyl-2-pentylideneamino)-5-methylamino-2,4-dihydro-3H-1,2,4-triazol-3-one are dissolved in 80 ml of acetonitrile, and 100 mg of diazabicycloundecene (DBU) and 1.5 g (15 mmol) of tert-butyl isocyanate are added in succession. The reaction mixture is stirred for 2 days at 20° C. and subsequently concentrated. The residue is taken up in methylene chloride, washed with water, dried over sodium sulphate and filtered. The solvent is carefully removed from the filtrate by distillation under a water pump vacuum.

This gives 4.0 g (86% of theory) of 2-tert-butylaminocarbonyl-4-(4-methyl-2-pentylideneamino)-5-methylamino-2,4-dihydro-3H-1,2,4-triazol-3-one as an oily residue.

$^1$H-NMR (CDCl$_3$, δ, ppm): 1.00 (d, CH$_3$), 1.43 (s, CH$_3$), 2.35 ( d, CH$_2$), 2.96 ( d, NHCH$_3$ ), 4.35 ( q, NHCH$_3$), 7.65 (s, NH).

The compounds of the formula (IV)

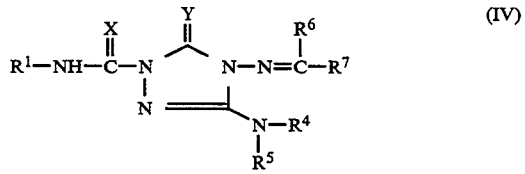

which are listed in Table 4 below can also be prepared analogously to Example (IV-1) and following the general description of the preparation processes according to the invention.

TABLE 4

| | Examples of the compounds of the formula (IV) | | | | | | | |
|---|---|---|---|---|---|---|---|---|
| Ex.-No. | $R^1$ | $R^4$ | $R^5$ | $R^6$ | $R^7$ | X | Y | M.P. (°C.) or refractive index |
| IV-2 | FCH$_2$—C(CH$_3$)$_2$— | H | CH$_3$ | CH$_3$ | CH$_2$CH(CH$_3$)$_2$ | O | O | 88 |

TABLE 4-continued

Examples of the compounds of the formula (IV)

| Ex.-No. | R¹ | R⁴ | R⁵ | R⁶ | R⁷ | X | Y | M.P. (°C.) or refractive index |
|---|---|---|---|---|---|---|---|---|
| IV-3 | FCH₂—C(CH₃)₂— | CH₃ | CH₃ | H | 3-Cl-C₆H₄— | O | O | 150 |
| IV-4 | 3-chloro-2,2-difluoro-1-methylcyclobutyl | H | CH₃ | CH₃ | CH₂CH(CH₃)₂ | O | O | $n_D^{20}$ = 1.4873 |
| IV-5 | ClCH₂C(CH₃)₂— | —(CH₂—)₄ | CH₃ | | CH₂CH(CH₃)₂ | O | O | $n_D^{20}$ = 1.5183 |
| IV-6 | ClCH₂C(CH₃)₂— | H | CH(CH₃)₂ | CH₃ | CH₂CH(CH₃)₂ | O | O | 48 |
| IV-7 | FCH₂C(CH₃)₂— | —(CH₂—)₄ | | CH₃ | CH₂CH(CH₃)₂ | O | O | 115 |
| IV-8 | C₄H₉C(CH₃)₂— | —(CH₂—)₄ | | CH₃ | CH₂CH(CH₃)₂ | O | O | $n_D^{20}$ = 1.4985 |
| IV-9 | (CH₃)₃C—CH(CH₃)— | —(CH₂—)₄ | | CH₃ | CH₂CH(CH₃)₂ | O | O | 121 |
| IV-10 | (CH₃)₂CH—C(CH₃)₂— | —(CH₂—)₄ | | CH₃ | CH₂CH(CH₃)₂ | O | O | 73 |
| IV-11 | (C₂H₅)₂C(CH₃)— | —(CH₂—)₄ | | CH₃ | CH₂CH(CH₃)₂ | O | O | $n_D^{20}$ = 1.5115 |
| IV-12 | 1-ethylcyclohexyl | —(CH₂—)₄ | | CH₃ | CH₂CH(CH₃)₂ | O | O | $n_D^{20}$ = 1.5163 |
| IV-13 | cyclopentyl | —(CH₂—)₄ | | CH₃ | CH₂CH(CH₃)₂ | O | O | 112 |
| IV-14 | C₆H₅—O—CH(CH₃)— | —(CH₂—)₄ | | CH₃ | CH₂CH(CH₃)₂ | O | O | 88 |
| IV-15 | 1-methylcyclohexyl | —(CH₂—)₄ | | CH₃ | CH₂CH(CH₃)₂ | O | O | $n_D^{20}$ = 1.5100 |
| IV-16 | C₂H₅—C(CH₃)₂— | —(CH₂—)₄ | | CH₃ | CH₂CH(CH₃)₂ | O | O | $n_D^{20}$ = 1.5016 |
| IV-17 | C₂H₅—CH(CH₃)— | —(CH₂—)₄ | | CH₃ | CH₂CH(CH₃)₂ | O | O | $n_D^{20}$ = 1.5095 |
| IV-18 | (CH₃)₃C— | —(CH₂)₄— | | CH₃ | CH₂CH(CH₃)₂ | O | O | 117 |
| IV-19 | nC₄H₉ | —(CH₂—)₄ | | CH₃ | CH₂CH(CH₃)₂ | O | O | $n_D^{20}$ = 1.5130 |
| IV-20 | HC≡C—C(CH₃)₂— | —(CH₂)₄— | | CH₃ | CH₂CH(CH₃)₂ | O | O | 101 |
| IV-21 | (CH₃)₂CHCH(CH₃)— | —(CH₂)₄— | | CH₃ | CH₂CH(CH₃)₂ | O | O | 76 |
| IV-22 | (CH₃)₃C— | —CH₂CH₂OCH₂CH₂— | | CH₃ | CH₂CH(CH₃)₂ | O | O | 110 |
| IV-23 | ClCH₂C(CH₃)₂— | CH₃ | CH₃ | CH₃ | CH₂CH(CH₃)₂ | O | O | $n_D^{20}$ = 1.5095 |

STARTING SUBSTANCES OF THE FORMULA (VIII)

EXAMPLE (VIII-1)

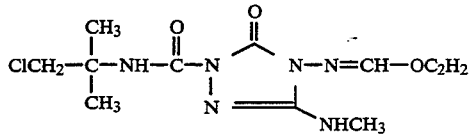

3.7 g (0.02 mol) of 4-ethoxymethyleneamino-5-methylamino-2,4-dihydro-3H-1,2,4-triazol-3-one are dissolved in 100 ml of acetonitrile, and 100 mg of diazabicycloundecene (DBU) and 2.8 g (0.02 mol) of chloro-tert-butyl isocyanate are added in succession. The mixture is stirred for 12 hours at 20° C. and then concentrated. The residue is taken up in methylene chloride, and the mixture is washed with water, dried over sodium sulphate and filtered. The solvent is removed from the filtrate by distillation under a water pump vacuum, and the residue is crystallized by trituration with diethyl ether.

This gives 5.2 g (82% of theory) of 2-chloro-tert-butylaminocarbonyl-4-ethoxymethyleneamino-5-methyl-amino-2,4-dihydro-3H-1,2,4-triazol-3-one of melting point 142° C.

The compounds of the formula (VIII) which are listed in Table 5 below can also be prepared analogously to Example VIII-1 and following the general description of the preparation processes according to the invention.

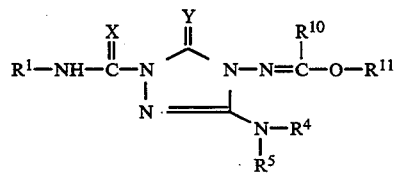

TABLE 5
Examples of the compounds of the formula (VIII)

| Ex.-No. | $R^1$ | $R^4$ | $R^5$ | $R^{10}$ | $R^{11}$ | X | Y |
|---|---|---|---|---|---|---|---|
| VIII-2 | $(CH_3)_3C-$ | $CH_3$ | $CH_3$ | H | $C_2H_5$ | O | O |
| VIII-3 | $(CH_3)_3C-$ | $C_2H_5$ | $C_2H_5$ | H | $C_2H_5$ | O | O |
| VIII-4 | $Cl-CH_2-C(CH_3)_2-$ | $CH_3$ | $CH_3$ | H | $C_2H_5$ | O | O |
| VIII-5 | cyclopentyl | $-(CH_2)_4-$ | | H | $C_2H_5$ | O | O |
| VIII-6 | $ClCH_2C(CH_3)_2-$ | H | $CH(CH_3)_2$ | H | $C_2H_5$ | O | O |

INTERMEDIATES OF THE FORMULA (XXI)

EXAMPLE (XXI-1)

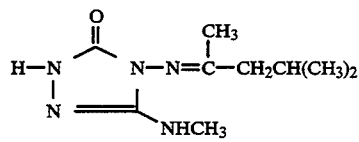

12.9 g (0.1 mol) of 4-amino-5-methylamino-2,4-dihydro-3H-1,2,4-triazol-3-one are refluxed on a water separator with 150 ml of methyl isobutyl ketone and mg of p-toluenesulphonic acid until virtually no water is separated any longer (about 2 hours). The mixture is filtered, the filtrate is concentrated, and the residue is triturated with petroleum ether.

This gives 8.3 g (39% of theory) of 4-(4-methyl-2-pentylidene-amino)-5-methylamino-2,4-dihydro-3H-1,2,4-triazol-3-one of melting point 136° C.

The compounds of the formula (XXI) which are listed in Table 6 below can also be prepared analogously to Example (XXI-1) and following the general description of the preparation processes according to the invention:

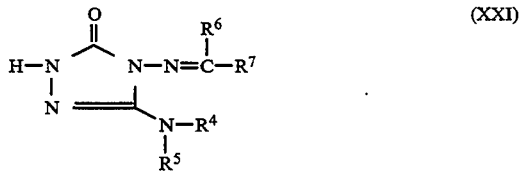

TABLE 6
Examples of the compounds of the formula (XXI)

| Ex.-No. | $R^4$ | $R^5$ | $R^6$ | $R^7$ | Y | M.P. (°C.) |
|---|---|---|---|---|---|---|
| XXI-2 | $CH_3$ | $CH_3$ | $CH_3$ | $CH_3$ | O | 197 |
| XXI-3 | $CH_3$ | $CH_3$ | $CH_3$ | $(CH_3)_2CH-CH_2-$ | O | 105 |
| XXI-4 | $-(CH_2)_4-$ | | $CH_3$ | $(CH_3)_2CH-CH_2-$ | O | 133 |
| XXI-5 | H | $C_2H_5$ | $CH_3$ | $(CH_3)_2CH-CH_2-$ | O | 105 |
| XXI-6 | H | $(CH_3)_2CH$ | $CH_3$ | $(CH_3)_2CH-CH_2-$ | O | 94 |
| XXI-7 | H | $C_3H_7$ | $CH_3$ | $(CH_3)_2CH-CH_2-$ | O | |
| XXI-8 | $CH_3$ | $C_2H_5$ | $CH_3$ | $(CH_3)_2CH-CH_2-$ | O | |
| XXI-9 | $C_2H_5$ | $C_2H_5$ | $CH_3$ | $(CH_3)_2CH-CH_2-$ | O | 80 |
| XXI-10 | $CH_3$ | $C_3H_7$ | $CH_3$ | $(CH_3)_2CH-CH_2-$ | O | |

INTERMEDIATES OF THE FORMULA (XXV)

EXAMPLE (XXV-1)

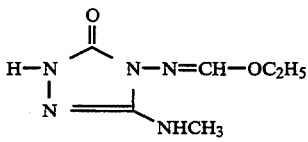

12.9 g (0.1 mol) of 4-amino-5-methylamino-2,4-dihydro-3H-1,2,4-triazol-3-one are refluxed for 4 hours with 100 ml of triethyl orthoformate and 100 mg of p-toluenesulphonic acid. The mixture is then concentrated and crystallized with diethyl ether. Recrystallization from ethanol gives 10.0 g (54% of theory) of 4-ethoxymethyleneamino-5-methylamino-2,4-dihydro-3H-1,2,4-triazol-3-one of melting point 169° C.

The compounds of the formula (XXV) which are listed in Table 7 below can also be prepared analogously to Example (XXV-1) and following the general description of the preparation processes according to the invention:

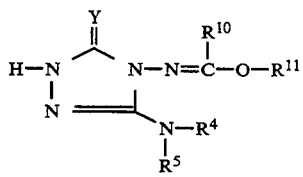

(XXV)

TABLE 7

Examples of the compounds of the formula (XXV)

| Ex.-No. | $R^4$ | $R^5$ | $R^{10}$ | $R^{11}$ | Y | M.P. (°C.) |
|---|---|---|---|---|---|---|
| XXV-2 | $CH_3$ | $CH_3$ | H | $C_2H_5$ | O | 72 |
| XXV-3 | $CH_3$ | $C_2H_5$ | H | $C_2H_5$ | O | |
| XXV-4 | $CH_3$ | $C_3H_7$ | H | $C_2H_5$ | O | |
| XXV-5 | H | $CH_3$ | $CH_3$ | $C_2H_5$ | O | |
| XXV-6 | —$(CH_2)_4$— | | H | $C_2H_5$ | O | |
| XXV-7 | $C_2H_5$ | $C_2H_5$ | H | $C_2H_5$ | O | |
| XXV-8 | H | $CH(CH_3)_2$ | H | $C_2H_5$ | O | |

USE EXAMPLES

In the Use Examples which follow, the compound listed below was employed as comparison substance:

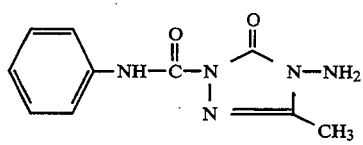

(A)

4-amino-5-methyl-2-phenylaminocarbonyl-2,4-dihydro-3H-1,2,4-triazol-3-one (disclosed in EP-A 294,666, Example 122).

EXAMPLE A

Pre-emergence test
Solvent: 5 parts by weight of acetone
Emulsifier: 1 part by weight of alkylaryl polyglycol ether To prepare a suitable preparation of active compound, 1 part by weight of active compound is mixed with the stated amount of solvent, the stated amount of emulsifier is added, and the concentrate is diluted with water to the desired concentration.

Seeds of the test plants are sown in normal soil and, after 24 hours, watered with the preparation of active compound. It is expedient here to keep constant the amount of water per unit area. The concentration of active compound in the preparation is of no importance, only the application rate of the active compound per unit area being decisive. After three weeks, the degree of damage to the plants is rated in % damage in comparison with the development of the untreated control. The figures denote:
0% = no action (like untreated control)
100% = total destruction In this test, a clearly superior activity compared with the comparison substance (A) is shown, for example, by the compounds Preparation Examples 16, 17, 18 and 19.

EXAMPLE B

Post-emergence test
Solvent: 5 parts by weight of acetone
Emulsifier: 1 part by weight of alkylaryl polyglycol ether To prepare a suitable preparation of active compound, 1 part by weight of active compound is mixed with the stated amount of solvent, the stated amount of emulsifier is added, and the concentrate is diluted with water to the desired concentration.

Test plants which have a height of 5–15 cm are sprayed with the preparation of active compound in such a way that the specifically desired amounts of active compound are applied per unit area. The concentration of the spray liquor is so chosen that the specifically desired amounts of active compound are applied in 2000 l of water/ha. After three weeks, the degree of damage to the plants is rated in % damage in comparison with the development of the untreated control. The figures denote:
0% = no action (like untreated control)
100% = total destruction In this test, a clearly superior activity compared with the comparison substance (A) is shown, for example, by the compounds of Preparation Examples 16, 17, 18 and 19.

It is understood that the specification and examples are illustrative but not limitative of the present invention and that other embodiments within the spirit and scope of the invention will suggest themselves to those skilled in the art.

We claim:

1. A 4-alkylideneamino-5-amino-1,2,4-triazol-3-(thi)-one of the formula

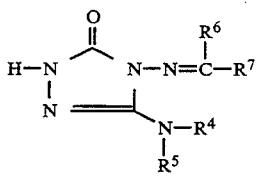

(XXI)

$R^4$ and $R^5$ are identical or different and independently of one another represent hydrogen, or represent in each case straight-chain or branched alkyl having 1 to 8 carbon atoms, alkenyl having 2 to 8 carbon atom's, alkinyl having 2 to 8 carbon atoms, halogenoalkyl having 1 to 8 carbon atoms and 1 to 17 identical or different halogen atoms, halogenoalkenyl or halogenoalkinyl, in each case having 2 to 8 carbon atoms and 1 to 15, or 13, identical or different halogen atoms, cyanoalkyl having 1 to 8 carbon atoms, or alkoxyalkyl or alkylthioalkyl, in each case having up to 4 carbon atoms in the individual alkyl moieties, or represent cycloalkyl or cycloalkylalkyl, each of which has 3 to 8 carbon atoms in the cycloalkyl moiety and, where appropriate, 1 to 6 carbon atoms in the alkyl moiety and each of which is optionally monosubstituted to trisubstituted by identical or different substituents selected from the group consisting of halogen, cyano as well as in each case straight-chain or branched alkyl or halogenoalkyl, in each case having 1 to 4 carbon atoms and, where appropriate, 1 to 9 identical or different halogen atoms, or the radicals $R^4$ and $R^5$ furthermore represent aryl or aralkyl, each of which has 6 or 10 carbon atoms in the aryl moiety and, where appropriate, 1 to 4 carbon atoms in the straight-chain or branched alkyl moiety and each of which is optionally monosubstituted to trisubstituted by identical or different substituents selected from the group consisting of halogen, cyano, nitro, hydroxyl, in each case straight-chain or branched alkyl, alkoxy, alkylthio, halogenoalkyl, halogenoalkoxy, halogeno, alkylthio, alkylsulphinyl, alkylsulphonyl, halogenoalkylsulphinyl, halogenoalkylsulphonyl, alkanoyl and alkoxycarbonyl, in each case having 1 to 6 carbon atoms in the alkyl moiety and, where appropriate, 1 to 9 halogen atoms, and $R^5$ can also represent straight-chain or branched alkoxy having 1 to 8 carbon atoms, and $R^6$ and $R^7$ are identical or different and independently of one another represent in each case straight-chain or branched alkyl having 1 to 8 carbon atoms and optionally monosubstituted to trisubstituted by identical or different substituents selected from the group consisting of halogen or cyano, or the radicals $R^6$ and $R^7$ furthermore represent aralkyl which has 6 or 10 carbon atoms in the aryl moiety and, where appropriate, 1 to 4 carbon atoms in the straight-chain or branched alkyl moiety and each of which is optionally monosubstituted to trisubstituted by identical or different substituents selected from the group consisting of halogen, cyano, nitro, hydroxyl, in each case straight-chain or branched alkyl, alkoxy, alkylthio, halogenoalkyl, halogenoalkoxy, halogenoalkylthio, alkylsulphinyl, alkylsulphonyl, halogenoalkylsulphinyl, halogenoalkylsulphonyl, alkanoyl and alkoxycarbonyl, in each case having 1 to 6 carbon atoms in the alkyl moiety and, where appropriate, 1 to 9 halogen atoms.

2. A compound according to claim 1 of the formula

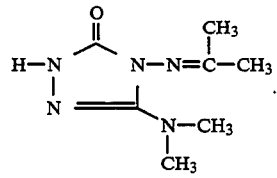

* * * * *

UNITED STATES PATENT AND TRADEMARK OFFICE
CERTIFICATE OF CORRECTION

PATENT NO. : 5,399,704

DATED : March 21, 1995

INVENTOR(S) : Muller, et al.

It is certified that error appears in the above-identified patent and that said Letters Patent is hereby corrected as shown below:

Col. 92, line 47     Insert -- in which --

Col. 93, lines 12-13     Delete " halogeno, alkylthio " and substitute -- halogenoalkylthio --

Signed and Sealed this

Thirtieth Day of May, 1995

Attest:

BRUCE LEHMAN

*Attesting Officer*     *Commissioner of Patents and Trademarks*